US008485961B2

(12) United States Patent
Campbell et al.

(10) Patent No.: US 8,485,961 B2
(45) Date of Patent: Jul. 16, 2013

(54) IMPELLER HOUSING FOR PERCUTANEOUS HEART PUMP

(75) Inventors: Robert L. Campbell, Port Matilda, PA (US); Keif Fitzgerald, San Jose, CA (US); William James Harrison, Signal Mountain, TN (US); Boris Leschinsky, Mahwah, NJ (US); Thomas M. Mallison, State College, PA (US); Mark W. McBride, Bellefonte, PA (US); Adam Roslund, Monroeville, PA (US); Daniel A. Walters, Rockaway Township, NJ (US); Phyllis Yuen, Fremont, CA (US)

(73) Assignees: Thoratec Corporation, Pleasanton, CA (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 13/343,617

(22) Filed: Jan. 4, 2012

(65) Prior Publication Data

US 2012/0172655 A1   Jul. 5, 2012

Related U.S. Application Data

(60) Provisional application No. 61/430,146, filed on Jan. 5, 2011.

(51) Int. Cl.
*A61N 1/362* (2006.01)
(52) U.S. Cl.
USPC ............................................................ 600/16
(58) Field of Classification Search
USPC ............................................................ 600/16
See application file for complete search history.

(56) References Cited

U.S. PATENT DOCUMENTS

| 1,902,418 A | 3/1933 | Pilgrim |
| 2,356,659 A | 10/1942 | Aguiar |
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |

(Continued)

FOREIGN PATENT DOCUMENTS

| CA | 2367469 | 10/2000 |
| EP | 0 533 432 | 9/1992 |

(Continued)

OTHER PUBLICATIONS

Extended European Search Report dated Oct. 8, 2012, received in European Patent Application No. 07753903.9.

(Continued)

*Primary Examiner* — George Manuel
(74) *Attorney, Agent, or Firm* — Knobbe Martens Olson & Bear LLP

(57) ABSTRACT

Disclosed herein are heart pumps that include a catheter assembly and that can be applied percutaneously. Some embodiments include a locking device that prevents components of the catheter assembly from being separated when in use. The catheter assembly can include an expandable tip. In some embodiments, the catheter assembly includes a housing having a wall structure, a portion of which can have a bulbuous shape or can be deformable. In other embodiments, the housing can be configured to reduce fluttering or deflection of the housing and/or to maintain a gap between the housing and an impeller blade disposed therein.

51 Claims, 45 Drawing Sheets

U.S. PATENT DOCUMENTS

| | | |
|---|---|---|
| 2,896,926 A | 7/1959 | Chapman |
| 2,935,068 A | 5/1960 | Donaldson |
| 3,080,824 A | 3/1963 | Boyd et al. |
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |
| 3,904,901 A | 9/1975 | Renard et al. |
| 3,995,617 A | 12/1976 | Watkins et al. |
| 4,129,129 A | 12/1978 | Amrine |
| 4,135,253 A | 1/1979 | Reich et al. |
| 4,149,535 A | 4/1979 | Volder |
| 4,304,524 A | 12/1981 | Coxon et al. |
| 4,392,836 A | 7/1983 | Sugawara |
| 4,458,366 A | 7/1984 | MacGregor |
| 4,540,402 A | 9/1985 | Aigner |
| 4,589,822 A | 5/1986 | Clausen et al. |
| 4,625,712 A | 12/1986 | Wampler |
| 4,655,745 A | 4/1987 | Corbett |
| 4,686,982 A | 8/1987 | Nash |
| 4,704,121 A | 11/1987 | Moise |
| 4,753,221 A | 6/1988 | Kensey et al. |
| 4,769,006 A | 9/1988 | Papantonakos |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,955,856 A | 9/1990 | Phillips |
| 4,957,504 A | 9/1990 | Chardack |
| 4,964,864 A | 10/1990 | Summers et al. |
| 4,969,865 A | 11/1990 | Hwang et al. |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,021,048 A | 6/1991 | Buckholtz |
| 5,049,134 A | 9/1991 | Golding et al. |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,349 A | 5/1992 | Summers et al. |
| 5,129,883 A | 7/1992 | Black |
| 5,147,186 A | 9/1992 | Buckholtz |
| 5,163,910 A | 11/1992 | Schwartz et al. |
| 5,171,212 A | 12/1992 | Buck et al. |
| 5,190,528 A | 3/1993 | Fonger et al. |
| 5,201,679 A | 4/1993 | Velte et al. |
| 5,211,546 A | 5/1993 | Isaacson et al. |
| 5,290,227 A | 3/1994 | Pasque |
| 5,300,112 A | 4/1994 | Barr |
| 5,312,341 A | 5/1994 | Turi |
| 5,346,458 A | 9/1994 | Affeld |
| 5,360,317 A | 11/1994 | Clausen et al. |
| 5,376,114 A | 12/1994 | Jarvik |
| 5,405,383 A | 4/1995 | Barr |
| 5,437,541 A | 8/1995 | Vainrub et al. |
| 5,449,342 A | 9/1995 | Hirose et al. |
| 5,458,459 A | 10/1995 | Hubbard et al. |
| 5,505,701 A | 4/1996 | Anaya Fernandez de Lomana |
| 5,527,159 A | 6/1996 | Bozeman, Jr. et al. |
| 5,533,957 A | 7/1996 | Aldea |
| 5,588,812 A | 12/1996 | Taylor et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman et al. |
| 5,707,218 A | 1/1998 | Maher et al. |
| 5,722,930 A | 3/1998 | Larson et al. |
| 5,738,649 A | 4/1998 | Macoviak |
| 5,741,234 A | 4/1998 | Aboul-Hosn |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,868,702 A | 2/1999 | Stevens |
| 5,868,703 A | 2/1999 | Bertolero |
| 5,888,242 A | 3/1999 | Antaki et al. |
| 5,911,685 A | 6/1999 | Siess et al. |
| 5,921,913 A | 7/1999 | Siess |
| 5,941,813 A | 8/1999 | Sievers et al. |
| 5,951,263 A | 9/1999 | Taylor et al. |
| 5,964,694 A | 10/1999 | Siess et al. |
| 6,007,478 A | 12/1999 | Siess et al. |
| 6,007,479 A | 12/1999 | Rottenberg et al. |
| 6,015,272 A | 1/2000 | Antaki et al. |
| 6,056,719 A | 5/2000 | Mickley |
| 6,058,593 A | 5/2000 | Siess |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,943 A | 10/2000 | Yu et al. |
| 6,136,025 A | 10/2000 | Barbut et al. |
| 6,139,487 A | 10/2000 | Siess |
| 6,152,704 A | 11/2000 | Aboul-Hosn et al. |
| 6,176,822 B1 | 1/2001 | Nix et al. |
| 6,176,848 B1 | 1/2001 | Rau et al. |
| 6,190,304 B1 | 2/2001 | Downey et al. |
| 6,200,260 B1 | 3/2001 | Bolling |
| 6,210,133 B1 | 4/2001 | Aboul-Hosn et al. |
| 6,210,397 B1 | 4/2001 | Aboul-Hosn et al. |
| 6,227,797 B1 | 5/2001 | Watterson et al. |
| 6,228,063 B1 | 5/2001 | Aboul-Hosn |
| 6,234,960 B1 | 5/2001 | Aboul-Hosn et al. |
| 6,245,007 B1 | 6/2001 | Bedingham et al. |
| 6,247,892 B1 | 6/2001 | Kazatchkov et al. |
| 6,248,091 B1 | 6/2001 | Voelker |
| 6,254,359 B1 | 7/2001 | Aber |
| 6,287,319 B1 | 9/2001 | Aboul-Hosn et al. |
| 6,295,877 B1 | 10/2001 | Aboul-Hosn et al. |
| 6,387,037 B1 | 5/2002 | Bolling et al. |
| 6,395,026 B1 | 5/2002 | Aboul-Hosn et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | de Blanc et al. |
| 6,609,883 B2 | 8/2003 | Woodard et al. |
| 6,610,004 B2 * | 8/2003 | Viole et al. .................. 600/16 |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,641,558 B1 | 11/2003 | Aboul-Hosn et al. |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,783,328 B2 | 8/2004 | Lucke et al. |
| 6,790,171 B1 | 9/2004 | Grundeman et al. |
| 6,794,789 B2 | 9/2004 | Siess et al. |
| 6,814,713 B2 | 11/2004 | Aboul-Hosn et al. |
| 6,817,836 B2 | 11/2004 | Nose et al. |
| 6,860,713 B2 | 3/2005 | Hoover |
| 6,866,625 B1 | 3/2005 | Avre et al. |
| 6,889,082 B2 | 5/2005 | Bolling et al. |

| | | |
|---|---|---|
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,241,257 B1 | 7/2007 | Ainsworth et al. |
| 7,264,606 B2 * | 9/2007 | Jarvik et al. ................. 604/6.11 |
| 7,284,956 B2 | 10/2007 | Nose et al. |
| 7,329,236 B2 | 2/2008 | Keren et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride |
| 7,491,163 B2 | 2/2009 | Viole et al. |
| 7,605,298 B2 | 10/2009 | Bechert et al. |
| 7,619,560 B2 | 11/2009 | Penna |
| 7,731,675 B2 | 6/2010 | Aboul-Hosn et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,819,833 B2 | 10/2010 | Ainsworth et al. |
| 7,828,710 B2 | 11/2010 | Shifflette |
| 7,841,976 B2 | 11/2010 | Mc Bride et al. |
| 7,927,068 B2 | 4/2011 | McBride et al. |
| 7,942,804 B2 | 5/2011 | Khaw |
| 7,942,844 B2 | 5/2011 | Moberg et al. |
| 7,993,259 B2 | 8/2011 | Kang et al. |
| 7,998,054 B2 | 8/2011 | Bolling |
| 8,079,948 B2 | 12/2011 | Shifflette |
| 8,110,267 B2 | 2/2012 | Houston et al. |
| 8,177,703 B2 | 5/2012 | Smith et al. |
| 8,206,350 B2 | 6/2012 | Mann et al. |
| 2002/0151761 A1 | 10/2002 | Viole et al. |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2005/0049696 A1 | 3/2005 | Siess et al. |
| 2005/0085683 A1 | 4/2005 | Bolling et al. |
| 2005/0165269 A9 | 7/2005 | Aboul-Hosn et al. |
| 2006/0018943 A1 | 1/2006 | Bechert et al. |
| 2006/0058869 A1 | 3/2006 | Olson et al. |
| 2006/0063965 A1 | 3/2006 | Aboul-Hosn et al. |
| 2006/0155158 A1 | 7/2006 | Aboul-Hosn |
| 2006/0264695 A1 | 11/2006 | Viole et al. |
| 2006/0270894 A1 | 11/2006 | Viole et al. |
| 2007/0100314 A1 | 5/2007 | Keren et al. |
| 2008/0103442 A1 | 5/2008 | Kesten et al. |
| 2008/0103591 A1 | 5/2008 | Siess |
| 2008/0167679 A1 | 7/2008 | Papp |
| 2008/0275290 A1 | 11/2008 | Viole et al. |
| 2009/0023975 A1 | 1/2009 | Marseille et al. |
| 2009/0062597 A1 | 3/2009 | Shifflette |
| 2009/0093764 A1 | 4/2009 | Pfeffer et al. |
| 2009/0093765 A1 | 4/2009 | Glenn |
| 2009/0093796 A1 | 4/2009 | Pfeffer et al. |
| 2009/0171137 A1 | 7/2009 | Farnan et al. |
| 2009/0182188 A1 | 7/2009 | Marseille et al. |
| 2010/0087773 A1 | 4/2010 | Ferrari |
| 2010/0127871 A1 | 5/2010 | Pontin |
| 2010/0197994 A1 | 8/2010 | Mehmanesh |
| 2010/0210895 A1 | 8/2010 | Aboul-Hosn et al. |
| 2010/0286210 A1 | 11/2010 | Murata et al. |
| 2011/0004046 A1 | 1/2011 | Campbell et al. |
| 2011/0021865 A1 | 1/2011 | Aboul-Hosn et al. |
| 2011/0034874 A1 | 2/2011 | Reitan |
| 2011/0071338 A1 | 3/2011 | McBride et al. |
| 2011/0076439 A1 | 3/2011 | Zeilon |
| 2011/0236210 A1 | 9/2011 | McBride et al. |
| 2011/0257462 A1 | 10/2011 | Rodefeld |
| 2012/0004495 A1 | 1/2012 | Bolling |
| 2012/0172656 A1 | 7/2012 | Walters et al. |
| 2012/0178985 A1 | 7/2012 | Walters et al. |
| 2012/0178986 A1 | 7/2012 | Campbell et al. |

FOREIGN PATENT DOCUMENTS

| | | |
|---|---|---|
| EP | 1207934 | 5/2002 |
| EP | 2151257 A1 | 2/2010 |
| EP | 2 263 732 A2 | 12/2010 |
| FR | 2267800 | 4/1974 |
| JP | S48-23295 | 3/1973 |
| JP | H06-114101 | 4/1994 |
| JP | H08-196624 | 8/1996 |
| JP | 10-099447 | 4/1998 |
| JP | 2002-505168 | 2/2002 |
| JP | 2011-000620 | 9/2005 |
| JP | 2011-157961 | 8/2011 |
| WO | WO 89/04644 | 6/1989 |
| WO | WO 89/05164 A1 | 6/1989 |
| WO | WO 97/15228 | 5/1997 |
| WO | WO 99/37352 | 7/1999 |
| WO | WO 00/12148 | 3/2000 |
| WO | WO 00/18448 | 4/2000 |
| WO | WO 00/19097 | 4/2000 |
| WO | WO 00/43053 | 7/2000 |
| WO | WO 00/61207 | 10/2000 |
| WO | WO 00/69489 | 11/2000 |
| WO | WO 01/24867 | 4/2001 |
| WO | WO 02/070039 | 9/2002 |
| WO | WO 03/068303 | 8/2003 |
| WO | WO 03/103745 | 12/2003 |
| WO | WO 2005/089674 | 9/2005 |
| WO | WO 2005/123158 | 12/2005 |
| WO | WO 2007/112033 | 10/2007 |
| WO | WO 2008-034068 | 3/2008 |
| WO | WO 2009/073037 | 6/2009 |
| WO | WO 2010/127871 | 11/2010 |
| WO | WO 2010/149393 | 12/2010 |
| WO | WO 2011/003043 | 1/2011 |
| WO | WO 2011/035926 | 3/2011 |
| WO | WO 2011/035929 | 3/2011 |
| WO | WO 2011/076439 | 6/2011 |
| WO | WO 2011/089022 | 7/2011 |
| WO | WO 2012/007140 | 1/2012 |
| WO | WO 2012/007141 | 1/2012 |

OTHER PUBLICATIONS

ABIOMED—Recovering hearts. Saving lives., Impella 2.5 System, Instructions for Use, Jul. 2007, 86 sheets.
Cardiovascular Diseases (CVDs) Fact Sheet No. 317. World Health Organization. [Online] Sep. 2011. http://www.who.int/mediacentre/factsheets/fs317/en/index.html, accessed on Aug. 29, 2012.
European Search Report received from the European Patent Office in EP Application No. EP 05799883.3 dated May 10, 2011, 4 pages.
Ide, Hirofumi et al., Evaluation of the Pulsatility of a New Pulsatile Left Ventricular Assist Device—the Integrated Cardioassist Catheter—in Dogs, J. of Thoracic and Cardiovascular Surgery 107 (2): 569-75; Feb. 1994.
Ide, Hirofumi et al., Hemodynamic Evaluation of a New Left Ventricular Assist Device, Artificial Organs 16 (3): 286-90; 1992.
International Preliminary Examination Report from the European Patent Office received in PCT Application No. PCT/US2003/04853, mailed Jul. 26, 2004, 5 pages.
International Preliminary Examination Report from the European Patent Office received in PCT Application No. PCT/US2003/04401, mailed May 18, 2004, 4 pages.
International Preliminary Report on Patentability and Written Opinion of the International Searching Authority received in PCT Application No. PCT/US2005/033416, mailed Mar. 20, 2007, 7 pages.

International Preliminary Report on Patentability of the International Searching Authority received in PCT Application No. PCT/US2007/007313, mailed Sep. 23, 2008, 6 pages.
International Search Report and Written Opinion received in PCT Application No. PCT/US2005/33416, mailed Dec. 11, 2006, 4 pages.
International Search Report and Written Opinion received in PCT Application No. PCT/US2007/07313, mailed Mar. 4, 2008, 8 pages.
International Search Report received in PCT Application No. PCT/US2003/04401, mailed Nov. 10, 2003, 9 pages.
International Search Report received in PCT Application No. PCT/US2003/04853, mailed Jul. 3, 2003, 3 pages.
International Search Report Written Opinion received in PCT Application No. PCT/US2010/040847 mailed on Dec. 14, 2010.
International Search Report and Written Opinion received in PCT Application No. PCT/US2012/020382, mailed Jul. 31, 2012.
International Search Report and Written Opinion received in PCT Application No. PCT/US2012/020369 mailed Jul. 30, 2012.
International Search Report and Written Opinion received in PCT Application No. PCT/US2012/020553 mailed Aug. 17, 2012.
International Search Report and Written Opinion received in PCT Application No. PCT/US2012/020383 mailed Aug. 17, 2012.
Mihaylov, D. et al., Evaluation of the Optimal Driving Mode During Left Ventricular Assist with Pulsatile Catheter Pump in Calves, Artificial Organs 23(12): 1117-22; 1999.
Mihaylov, Dimiter et al., Development of a New Introduction Technique for the Pulsatile Catheter Pump, Artificial Organs 21(5): 425-27; 1997.
Morsink, PLJ et al., Numerical Modelling of Blood Flow Behaviour in the Valved Catheter of the PUCA Pump, a LVAD, The International Journal of Artificial Organs 20(5): 277-284; 1997.
Nishimura et al. The enabler cannula pump: a novel circulatory support system. The International Journal of Artificial Organs, vol. 22, No. 5, 1999, pp. 317-323.
Rakhorst, Gerhard et al., In Vitro Evaluation of the Influence of Pulsatile Intraventricular Pumping on Ventricular Pressure Patterns, Artificial Organs 18(7): 494-99; 1994.
Reitan, Oyvind, et al., Hydrodynamic Properties of a New Percutaneous Intra-aortic Axial Flow Pump. Reitan et al. ASAIO Journal 2000. pp. 323-328.
Schmitz-Rode, Thomas et al., "An Expandable Percutaneous Catheter Pump for Left Ventricular Support", Journal of the American College of Cardiology, vol. 45, No. 11, 2005, pp. 1856-1861.
Sharony et al. Cardiopulmonary Support and Physiology—The Intra-Aortic Cannula Pump: A Novel Assist Device for the Acutely Failing Heart. The Journal of Thoracic and Cardiovascular Surgery, Nov. 1992, vol. 118, No. 5, pp. 924-929.
Sharony, R. et al. Right heart support during off-pump coronary artery surgery—a multi-center study. Heart Surg Forum. 2002;5(1):13-6.
"Statistical Analysis and Clinical Experience with the Recover® Pump Systems", Impella CardioSystems GmbH, 2 sheets, 2005.
Supplementary European Search Report received from the European Patent Office in EP Application No. EP 05799883 dated Mar. 19, 2010, 3 pages.
Takagaki et al. A Novel Miniature Ventricular Assist Device for Hemodynamic Support. ASAIO Journal 2001, pp. 412-416.
Verkerke, Gijsbertus et al., Numerical Simulation of the Pulsating Catheter Pump: A Left Ventricular Assist Device, Artificial Organs 23(10): 924-31; 1999.
Verkerke, Bart et al., The PUCA Pump: A Left Ventricular Assist Device, Artificial Organs 17(5): 365-68; 1993.
Verkerke, CJ et al., Numerical Simulation of the PUCA Pump, A Left Ventricular Assist Device, Abstracts of the XIXth ESAO Congress, The International Journal of Artificial Organs 15(9): 543; 1992.
Wampler, Richard. K., et al., The Sternotomy Hemopump, A Second Generation Intraarterial Ventricular Assist Device; Johnson and Johnson Interventional Systems, pp. M218-M220, 223, 1993.
Written Opinion received in PCT Application No. PCT/US2003/04853, dated Feb. 25, 2004, 5 pages.
Office Action received in U.S. Appl. No. 12/829,359, dated Dec. 18, 2012, filed Jul. 1, 2010, in 22 pages.

* cited by examiner

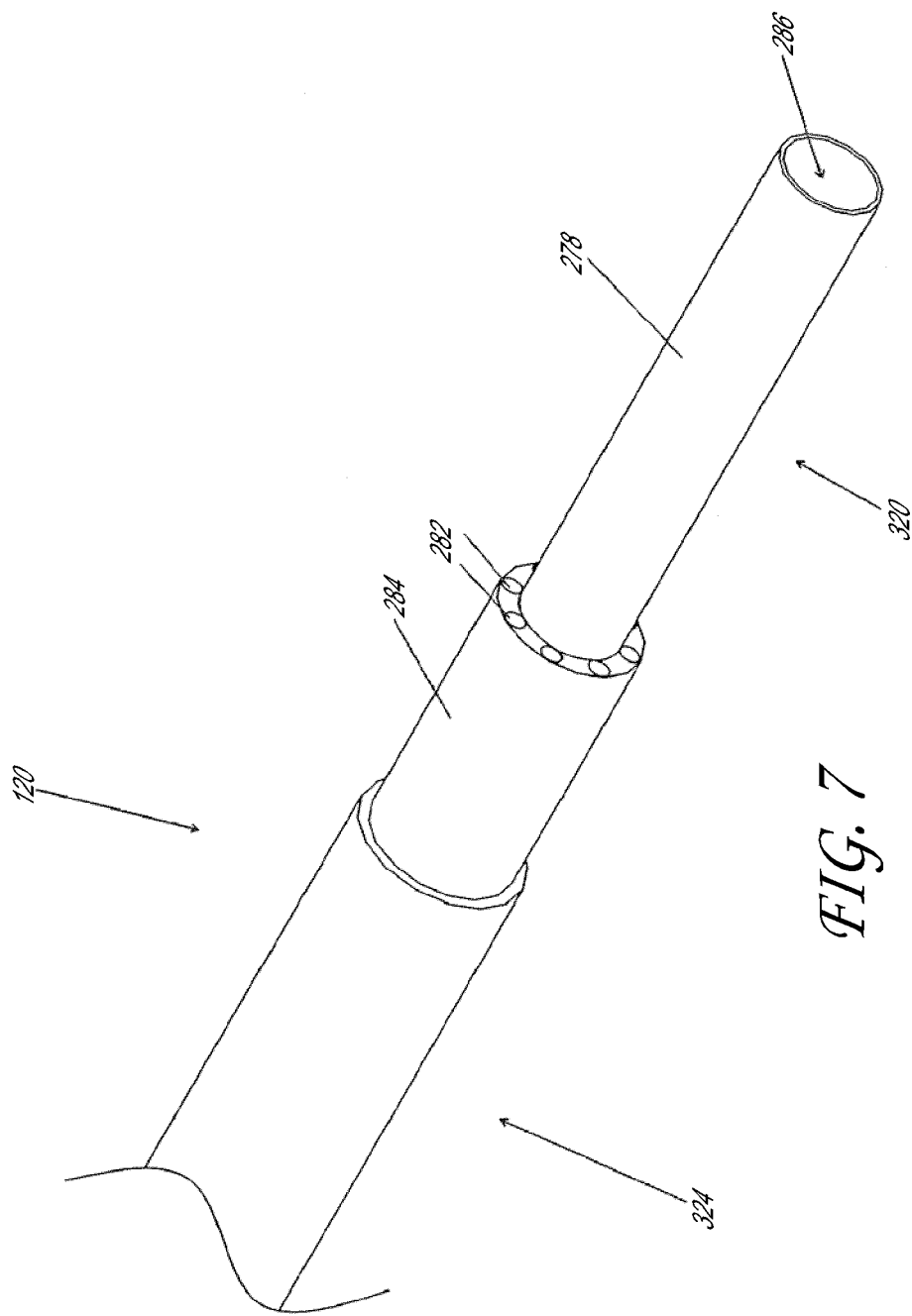

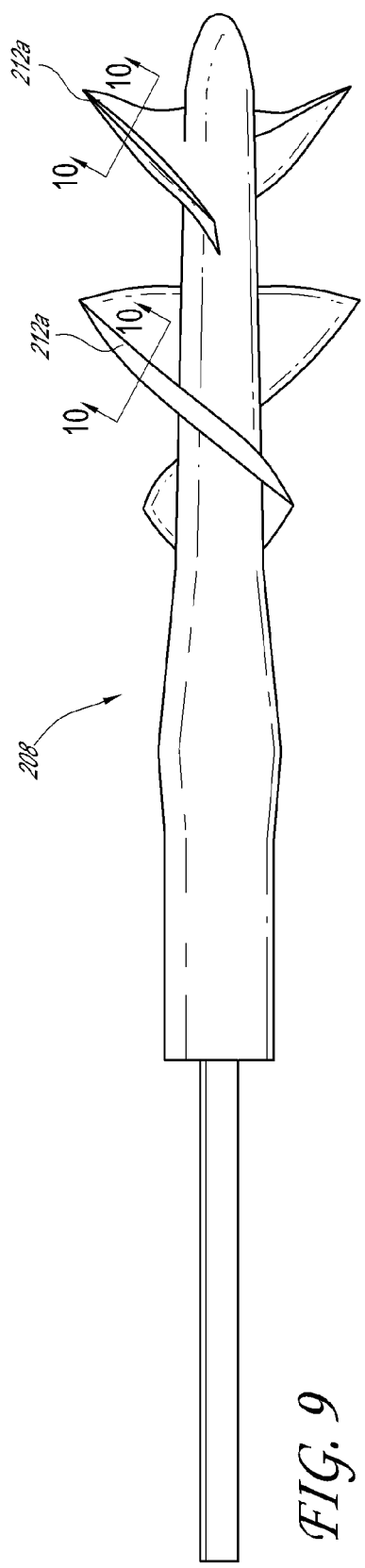
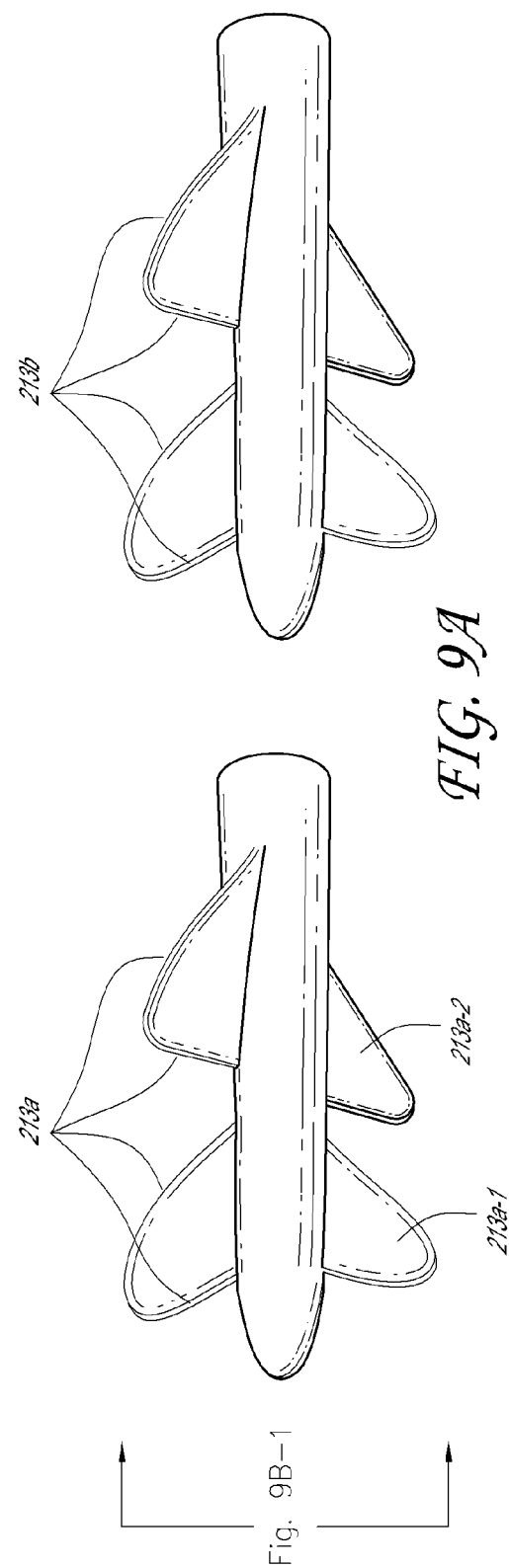

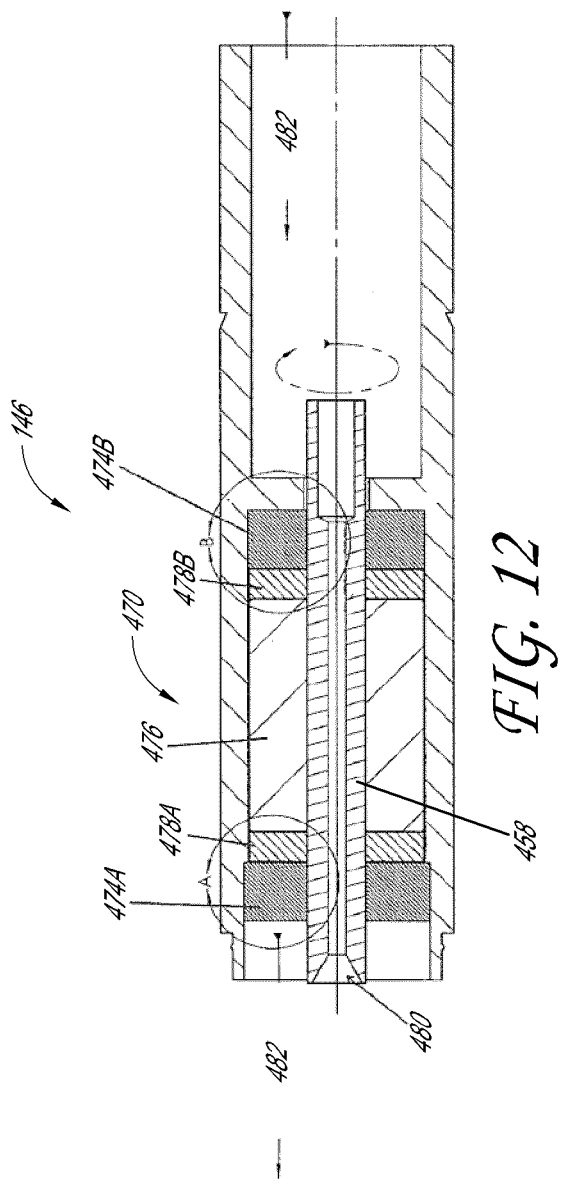
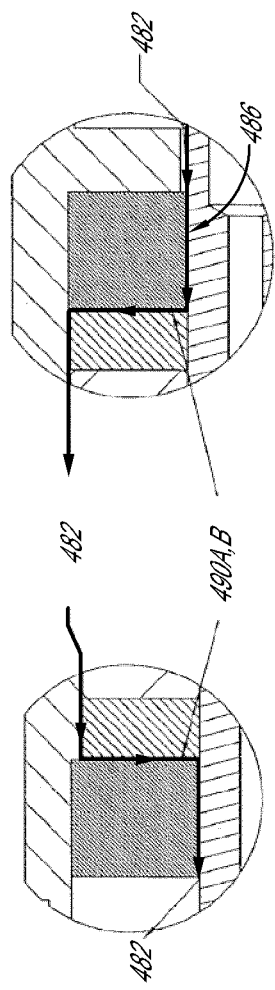
FIG. 12
FIG. 12B
FIG. 12A

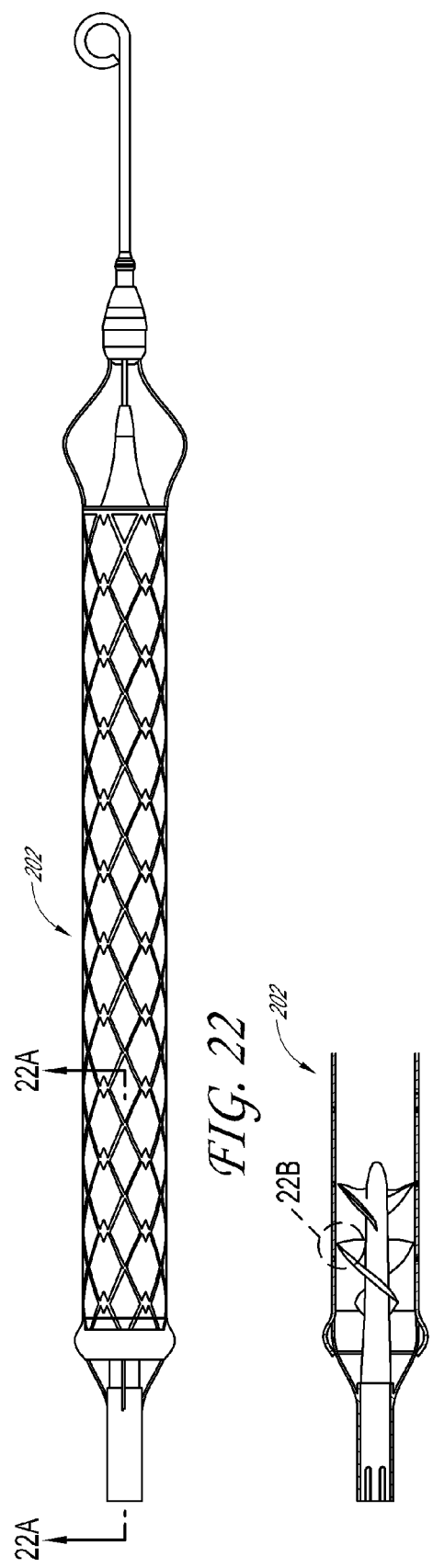
FIG. 22
FIG. 22A
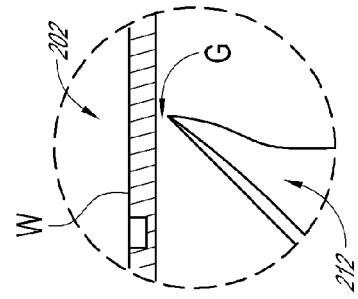
FIG. 22B

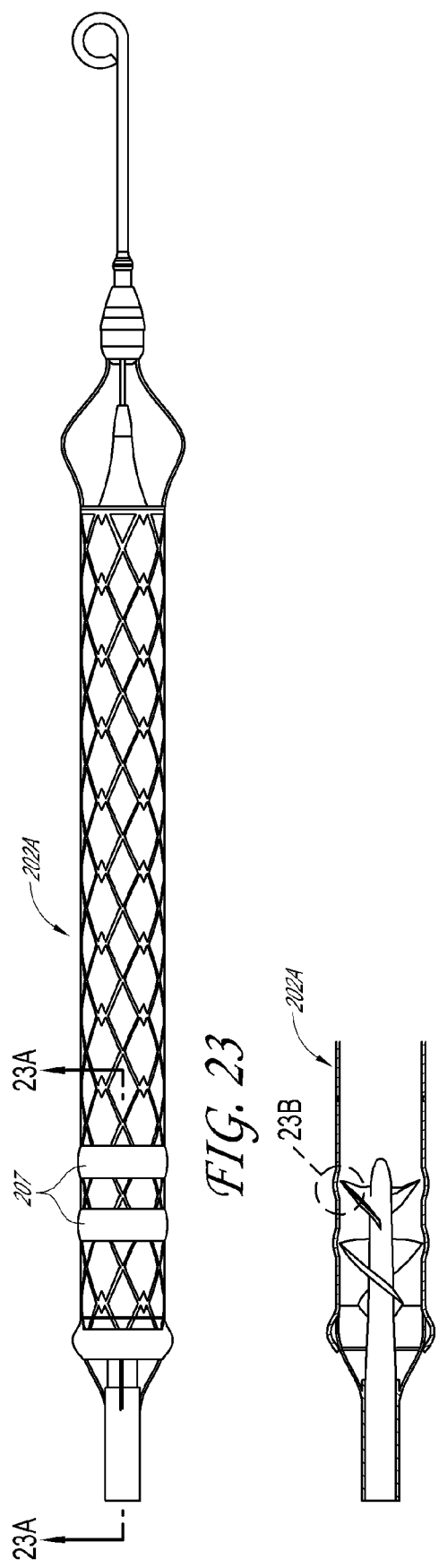
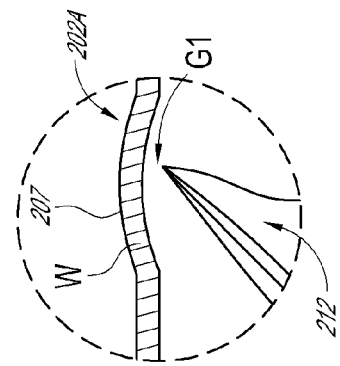
FIG. 23
FIG. 23A
FIG. 23B

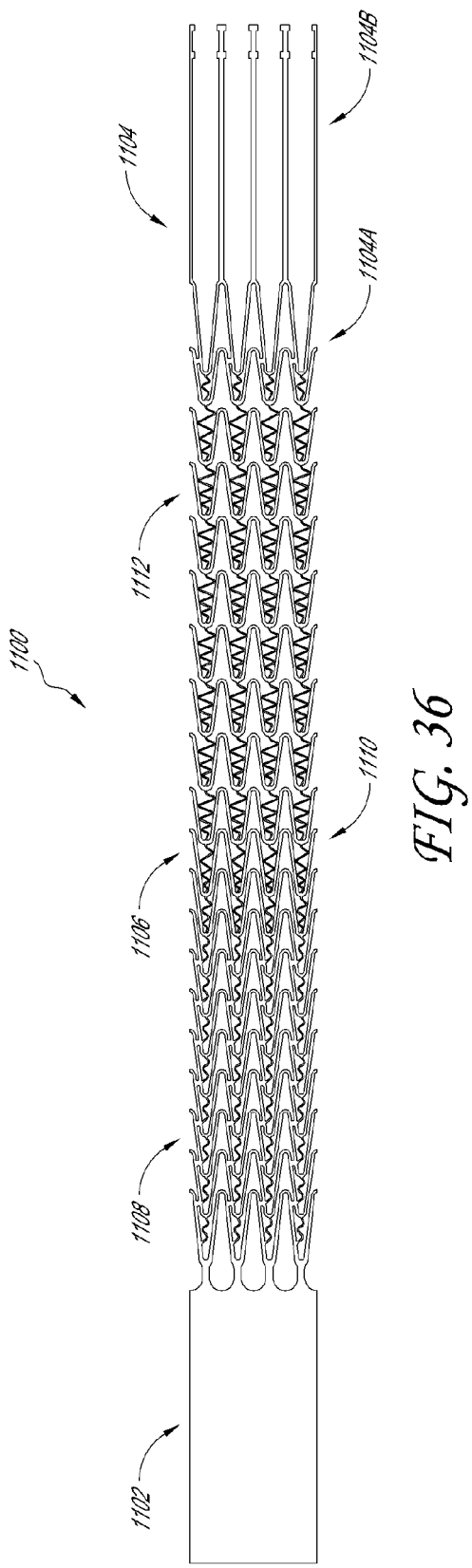

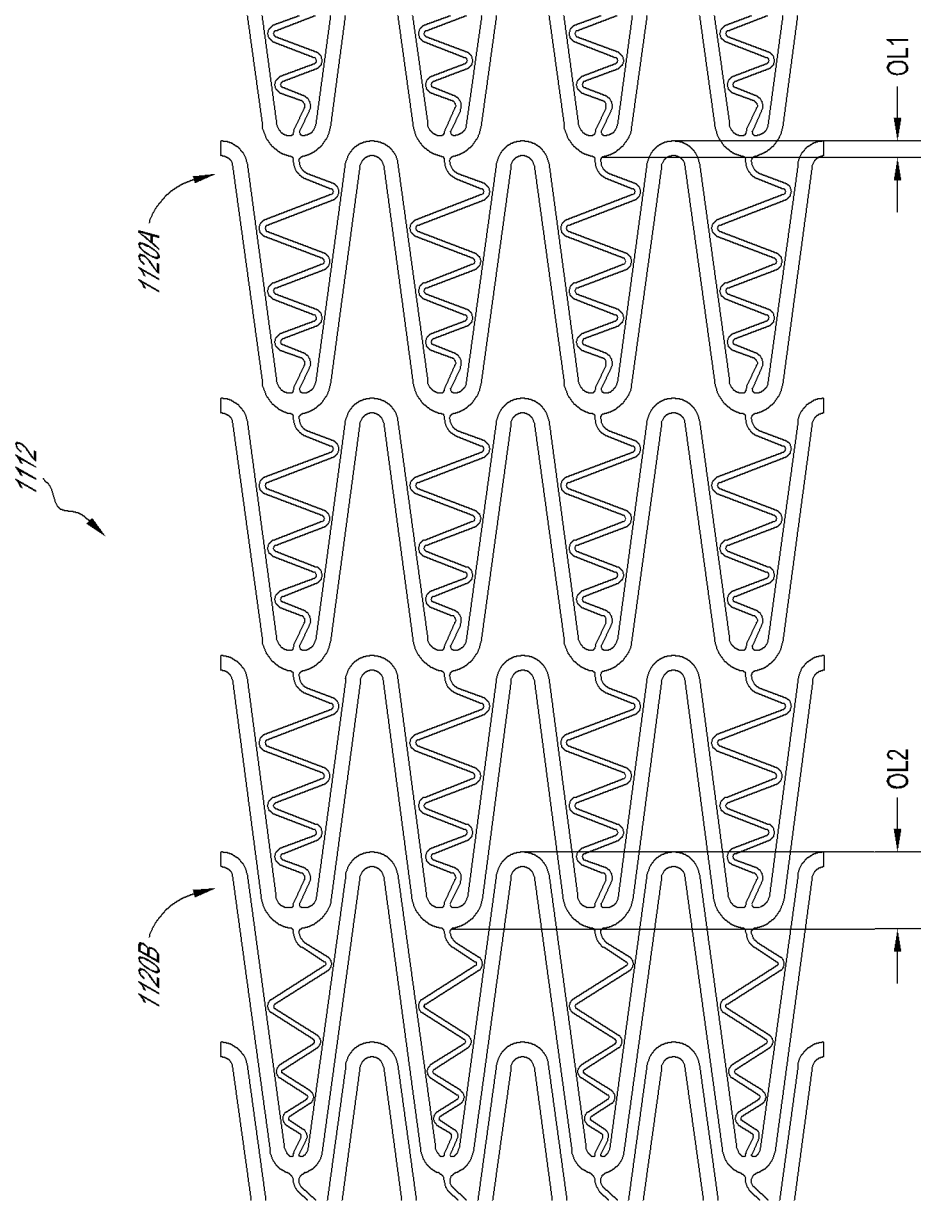

IMPELLER HOUSING FOR PERCUTANEOUS HEART PUMP

CROSS-REFERENCE TO RELATED APPLICATIONS

This application claims priority to U.S. Provisional Application Ser. No. 61/430,146 filed Jan. 5, 2011 entitled Impeller Housing For Percutaneous Heart Pump, which is hereby incorporated by reference herein for all purposes.

BACKGROUND OF THE INVENTION

1. Field of the Invention

This application is directed to heart pumps that can be applied percutaneously.

2. Description of the Related Art

Heart disease is a major health problem that claims many lives per year. After a heart attack, only a small number of patients can be treated with medicines or other non-invasive treatment. However, a significant number of patients can recover from a heart attack or cardiogenic shock if provided with mechanical circulatory support.

In a conventional approach, a blood pump having a fixed cross-section is surgically inserted a heart chamber, such as into the left ventricle of the heart and the aortic arch to assist the pumping function of the heart. Other known applications involve providing for pumping venous blood from the right ventricle to the pulmonary artery for support of the right side of the heart. The object of the surgically inserted pump is to reduce the load on the heart muscle for a period of time, which may be as long as a week, allowing the affected heart muscle to recover and heal. Surgical insertion, however, can cause additional serious stresses in heart failure patients.

Percutaneous insertion of a left ventricular assist device ("LVAD"), a right ventricular assist device ("RVAD") or in some cases a system for both sides of the heart (sometimes called biVAD) therefore is desired. Conventional fixed cross-section ventricular assist devices designed to provide near full heart flow rate are too large to be advanced percutaneously, e.g., through the femoral artery. There is an urgent need for a pumping device that can be inserted percutaneous and also provide full cardiac rate flows of the left, right, or both the left and right sides of the heart when called for.

SUMMARY OF THE INVENTION

A catheter assembly for a heart pump is provided that includes an elongate tubular member and a hub coupled with a proximal end of the elongate tubular member. Optionally, the hub has an increasing outer profile along its length. The catheter assembly includes a plurality of structural members forming a distal portion of an impeller housing and a locking device disposed between the structural members and the hub. The locking device is configured to prevent the elongate tubular member from being separated from the structural members when the catheter assembly is in use.

In another embodiment, an impeller assembly for a heart pump is provided that includes an impeller housing, an impeller assembly, and a stiffening member. The impeller housing comprises a fixed profile proximal portion, an expandable portion, and a plurality of struts extending therebetween. The struts have a proximal end coupled with the proximal portion of the impeller housing and a distal end coupled with the expandable portion of the impeller housing and movable with the expandable portion of the impeller housing from a low profile configuration to a higher profile configuration. The an impeller assembly includes an impeller shaft journaled for rotation within the impeller housing and at least one impeller blade supported by the impeller shaft for rotation within the expandable portion of the impeller housing. The stiffening member is coupled with the proximal portion of the impeller housing and with the expandable portion of the impeller housing. The stiffening member is configured to limit deflection of at least one of the impeller shaft, the impeller blade or the impeller housing from a desired position relative to a central axis of the impeller assembly.

In another embodiment, a catheter assembly for a heart pump is provided. The catheter assembly includes an impeller shaft and an impeller blade extending from the impeller shaft and a housing in which the impeller shaft is journaled for rotation. The housing has an elongate wall structure disposed circumferentially about the impeller blade. The elongate wall structure extends distally and proximally of the impeller blade. The wall structure is sufficiently deformable to be displaced by ambient conditions during operation of the impeller assembly within a patient.

In some embodiments impeller assembly is modified such that the wall structure is made stiffer to control deflections of the wall of the housing at the location of the impeller blade or blades.

In some variations the stiffness of the housing varies along the length thereof such that more deflection or deformation is provided for proximal, distal or proximal and distal of the region of the impeller blade or blades.

In some variations the stiffness of the housing is increased such that little if any deflection of the wall is anticipated under normal operating conditions of a heart pump in which the impeller housing is incorporated. This arrangement may be useful where deflections during rotation of the impeller shaft and blade or blades are very tightly controlled in normal operational conditions.

In another embodiment, a catheter assembly for a heart pump is provided. The catheter assembly includes an impeller shaft and an impeller blade extending from the impeller shaft and an impeller housing in which the impeller shaft is journaled for rotation. The housing includes an inlet, an outlet, and an elongate wall structure disposed circumferentially about the impeller blade. The housing extends distally and proximally of the impeller blade between the inlet and outlet. The wall structure adjacent to at least one of the inlet and the outlet is configured to maintain a bulbous shape when deployed.

In another embodiment, an impeller assembly for a heart pump is provided that includes an impeller shaft and an impeller blade extending from the impeller shaft. The impeller assembly also includes a housing in which the impeller shaft is journaled for rotation. The housing comprising an impeller blade zone, an inlet zone, and an outlet zone, the impeller blade zone being elongate and having a substantially constant transverse size zone at least from proximal of the impeller blade to distal of the impeller blade. The impeller zone is disposed between the inlet zone and the outlet zone. At least one of the inlet zone and the outlet zone is configured to reduce fluttering of the housing when the heart pump is operating.

In another embodiment, a catheter assembly for a heart pump is provided that includes an elongate tubular member, and an expandable housing disposed at the distal end of the elongate tubular member, and an expandable tip. The expandable housing is configured to house an impeller and to convey blood from an intake toward the impeller in use. The expandable tip is coupled with the distal end of the expandable housing. The expandable tip has a collapsed configuration in which a tapered profile is provided for facilitating advancement through an anatomical structure. The expandable tip has an expanded configuration for spacing the intake from the anatomy adjacent to where the pump operates.

In another embodiment, a catheter assembly for a heart pump is disclosed that comprises an impeller shaft and an impeller blade extending from the impeller shaft. The catheter assembly further includes a housing in which the impeller shaft is journaled for rotation, the housing having an elongate wall structure disposed circumferentially about the impeller blade and extending distally and proximally thereof. A distal region of the wall structure can be configured to isolate a proximal region of the wall structure from deflection due to application of loads by the heart during operation of the impeller assembly within the patient.

In another embodiment, a percutaneous heart pump is disclosed that comprises a catheter assembly having a proximal end, a distal end, and an elongate body disposed therebetween. The elongate body can be configured such that the distal end can be disposed inside heart chamber of a human patient while a proximal end is disposed outside the patient. The distal end can comprise an expandable housing being configured to be insertable into a peripheral vessel in a low profile configuration and to be expanded to a larger profile within the patient. The percutaneous heart pump can further include an impeller shaft and an impeller blade extending from the impeller shaft, the impeller shaft being journaled for rotation in the distal portion of the catheter assembly. The expandable housing can comprise an elongate wall structure disposed circumferentially about the impeller blade and extending distally and proximally thereof, the wall being configured to maintain a gap between the blade an inner surface of the wall structure within a selected range over a range of transverse loading corresponding to forces generated during systole and diastole of the heart.

In another embodiment, a catheter assembly for a heart pump is disclosed. The catheter assembly can comprise an impeller shaft and an impeller blade extending from the impeller shaft. The catheter assembly can further include a housing in which the impeller shaft is journaled for rotation, and the housing can have an elongate wall structure, a portion of which is disposed circumferentially about the impeller blade and the impeller shaft. The wall structure can be configured to provide a first stiffness over the impeller blade and a second stiffness greater than the first stiffness at a location proximal of the impeller blade to reduce bending of the housing proximal of the blade.

BRIEF DESCRIPTION OF THE DRAWINGS

A more complete appreciation of the subject matter of the present inventions and the various advantages thereof can be realized by reference to the following detailed description, in which reference is made to the accompanying drawings in which:

FIG. 7 is a perspective view of one embodiment of a catheter body that can be used to house a drive shaft and to convey an infusant to the bearing housing of FIG. 5;

FIG. 9 illustrates one embodiment of an impeller assembly;

FIGS. 9A, 9B-1, 9B-2, 10 and 10A illustrate details of further embodiments of impeller blade;

FIGS. 12, 12A, and 12B are cross-section views similar to that of FIG. 11, illustrating an infusant outflow path;

FIGS. 22-22B illustrate the relative position of an impeller blade and an inner surface of an impeller housing in a steady-state undeflected configuration;

FIGS. 23-23B illustrate the relative position of an impeller blade and an inner surface of an impeller housing in a transient deflected configuration;

FIG. 36 illustrates a wall pattern in a flat configuration that is configured to isolate an impeller region of an impeller assembly from a load such as that illustrated in FIG. 35;

FIG. 36A-D illustrate in greater detail various regions of the wall pattern in FIG. 36;

More detailed descriptions of various embodiments of components for heart pumps useful to treat patients experiencing cardiac stress, including acute heart failure, are set forth below.

DETAILED DESCRIPTION

This application is directed to aspects of heart pumps and components therefor that can be used to treat a patient experiencing cardiac stress, including acute heart failure. Major components of catheter-based pumps that can be applied to a patient percutaneously are described below in Section I. Section II describes distal end features application and performance of heart pumps. In particular, Section II(A) describes structures that facilitate advancement of a heart pump within the vasculature; Section II(B) describes impeller housing configurations that enhance fluid handling performance; and Section II(C) describes stabilizing structures for an impeller housing to control tip gap clearance. Section III illustrates techniques for reducing the complexity and crossing profile of a catheter assembly. Section IV describes features of an impeller assembly for improved performance when subject to operational loads during a heart pumping procedure. Section V discloses embodiments of an impeller housing for enhancing the flow of blood during operation of the impeller. Section VI illustrates methods for use in connection with specific structures of heart pumps.

I. Heart Pump System Overview

Figure 1:
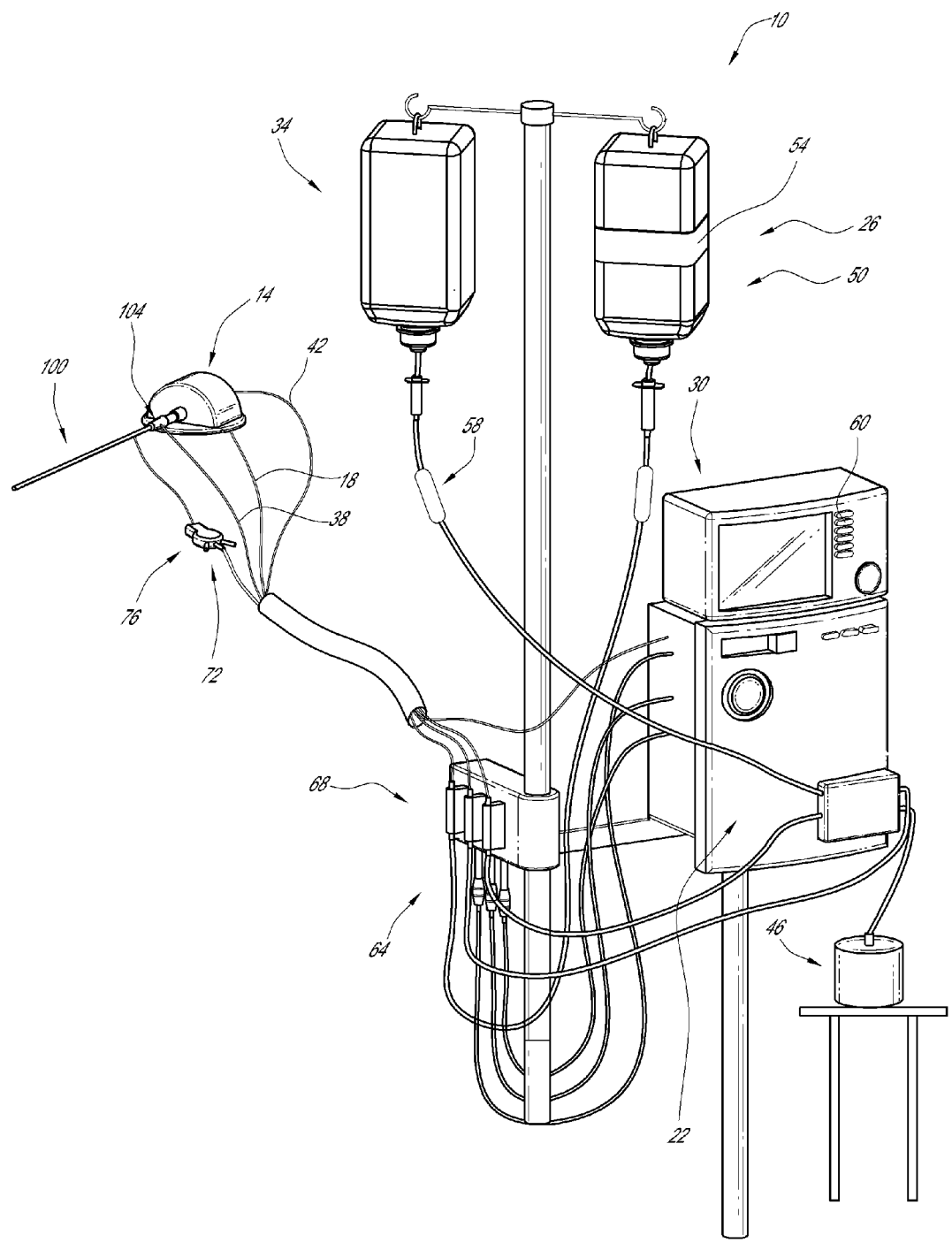
FIG. 1 illustrates one embodiment of a heart pump configured for percutaneous application and operation.
Figure 1A:
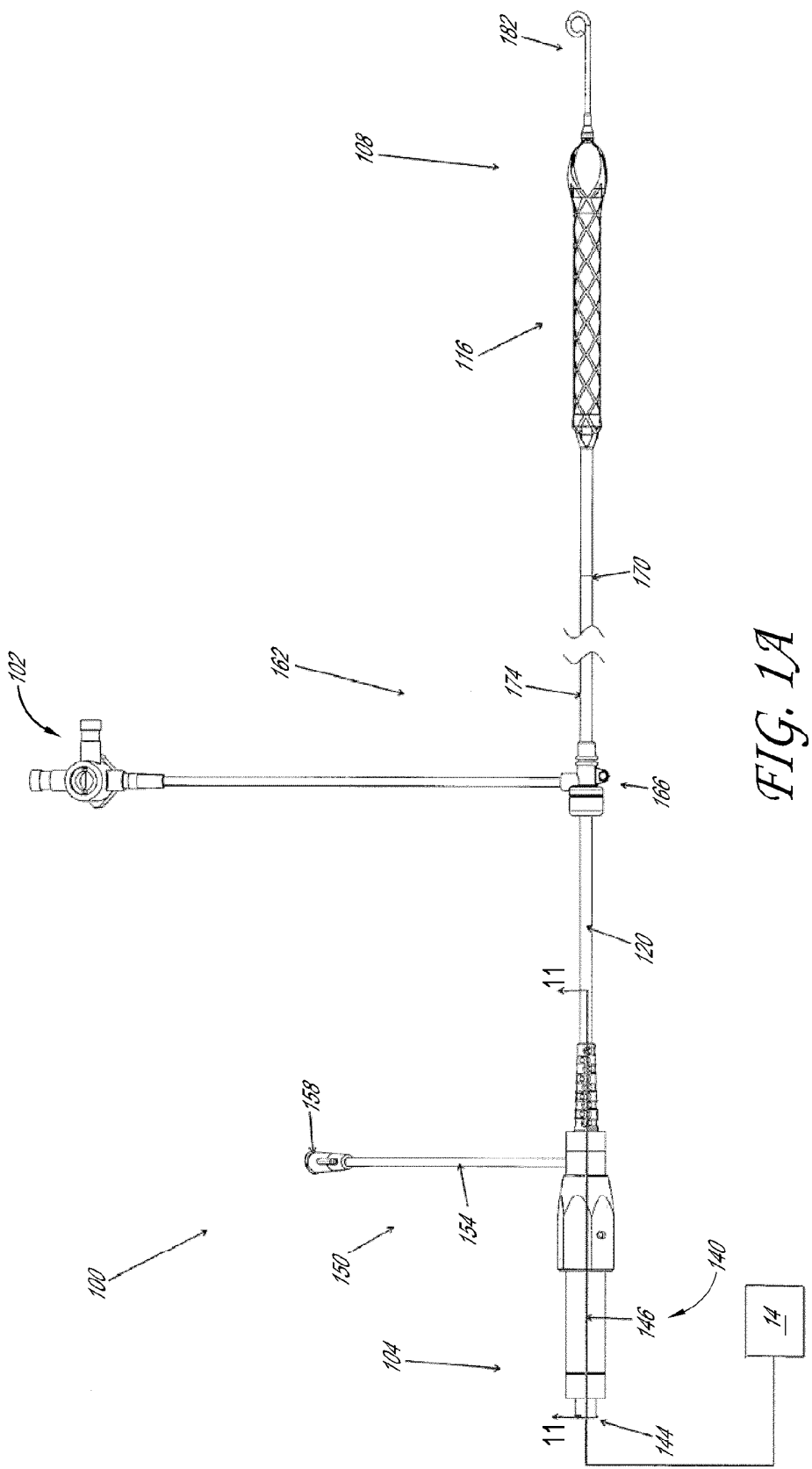
FIG. 1A is a plan view of one embodiment of a catheter assembly adapted to be used with the heart pump of FIG. 1.

FIG. 1 illustrates one embodiment of a heart pump 10 that includes a catheter assembly 100 having a proximal end 104 adapted to connect to a motor 14 and a distal end 108 (as shown in FIG. 1A) adapted to be inserted percutaneously into a patient. The motor 14 is connected by a signal line 18 to a control module 22 that provides power and/or control signals to the motor 14. As discussed further below, the heart pump 10 may have an infusion system 26 and a patient monitoring system 30.

The infusion system 26 can provide a number of benefits to the heart pump 10 which are discussed below. In one embodiment, the infusion system 26 includes a source of infusant 34, a fluid conduit 38 extending from the infusant source 34 to the proximal end 104 of the catheter assembly 100 and a fluid conduit 42 extending from the proximal end of the catheter assembly 100 to a waste container 46. The flow of infusant to and from the catheter assembly 100 can be by any means, including a gravity system or one or more pumps. In the illustrated embodiment, the infusant source 34 includes an elevated container 50, which may be saline or another infusant as discussed below. Flow from the elevated container 50 can be regulated by a pressure cuff 54 to elevate the pressure of the fluid in the container 50 to increase flow or by a pinch valve 58 or by other means.

The patient monitoring system 30 can be used to monitor the operation of the patient and/or the pump 10. For example, the patient monitoring system 30 can include a user interface 60 coupled with a source of data 64. The data source 64 can include one or more patient conditions sensors, such as pressure sensors 68 that are in pressure communication with the patient and/or operating components within the patient. In one embodiment, the pressure sensors 68 fluidly communicate by a conduit 72 that extends between the sensors and a proximal portion of the catheter assembly 100. The conduit 72 can include a plurality of separable segments and can include a valve 76 to enable or disable the pressure communication to the sensors 68.

The heart pump 10 is adapted to provide an acute or other short-term treatment. A short-term treatment can be for less than a day or up to several days or weeks in some cases. With certain configurations the pump 10 can be used for a month or more.

FIG. 1A illustrates one embodiment of a catheter assembly to be used with the heart pump 10. An impeller assembly 116 disposed at the distal end 108 is configured to pump blood proximally or distally through or along a portion of the heart pump 10 to convey blood from one body cavity to another. The impeller assembly 116 can be arranged to pump blood distally, such as in a right heart assist mode to move blood from the right ventricle to the pulmonary artery. Proximal flow is optimal for left heart support to move blood from the left ventricle to the aorta. As discussed below, the heart pump 10 can be used to treat patients with acute heart failure, ST elevation myocardial infarction (STEMI), cardiac arrest, cardiac arrhythmia or other heart maladies. The heart pump 10 also can be used in connection with a surgical treatment to support the patient without providing full cardiovascular bypass. A patient could be supported on the device for longer term with proper controls and design.

One feature that facilitates percutaneous insertion is providing the catheter assembly 100 with a low profile configuration. For example, the distal end 108 of the catheter assembly 100 can be configured to have about an 11 French (approximately 3.5 mm) size in a first configuration for insertion and an expanded configuration, such as up to about 21 French (approximately 7 mm) once in place in the body. The larger size facilitates greater flow rates by the impeller assembly 116 as discussed below.

The catheter assembly 100 is configured to enable the distal end 108 to reach a heart chamber after being inserted initially into a peripheral vessel. For example, the catheter assembly 100 can have a suitable length to reach the left ventricle and sufficient pushability and torquability to traverse the intervening vasculature. The catheter assembly 100 may include a multilumen catheter body 120 that is arranged to facilitate delivery and operation of an impeller of the impeller assembly 116. Further details concerning various embodiments of the catheter body 120 are illustrated in FIGS.

7-7B and described in more detail in U.S. Provisional Application No. 61/430,129, filed Jan. 5, 2010.

A drive system is provided to drive an impeller within the impeller assembly 116. The drive system includes the motor 14 and a drive controller, which can be integrated into the control module 22. Although the motor 14 may be configured to be disposed outside the patient, some structures and assemblies described herein could be incorporated into a system in which a motor is miniaturized sufficiently to be inserted into the patient in use, including into the vasculature.

Figure 11:
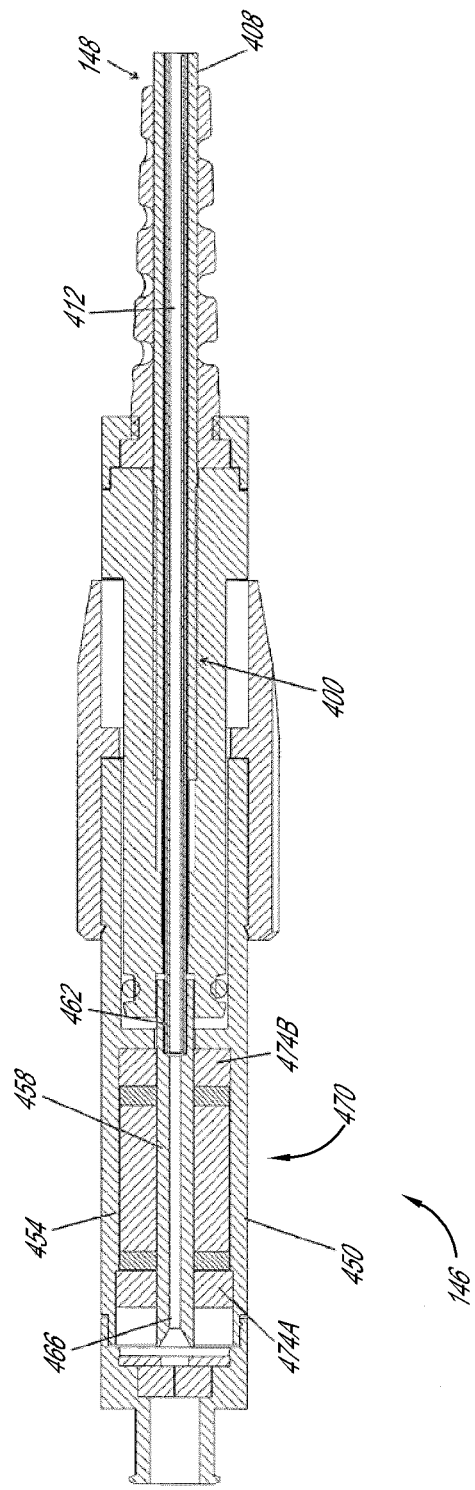
FIG. 11 is a cross-sectional view of a proximal portion of the catheter assembly, taken through the section plane 11-11 on FIG. 1A.

A torque coupling system is provided for transferring torque from the motor 14 to the impeller assembly 116. The torque coupling system is discussed further in U.S. Provisional Application No. 61/430,129, filed Jan. 5, 2010, but in general can include a mechanical or magnetic interface disposed between the motor 14 and a drive assembly illustrated in FIG. 11 that is disposed at the proximal end 104 of the catheter assembly 100. The drive assembly is coupled with a proximal end of an elongate drive shaft 148 in one embodiment. The drive shaft 148 extends between the drive assembly 146 and the impeller assembly 116. A distal portion of the drive shaft 148 is coupled with the impeller assembly 116 as illustrated below in connection with one embodiment illustrated in FIGS. 4A and 4B. FIG. 11 shows one manner of coupling the proximal end of the drive shaft 148 with the drive assembly 146.

FIG. 1A shows an infusion inflow assembly 150 that can form a part of the infusion system 26 (see FIG. 1). The infusion in the assembly 150 is provided adjacent the proximal end 104 in one embodiment. The infusion system 26 is configured to convey one or more fluids therein in connection with operation of the impeller assembly 116 or the conducting of the treatment. In one embodiment, an infusant, e.g., a medication or a lubricating fluid, such as saline or other beneficial medium, is conveyed distally along the pump, e.g., within the catheter body 120, toward operating components adjacent the distal end 108. The infusant can include lubrication fluids such as glucose or other biocompatible lubricants. The infusion inflow assembly 150 includes a catheter body 154 having a luer or other suitable connector 158 disposed at a proximal end thereof and an inflow port in fluid communication with one or more lumens within the catheter assembly 100. A lumen extending through the catheter body 154 is adapted to be fluidly coupled with a fluid source connected to the connector 158, to deliver the fluid into the catheter assembly 100 and through one or more flow paths as discussed below in connection with FIGS. 4A, 4B, and 7-7B.

As discussed further below in connection with FIGS. 1A and 12, the infusion system 26 may also include an outlet positioned at a location that is outside the patient when the heart pump 10 is in use, such that at least a portion of the infusant can be removed from the heart pump 10 and the patient during or after the treatment. An infusant outlet assembly can include a lumen, e.g., within the fluid conduit 42, that is fluidly coupled with an infusant return flow path in the catheter body 120 through a proximal end mechanical interface, for example.

The catheter assembly 100 can also include a sheath assembly 162 configured to constrain the impeller assembly 116 in a low profile configuration in a first state and to permit the impeller assembly 116 to expand to the enlarged configuration in a second state. The sheath assembly 162 has a proximal end 166, a distal end 170, and an elongate body 174 extending therebetween. The elongate body 174 has a lumen extending between the proximal and distal ends 166, 170. The lumen is configured to be slidably disposed over the catheter body 120. The arrangement permits the sheath assembly 162 to be positioned between an advanced position corresponding to the low profile configuration and a retracted position corresponding to the enlarged configuration. In some embodiments, a luer 102 or other suitable connector is in fluid communication with the proximal end 166 of the sheath assembly 162. The luer 102 can be configured to deliver fluids to the catheter assembly 100, such as priming fluid, infusant, or any other suitable fluid.

FIG. 1A illustrates a retracted position, in which the distal end 170 of the elongate body 174 is at a position proximal of the impeller assembly 116. In an advanced position, the distal end 170 of the elongate body 174 is positioned distal of at least a portion of the impeller assembly 116. The sheath assembly 162 can be configured such that distal advancement of the distal end 170 over the impeller assembly 116 actuates the impeller assembly 116 to a low profile configuration, e.g., causing a change from the second state to the first state, as discussed above. Although shown in FIGS. 4A & 4B as a single layer, the elongate body 174 can include a multilayer construction.

Figure 2:
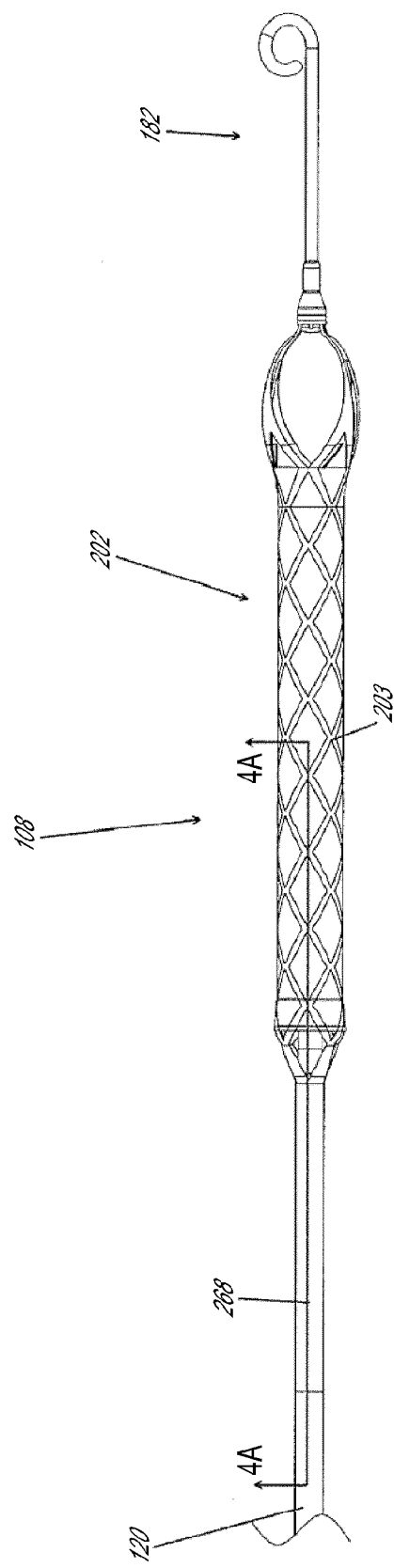
FIG. 2 is a detail view of a distal portion of the catheter assembly illustrated in FIG. 1A.
Figure 3:
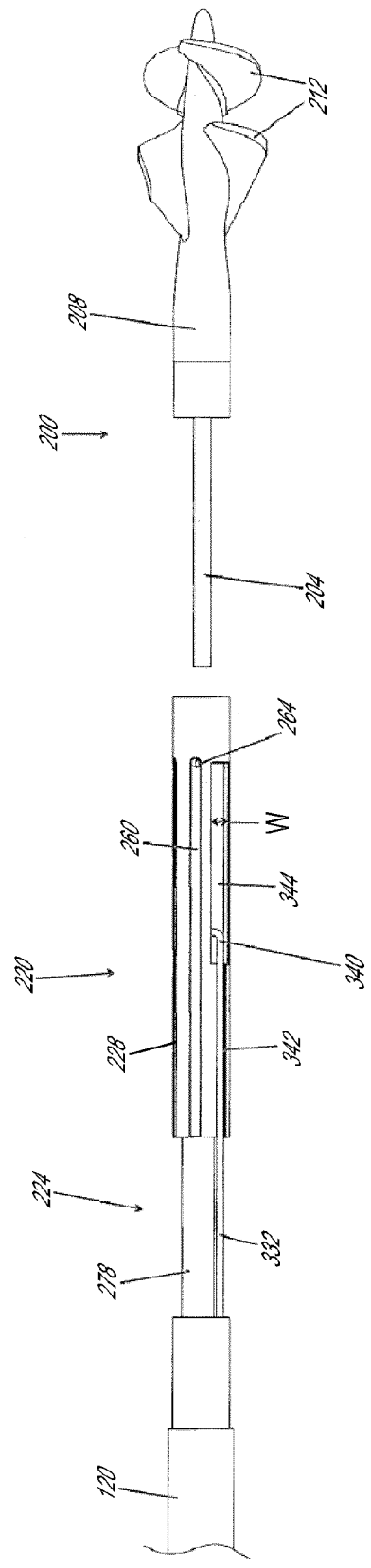
FIG. 3 is an exploded view of a portion of an impeller assembly of the catheter assembly of FIG. 1A.

FIGS. 1A and 2 show that a housing 202 is disposed at the distal end 108. The housing 202 can be considered part of the impeller assembly 116 in that it houses an impeller and provides clearance between the impeller and the anatomy to prevent any harmful interactions therebetween. The housing 202 and the impeller are also carefully integrated to maintain an appropriate flow regime, e.g., from distal to proximal within the housing. FIGS. 2, 21A-B, 22-23, and 35A-41 show that in some embodiments the housing 202 includes a cage or mesh structure 203 of filaments that extend axially along the housing and that wrap circumferentially around a central area of the housing in which an impeller of the impeller assembly 116 is disposed. The mesh structure 203 can take any suitable form, such as being constructed to prevent kinking upon delivery or to control the spacing between a radially outer edge of an impeller and the housing 202, as discussed below. The housing 202 forms a cannula through which blood flows during use of the system.

Figure 31:
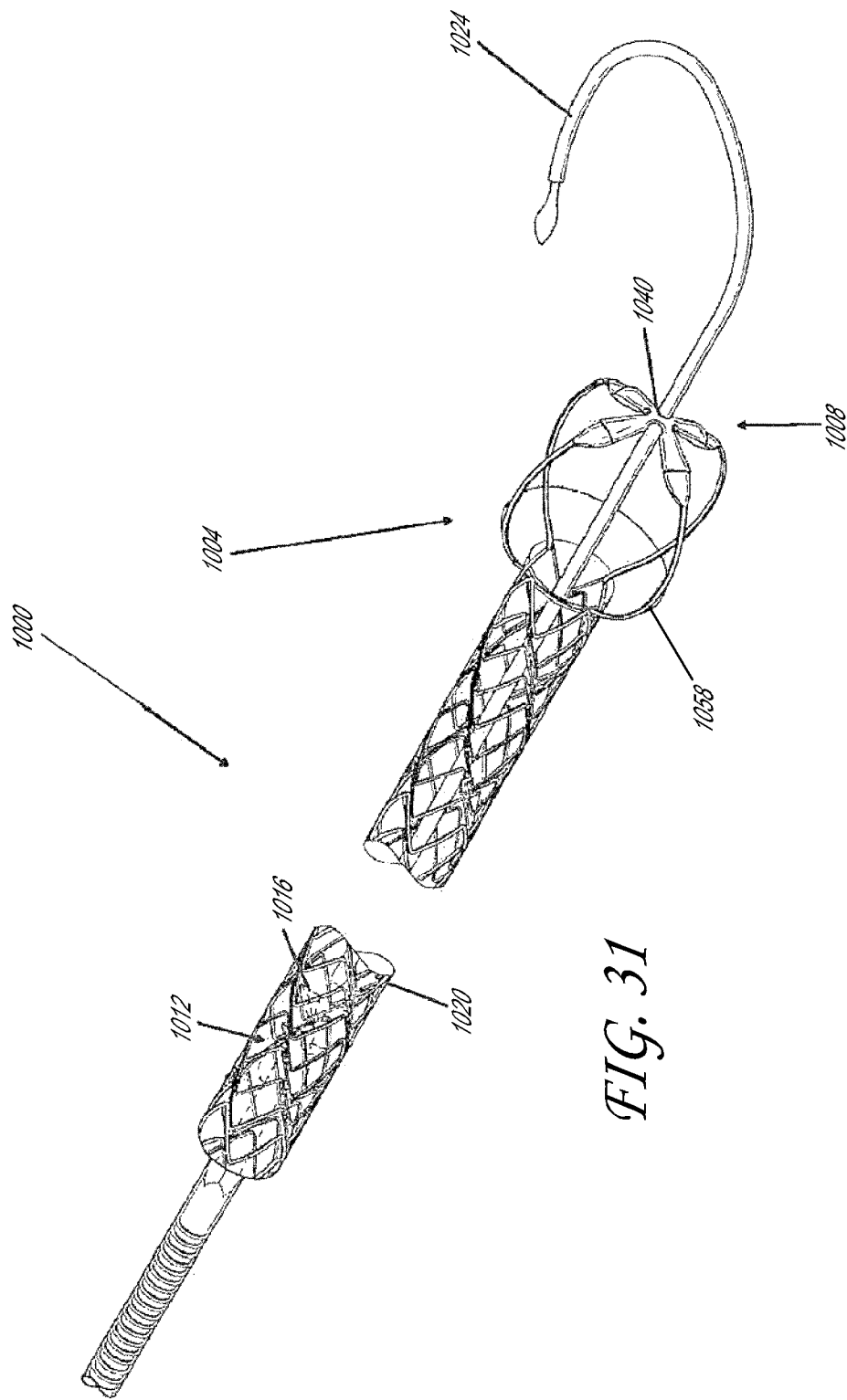
FIG. 31 show the catheter assembly of FIG. 30 in an expanded configuration with a guidewire in position.
Figure 32:
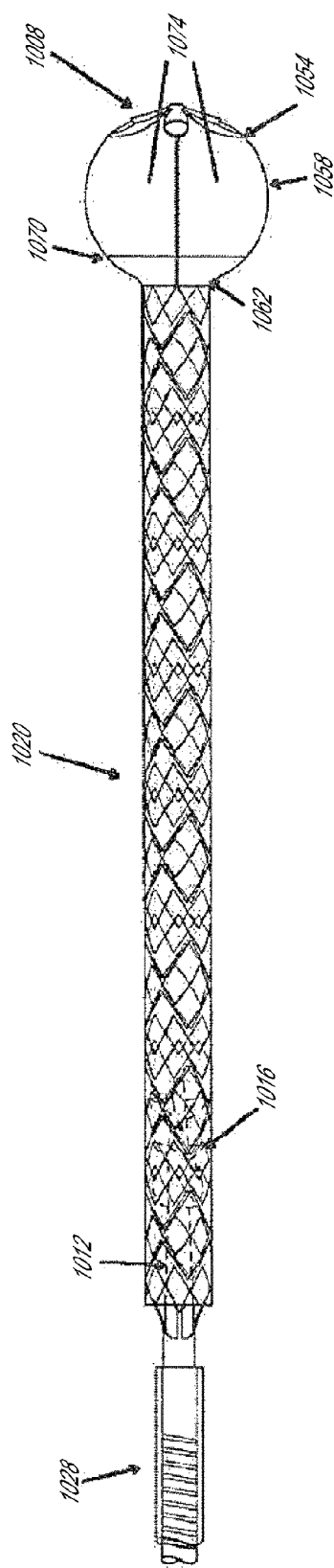
FIG. 32 is a plan view of the catheter assembly of FIG. 30 in an expanded configuration with the guidewire removed.
Figure 33:
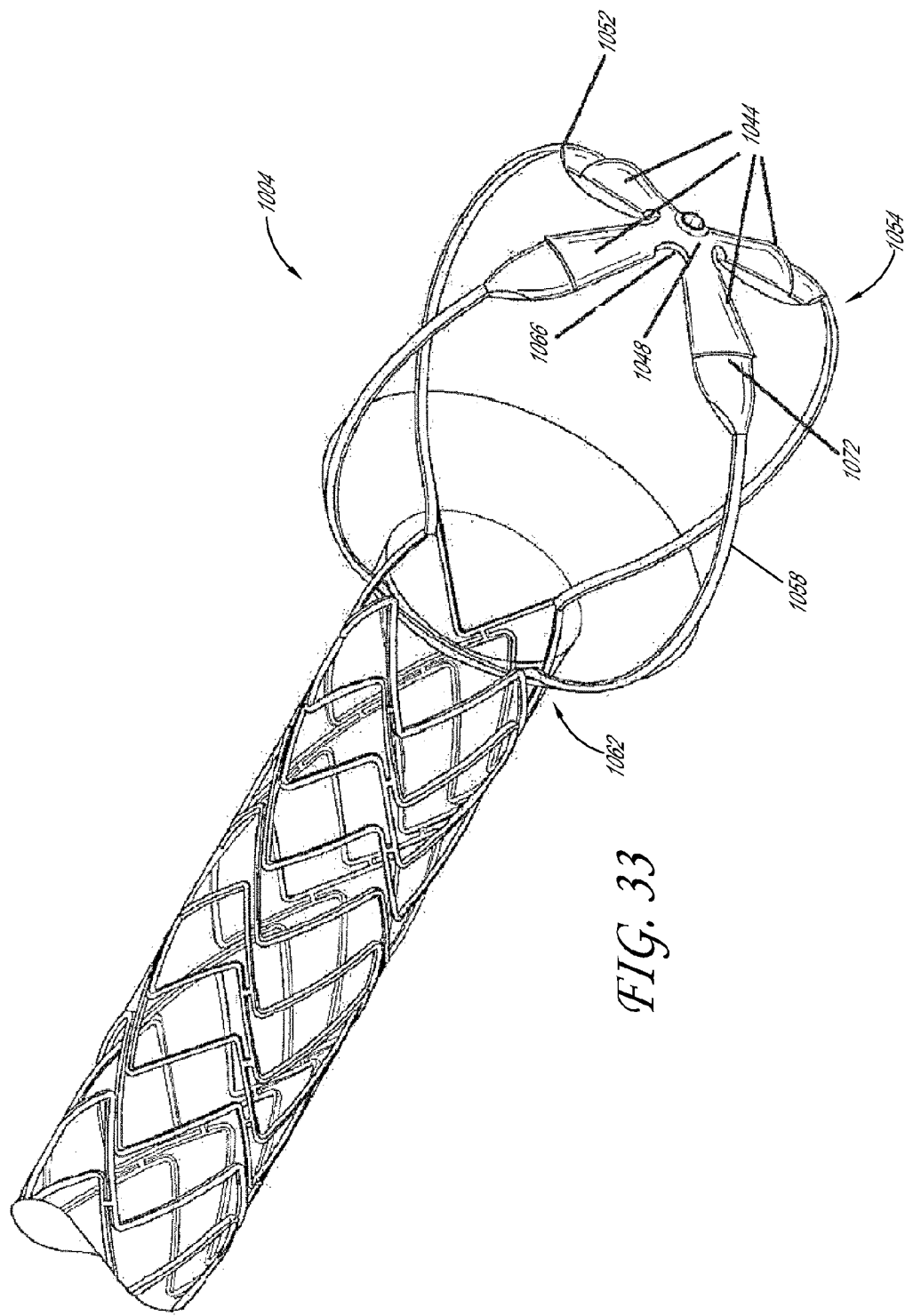
FIG. 33 is a detailed view of the distal end of an impeller assembly showing details of an expandable tip.

If the catheter assembly 100 is used for left heart support, the heart pump 10 and intake 202A is provided at a distal end of the housing 202. The intake can be configured to remain open in operational conditions such as by having a shape that reduces or eliminate suck-down (e.g., suction causing the inlet to get stuck against wall surface) and to keep the inlet open. For example, as shown in FIGS. 31-33, various embodiments of the housing can be arranged with a bulbous shape (e.g., round, spherical, egg-shaped, oblate spheroidal, or any other shape that includes an enlarged portion having a non-linear curved outer surface) to prevent heart tissue from being drawn into the inlet to interfere with operation of the heart pump 10. The shape also is useful to position the inlet from the wall.

FIGS. 1A and 2 also show that the distal end 108 of the catheter assembly 100 includes an atraumatic tip 182 disposed distal of the impeller assembly 116 in one embodiment. The atraumatic tip 182 can have an arcuate configuration such that interactions with a patient's internal tissues are controlled and do not cause trauma thereto. The tip 182 can take any suitable shape, which can vary depending on the degree of curvature of the tip. The tip is designed to be atraumatic so that after retraction of the guidewire, when the tip is left inside, for example, a ventricle, it cannot cause injury or trauma to the inner wall or endocardial surface of the ventricle resulting from motion of the ventricle.

Figure 13A:
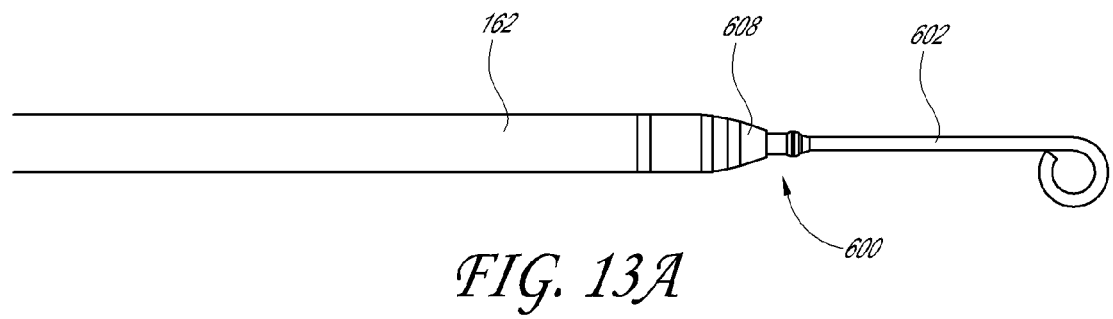
FIGS. 13A-13B illustrate side views of various embodiments of the flexible tip assembly.
Figure 13B:
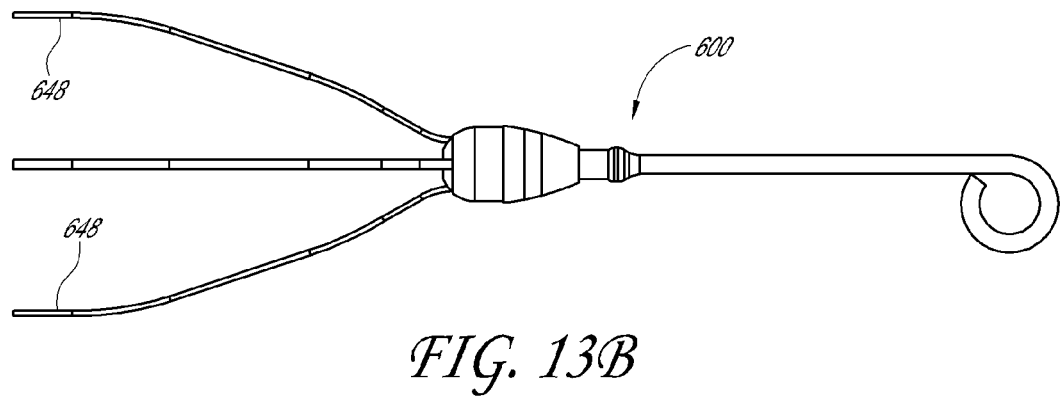

For example, the atraumatic tip 182 can include a 180° bend, wherein the distal-most end of the tip 182 is generally parallel to the non-arcuate portion of the atraumatic tip 182, but extending in the opposite direction (e.g., a j-tip). In other embodiments, the distal-most end of the tip 182 can be generally perpendicular to the non-arcuate portion of the atraumatic tip 182, for example as illustrated in FIG. 19A, or at an angle between about 90° and about 180°, for example as illustrated in FIGS. 13A-B. In yet another embodiment, the distal-most end of the tip 182 can include a 360° bend, wherein the distal-most end of the tip 182 is generally parallel to the non-arcuate portion of the atraumatic tip, while extending in generally the same direction. In some embodiments, the arcuate portion of the tip 182 can be coiled greater than 360°. The latter two embodiments may herein be referred to as a pigtail tip.

FIGS. 3-12B illustrate additional features of the heart pump, as discussed in U.S. Provisional Application No. 61/430,129, filed Jan. 5, 2010 and as set forth in the appendix below.

II. Heart Pump Distal End Configurations

FIGS. 13-25 illustrate a variety of heart pumps embodiments that have advantageous distal or working end arrangements. These embodiments provide atraumatic distal tips and coupling of the same with distal portions of a catheter based heart pump. These embodiments also relate to particularly useful constructions of impeller housings that are able to collapse and expand as needed and also interact with blood cells in a minimally traumatic way. These embodiments also provide for secure engagement of an impeller housing with a proximal portion of the heart pump. Features of these embodiments can be interchanged and combined to arrive at different embodiments within the scope of this application.

A. Atraumatic Flexible Tip Structures

As discussed above, the heart pump 10 is configured as a catheter device that will be placed within the heart after being advanced through the vasculature. As such the distal portion of the pump 100 should be as minimally traumatic as possible to the anatomy to be encountered. As discussed further below, the connection of the distal end of the housing 202 to the tip 182 can be achieved by advantageous mechanical arrangements.

1. Interlock Configurations for Joining Flexible Tip to Impeller Housing

FIGS. 13-19A illustrate a variety of embodiments for connecting the atraumatic tip 182 to the distal end of the impeller housing 202. FIGS. 13A-13B illustrate another embodiment of the flexible tip assembly 600 and how it can be attached to the impeller housing 202. FIG. 13A shows the distal end of an embodiment of the pump 100, including the flexible tip assembly 600, and the sheath assembly 162 disposed proximally thereof. The embodiment of FIG. 13A also shows a hub 608 and a flexible member 602. FIG. 13B shows flexible tip assembly 600 and distal members 648 of the impeller housing 202.

Figure 14:
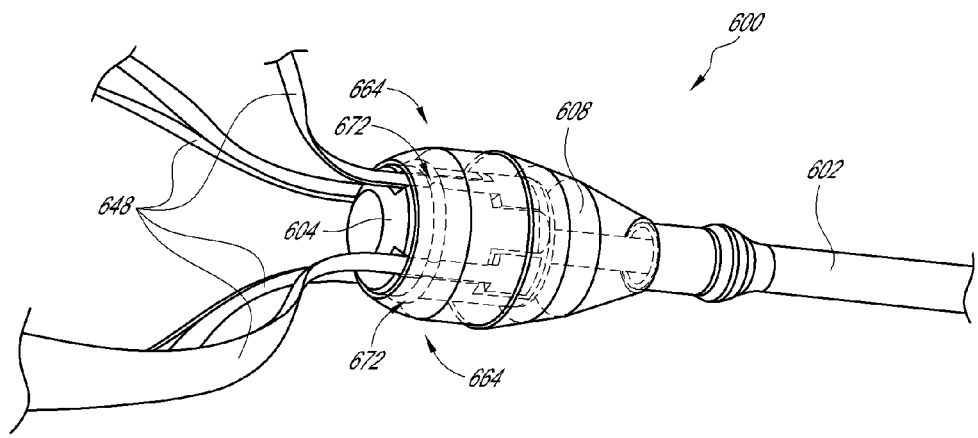
FIG. 14 is a perspective view of an embodiment of a flexible tip assembly that can be used in a heart pump.
Figure 15:
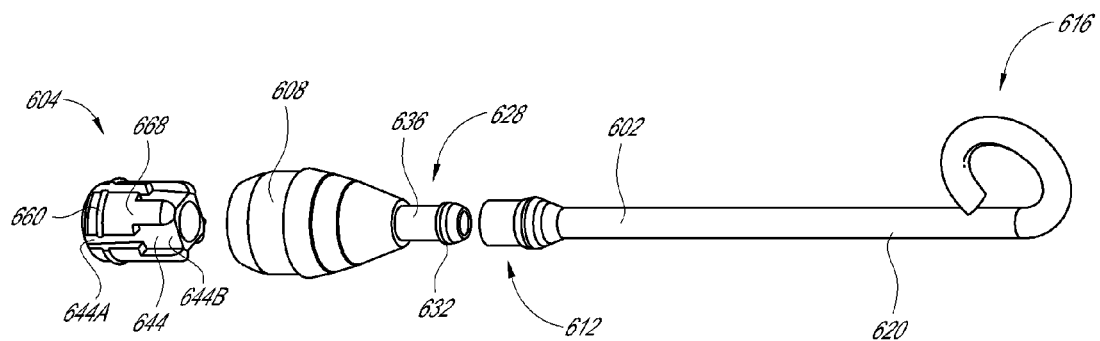
FIG. 15 is an exploded view of the flexible tip assembly of FIGS. 13A-B.

The embodiments of FIGS. 14 and 15 include a flexible tip assembly 600 having a locking arrangement for coupling the impeller housing 202 to the flexible member 602. The locking arrangement can be configured to lock or secure a component of the impeller housing 202 between two components of the tip assembly 600. These arrangements are sometimes referred to herein as an interface lock because in some cases they secure a distal structure of the housing at an interface between two separable structures. In this context, separable includes arrangements that can be assembled and disassembled rather than unitary arrangements.

The flexible tip assembly 600 includes a core member 604 and the hub 608. The flexible member 602 can take any suitable form, but as illustrated in FIG. 15 may include a proximal portion 612, a distal portion 616, and an elongate body 620 extending therebetween. The distal portion 616 can take any suitable form, but may be made atraumatic, such as by including an arcuate portion as shown in FIG. 15. The proximal portion 612 may be configured to be coupled with a distal portion of the hub 608. For example, the proximal portion 612 can include a flared body that is adapted to be advanced onto the hub 608.

The hub 608 is configured to be disposed between the flexible member 602 and the housing 202. The hub 608 may include a distal portion 628 configured to be coupled with a proximal portion 612 of the flexible member 602. For example, an enlarged structure 632 is disposed at the distal end of a tubular body 636 in one embodiment. The enlarged structure 632 can be a barb located at the distal end of the hub 608. The proximal end of the hub 608 can include a recess 640 configured to receive the core member 604 therein.

In one embodiment, the core member 604 and the hub 608 are configured to secure therebetween the distal portion of impeller housing 202. FIGS. 14 and 15 show that in one arrangement a recess 644 is provided that is configured to receive a plurality of distal members 648 of the impeller housing 202. The recess 644 can be provided with a profile with a shape similar to the shape of the distal member 648. The core member 604 can be provided with a plurality of recesses dispose in an outer surface thereof. In one embodiment, each of the recesses 644 is provided with a shape that matches a shape of the distal end of a corresponding one of the members 648.

FIG. 14 illustrates one embodiment in which a T-shaped configuration is provided at the distal end of each of the members 648. Each of the recesses 644 similarly is provided with a T-shaped configuration. In one arrangement the recess 644 comprises a narrow proximal portion 644A and a wide distal portion 644B. The narrow proximal portion 644A is configured to receive a slender length of the members 648 and the wide distal portion 644B is configured to receive a distal-most end portion of the member 648, which has a transverse width that is greater than the width of the slender length portion of the member 648.

In one embodiment the core member 604 and the hub 608 are configured to be securely coupled together such that the members 648 of the impeller housing 202 are secured within the flexible tip assembly 600. FIGS. 14 and 15 illustrate that in one arrangement, a plurality of members 648 is disposed about the perimeter of the distal portion of the impeller housing 202. In the illustrated embodiment, there are four members 648 at the distal end of the housing 202. Each of the four members 648 can be received within a corresponding recess 644 of the core member 604. Thereafter the core member 604 along with the distal ends of the four members 648 disposed in the recesses 644 can be inserted into the recess 640 of the hub 608.

Securement of the core member 604 within the hub 608 can be provided by any suitable technique. For example, as illustrated in FIGS. 14 and 15, a proximal portion of the core member 604 can be provided with an engagement feature 660 configured to couple with a corresponding engagement feature 664 disposed on the hub 608. In the illustrated embodiment, the engagement feature 660 disposed on the core member 604 comprises an arcuate protrusion extending away from a side surface 668 of the core member 604. In the illustrated embodiment, the corresponding engagement feature 664 disposed on the hub 608 includes an arcuate recess 672 disposed within the recess 640 of the hub 608. The engagement feature 660 and recesses 640, 672 are more clearly shown on FIG.

16A, which is discussed in more detail below. In one embodiment, the arcuate protrusion that forms a least a part of the engagement feature 660 can include a plurality of protrusions disposed about the core member 604. In various embodiments, protrusions are disposed at least on opposite sides of the core member 604. In one embodiment the engagement feature 660 substantially surrounds the outer surface of the core member 604. In one embodiment, the recess 672 comprises a circumferential channel surrounding the recess 640 of the hub 608.

In one embodiment, a lumen 676 (shown in FIG. 16A) extends through at least one of the components of the flexible tip assembly 600. In some embodiments, the lumen 676 extends from the proximal end of the core member 604 to the distal end of the flexible member 602. The lumen 676 enables advancement of a guide wire through the pump, e.g., from the distal end of the elongate body 620 into the impeller housing 202.

Figure 16A:
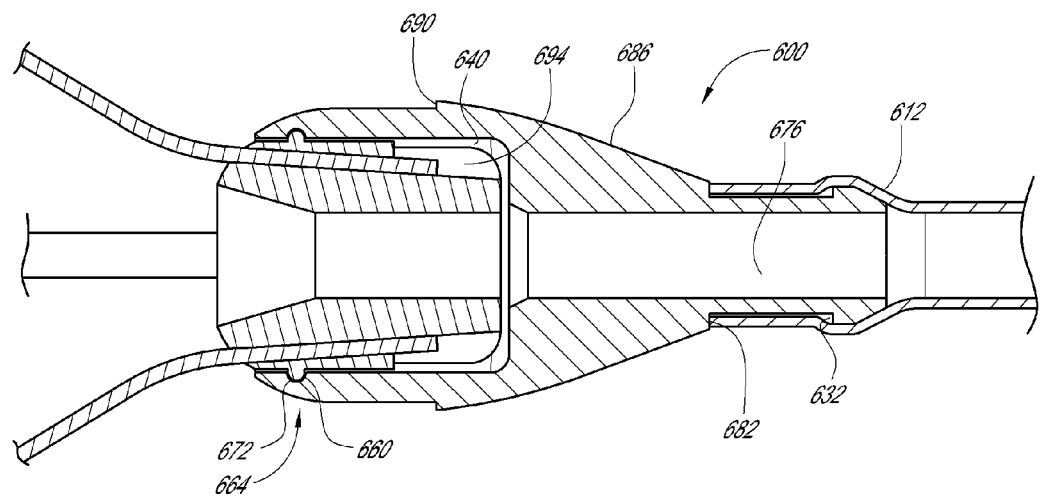
FIG. 16A illustrates another embodiment of a flexible tip assembly.

FIG. 16A shows the proximal end of the elongate body 602 advanced over the enlarged structure 632 of the hub 608. The proximal end of the elongate body 602 is advanced into engagement with a distal-facing shoulder 682 of the hub 608. A length of the hub 608 extending proximally from the distal-facing shoulder 682 of the hub has a progressively larger outer perimeter, forming a dilating structure 686. The dilating structure 686 is disposed between the distal facing shoulder 682 and a proximal-facing shoulder 690 of the hub 608. In the embodiment of FIG. 16A the proximal facing shoulder 690 is disposed proximal of the distal end of the recess 640.

FIGS. 13A and 16A shows that the proximal-facing shoulder 690 is configured to abut against a distal end of the sheath assembly 162. This configuration provides a generally smooth transition between the distal-facing shoulders 682 and the proximal-facing shoulder 690 as well as at the interface between the sheath assembly 162 and the proximal-facing shoulder 690. In one embodiment, a smooth transition is provided along the entire length from the distal facing shoulders 682 to the proximal facing shoulders 690.

In some embodiments, a securement device 694 can be provided for coupling one or more of the members 648 to the core member 604 or within the hub 608. In some variations, the securement device 694 can be used to supplement the locking arrangement between the core member 604 and the hub 608. In other embodiments, a mating arrangement is provided between the distal end of the members 648 and a corresponding recess in at least one of the core member 604 and the hub 608. The mating arrangement can include the recess 644 as discussed above. In another arrangement the recess 644 can be eliminated and the securement device 694 can be relied upon primarily for securing the member 648. The securement device 694 can comprise an adhesive layer disposed over the distal end portion of one or more the members 648. The securement device 694 can extend distally from the distal end of one or more of the member 648 onto the outer surface of the core member 604.

Figure 16:
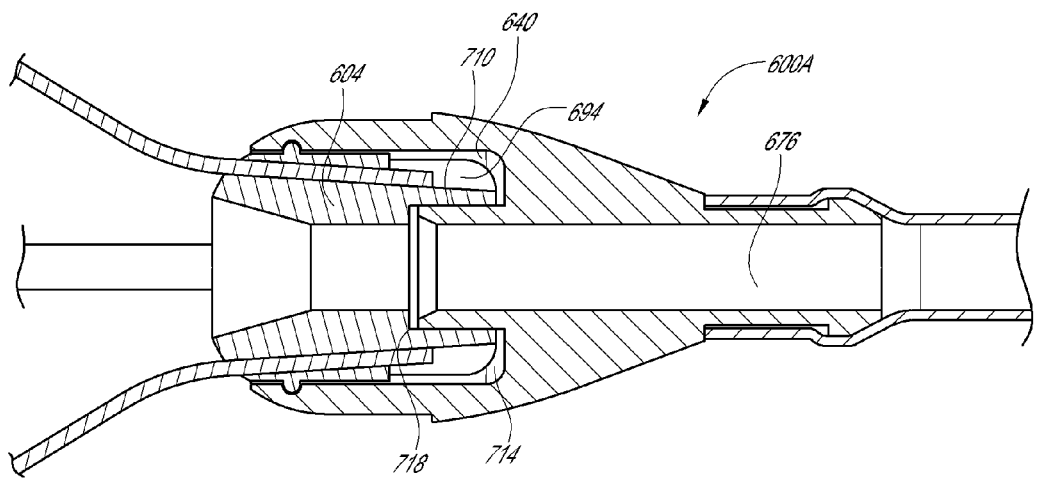
FIG. 16 is a cross-sectional view of a portion of another embodiment of a flexible tip assembly in which a barrier structure is provided for separating components of an interlocking assembly from a lumen of the tip assembly.

FIG. 16 illustrates another embodiment that is similar to embodiment of FIGS. 13A/B-16A except as set forth below. FIG. 16 illustrates a flexible tip assembly 600A that is configured to provide a barrier to isolate certain components of the flexible tip assembly 600 from the lumen 676. For example, in some embodiments where a secondary securement device 694 includes an adhesive, it may be advantageous to provide an additional degree of separation between the adhesive and any blood disposed near or within the lumen 676.

In one embodiment, a distal portion of the recess 640 includes an annular protrusion 710. The annular protrusion 710 can have a portion of the lumen 676 extending therein. A well 714 is disposed around the annular protrusion 710 in one embodiment. The well 714 can be configured as an annular recess extending distally of the proximal end of the annular protrusion 710. The well 714 is configured to receive at least a portion of the core member 604. The volume within the well 714 is sufficient to also accommodate at least a distal portion of the secondary securement device 694 which, as discussed above, can be an adhesive.

A distal portion of the core member 604 comprises a recess 718 configured to receive the annular protrusion 710. In various embodiments the interface between the annular protrusion 710 and the recess 718 is configured to minimize or prevent any adhesive or other portion of the secondary securement device 694 from entering the lumen 676. In other aspects, the flexible tip assembly 600A is similar to the flexible to assembly 600.

Figure 17:
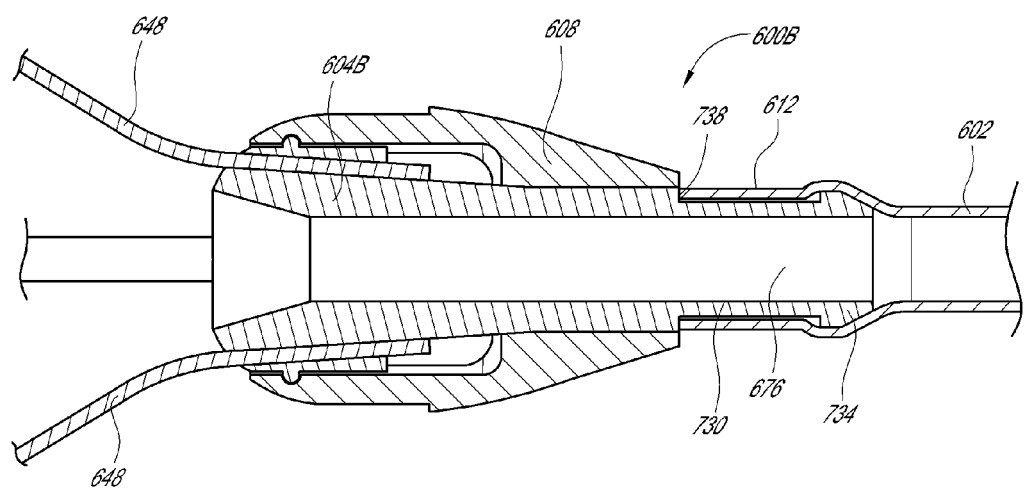
FIG. 17 is a cross-section view of a portion of another embodiment of a flexible tip assembly that is configured to resist detachment of components thereof due to opposed forced being applied at opposite ends of the flexible tip assembly.

FIG. 17 illustrates a flexible tip assembly 600B as similar to the flexible tip assembly 600 except as set forth below. The flexible tip assembly 600B is configured to minimize the likelihood of the hub 608 becoming decoupled from the core member 604B, for example if forces in opposite directions are applied to the flexible member 602 (e.g., distally directed) and the members 648 (e.g., proximally directed) or a portion of the impeller housing 202. In one embodiment, this benefit is achieved by modifying the core member 604B to enable the core member 604B to directly connect to the proximal portion 612 of the elongate body 620. The core member 604B can have an elongated distal portion 730 that extends distally of the distal end of the hub 608. In one embodiment, elongated distal portion 730 comprises an enlarged portion 734 in the distal end there of, a distal facing shoulder 738, and the lumen 676 extending therethrough. The proximal portion 612 of the elongate body 620 can be received over the enlarged portion 734 and advanced into engagement with the distal facing shoulder 738. Securement of the core member 604B within the hub 608 is similar to that described in connection with FIG. 13A/B-16A.

Figure 18A:
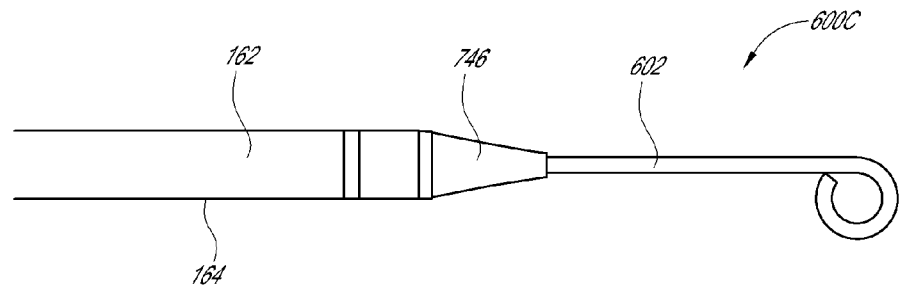
FIGS. 18A-18B illustrate another embodiment of a flexible tip assembly having an extended dilating structure.
Figure 18B:
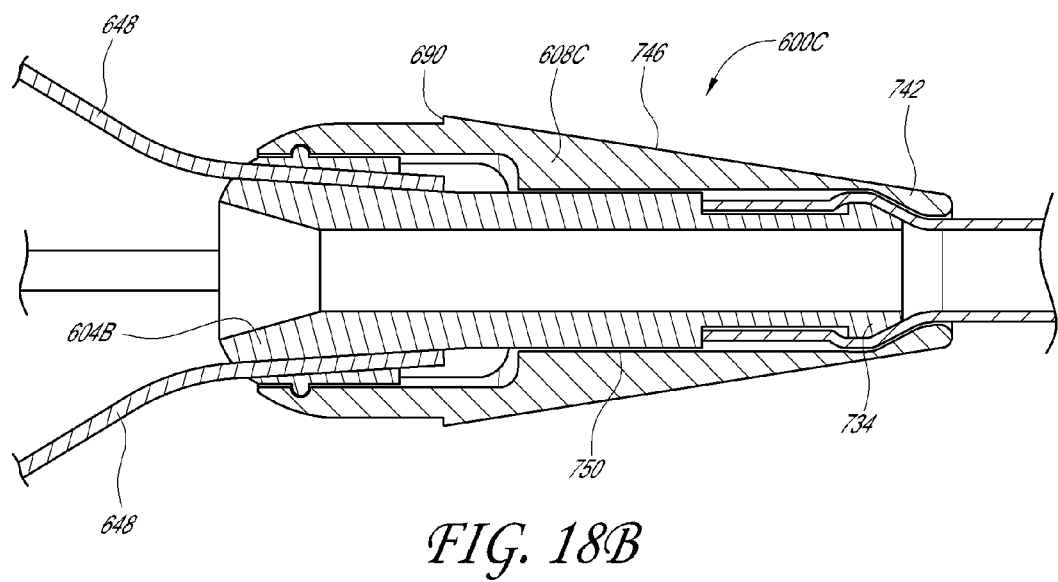

FIGS. 18A-18B illustrate an embodiment of a flexible tip assembly 600C that is similar to the embodiment of FIG. 17 except as set forth below. A hub 608C having an elongated distal portion is provided. The elongated distal portion can comprise a distal end 742 that is disposed distally of the enlarged portion 734 and the core member 604B when the flexible tip assembly 600C is assembled. The hub 608C includes a tapered outer surface 746 extending from the distal end 742 toward the proximal facing shoulder 690. The hub 608C includes a bore 750 extending from the proximal end thereof to the distal end 742. The bore 750 is configured with different widths at different longitudinal positions. For example, the bore 750 can be stepped such that it has a smallest diameter at or adjacent to the distal end. The diameter can be larger at the location where the enlarged portion 734 of the core member 604B is disposed when the tip assembly 600C is assembled. By decreasing the width of the bore 750 at or distal to the enlarged portion 734 the hub 608C can impede axial, e.g., distal motion of the core member 604B relative to the hub 608C. The diameter of the bore 750 can be substantially constant along the length between the location where the enlarged portion 734 is disposed and the location where a further enlargement of the bore 750 is provided. The region of further enlargement can be configured to receive a portion of the core member 604B that couples with the members 648 of the impeller housing 202.

FIG. 18A shows a transition from the flexible member 602 to the tapered outer surface 746 and from the tapered outer surface to the outer surface 164 of the distal portion of the sheath assembly 162. Such tapering can be advantageously configured to facilitate advancement of a percutaneous heart pump within the body. The outer surface 746 can act as a dilating structure in use. In certain embodiments, the flexible member 602 is eliminated and the complexity of the distal section can be reduced by integrating a dilating structure into a distal portion of the housing 202 as discussed in connection with FIGS. 30-34 below.

Figure 19:
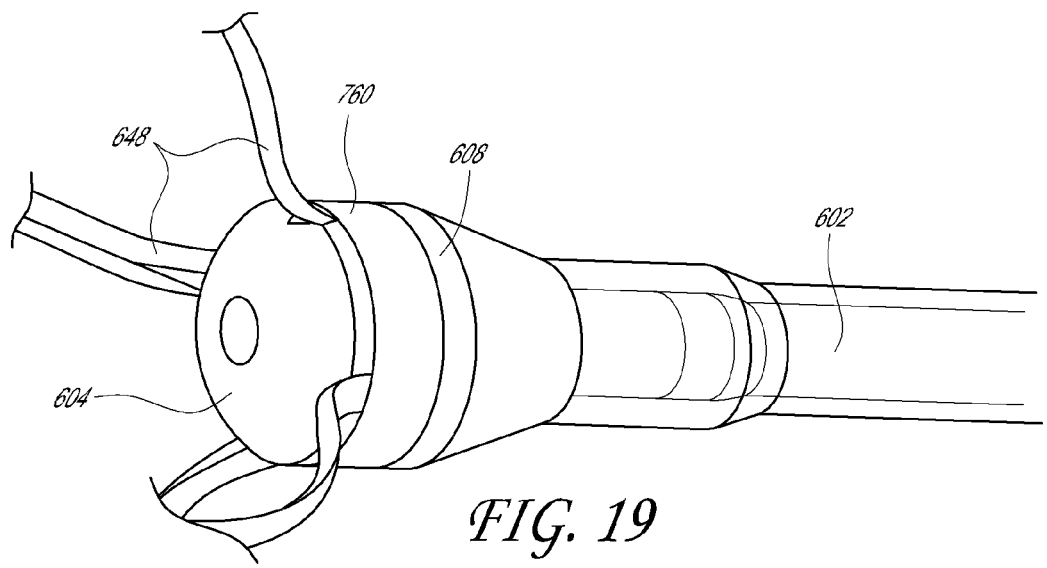
FIG. 19 is a perspective view of another embodiment of a flexible tip assembly.
Figure 19A:
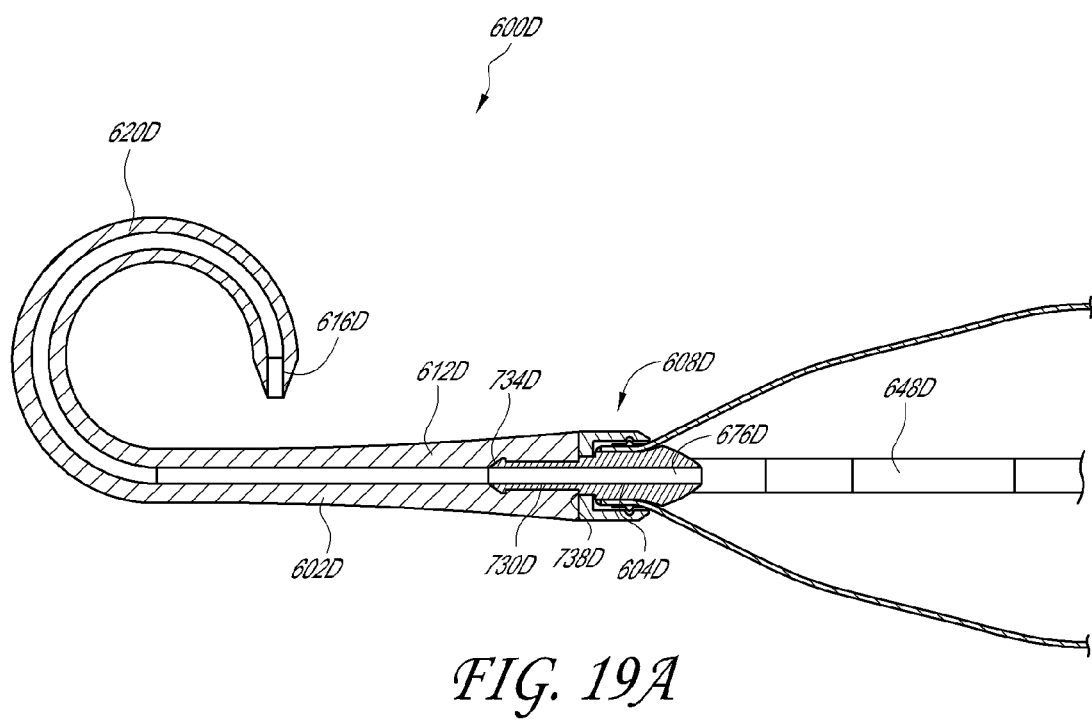
FIG. 19A is a perspective view of another embodiment of a flexible tip assembly.

FIG. 19 shows another embodiment of a flexible tip assembly in which a plurality of members 648 of an impeller housing 202 are joined at their distal ends by a circumferential structure 760. In one variation, the circumferential structure 760 includes an arcuate structure extending at least between each of the members 648. The arcuate structure can be a ring that can be joined to each of the members 648 or a unitary ring-like arrangement bridging the distal ends of the members. In one embodiment, the circumferential structure 760 is disposed between the core member 604 and the hub 608. In one embodiment, the circumferential structure 760 is received within a recess formed in the outer surface of the core member 604. The circumferential structure 760 can enhance the security of the distal ends of the member 648. In particular, by coupling the distal ends of the member 648 together, twisting or movement due to torque on the members 648 or the impeller housing 202 can be reduced or eliminated.

Another advantage of the embodiment of FIG. 19 is that a rounded surface on the proximal portion of the core member is provided facing proximally toward the impeller housing 202. This rounded surface is one arrangement that can reduce the tendency of thrombogenesis at the proximal portion of the core member or adjacent to the impeller housing 202. Like other features discussed herein, this feature can be combined with those of other embodiments to provide additional embodiments.

FIG. 19A illustrates another embodiment of a flexible tip assembly 600D. The flexible tip assembly 600D can include a hub 608D, a core member 604D, and a flexible member 602D. In some embodiments, the hub 608D can have an increasing outer profile (e.g., outer diameter) along its length. In other embodiments, the hub 608D can have a generally constant outer profile (e.g., outer diameter) along its length. The hub 608D can at least partially enclose the core member 604D, described further below. The hub 608D can have one or more other characteristics of the hubs of the other flexible tip assemblies described herein. The hub 608D can be coupled with a proximal end of the flexible member 602D. As illustrated in FIG. 19A, the hub 608D can be coupled with the flexible member 602D through the core member 604D.

The core member 604D can include a rounded proximal surface facing proximally toward the impeller housing. As described herein, this rounded surface is one arrangement that can reduce the tendency of blood to pool in or adjacent to the impeller housing.

The core member 604D can have an elongated distal portion 730D that extends distally of the distal end of the hub 608D. In one embodiment, elongated distal portion 730D comprises an enlarged portion 734 in the distal end thereof, a distal facing shoulder 738D, and a lumen 676D extending therethrough. The proximal portion 612D of the elongate body 620D can be received over the enlarged portion 734D and advanced into engagement with the distal facing shoulder 738D. Securement of the core member 604B within the hub 608D can be similar to that described in connection with FIG. 13A/B-16A.

The flexible member 602D, which can be an elongate tubular member, can take any suitable form, but as illustrated in FIG. 19A, can include a proximal portion 612D, a distal portion 616D, and an intermediate portion 620D extending therebetween. The distal portion 616D can advantageously be made atraumatic, for example by including a tapered portion as illustrated in FIG. 19A, The proximal portion 612D can be configured to be coupled with (e.g., advanced over a portion of) the core member 604D, for example, via friction fit and/or an adhesive. In some embodiments, the proximal portion 612D can have a tapered outer diameter that tapers distally towards the intermediate portion 620D. The tapered outer diameter of the proximal portion 612D can advantageously contribute to the atraumatic and pliable nature of the flexible member 602D through a gradually decreasing wall thickness (stiffness) from proximal to distal portion of the member. As illustrated in FIG. 19A, the intermediate portion 620D can be curved and/or can include a constant outer diameter. The curvature of the intermediate portion 620D can take any suitable form, such as those described herein with respect to the atraumatic tip 182. For example, the intermediate portion 620D can take the shape of a j-tip or a pigtail tip. In yet another example, the distal-most end of the intermediate portion 620D can curve around such that the distal portion 616D is generally perpendicular to the proximal-most end of the intermediate portion 620D, as illustrated in FIG. 19A. As illustrated in FIG. 19A, the distal portion 616D can have a tapered outer diameter that can be configured to reduce trauma to the patient upon insertion and/or retrieval. Advantageously, although the outer diameters of the proximal portion 612D and the distal portion 616D may taper distally, the inner diameter of these structures can remain constant, e.g., the lumen 676D that extends through the flexible tip assembly 600D can have a constant diameter.

As illustrated in FIG. 19A, the flexible tip assembly 600D can be configured to be coupled with the distal members 648D (e.g., structural members) of the impeller housing as described herein. For example, the distal members 648D can be received within a space created between the core member 604D and the hub 608D. The flexible tip assembly 600D can include a locking device as described herein that is disposed between the distal members 648D and the hub 608D to prevent the flexible member 602D from being separated from the distal members 648D. Advantageously, the components of the various flexible tip assemblies described herein can be interchangeable, as desired by those skilled in the art.

2. Unitary Hub Configurations Joining Flexible Tip to Impeller Housing

While the foregoing embodiments provide advantages as discussed above, other embodiments are simplified in that they include a unitary hub structure and enable coupling of the hub to a distal portion of an impeller housing. In certain unitary hub embodiments, a distal portion of an impeller housing is insertable in a secure manner into slots in a hub. In other embodiments, the hub can be molded around a distal portion of an impeller housing with the distal portion having features to enhance the mechanical connection between these components.

Figure 20:
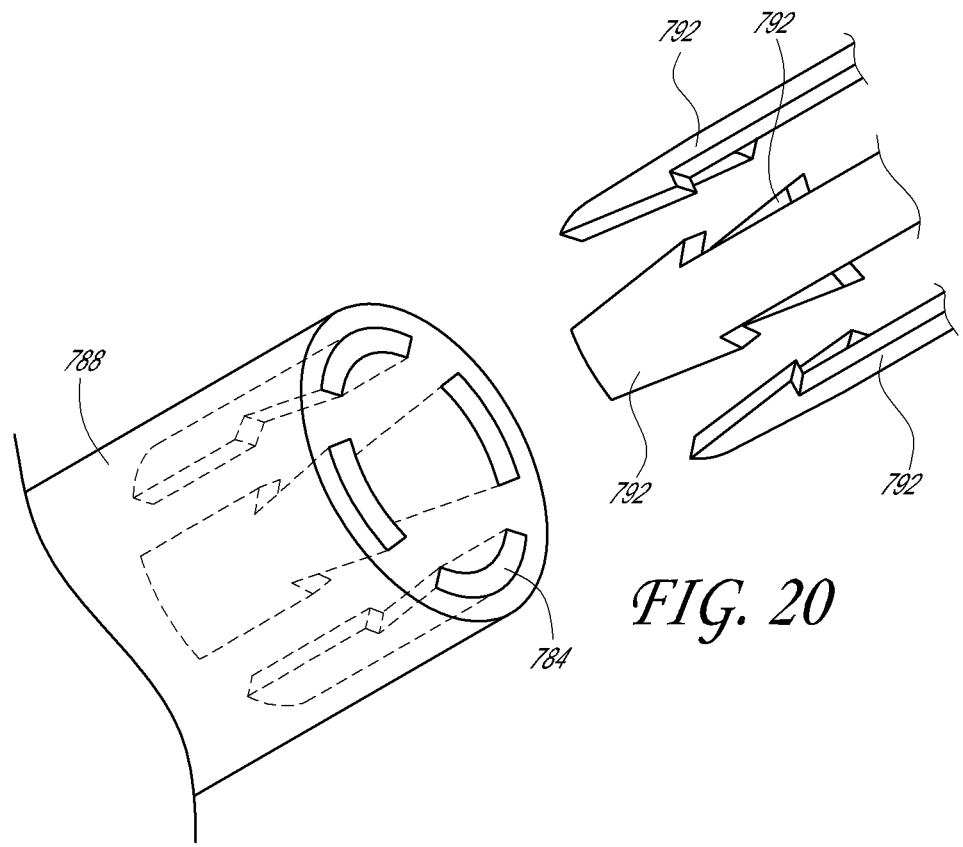
FIG. 20 is an exploded view of another embodiment of a flexible tip assembly.

FIG. 20 illustrates further features for coupling portions of a flexible tip assembly similar to those discussed above in which a plurality of slots 784 is formed in a proximal aspect of an atraumatic tip. The atraumatic tip can include a flexible J-tip (e.g., an atraumatic tip) member and a hub 788 formed with or coupled with the J-tip member, similar to those described above or formed as a unitary body. The slots 784 can be formed in a proximal end of the body of the hub 788 and can be configured to receive and be secured to distal end portions of a plurality of members 792, which extend from or form a portion of the impeller housing 202. The members 792 can be adapted to be inserted into the slots 784. In one arrangement, the end portion of the members 792 can include a locking feature configured to be engaged by a receiving feature in a proximal aspect of the hub 788. In one embodiment, the receiving feature can be a narrow aperture into a wider portion of the slot 784. In one embodiment, the locking feature on the members 792 can include an enlarged section that is adapted to be insertable through the receiving feature but not to be retractable under forces experienced in the use in the body. The enlarged section can include as a barb or a plurality of barbs in some embodiments.

Although the receiving feature and locking feature described in connection with FIG. 20 is sufficient to provide a robust connection between the members 792 and the slots 784, a further enhancement of the flexible tip assembly can include an adhesive or other securement device at least partially disposed in the slots 784. In some embodiments, where provided, the adhesive can be configured to substantially fill the slots 784 to reduce any space for blood pooling around the tip assembly, which could lead to thrombus formation. In one variation, the slots 784 are covered with a material that prevents pooling around the tip assembly without providing an adhesive or other device for providing securement.

Figure 21:
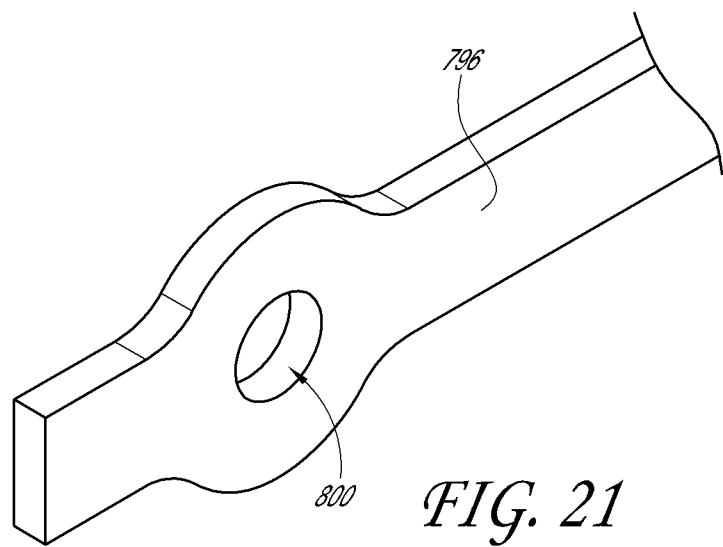
FIG. 21-21B illustrate embodiments of a portion of an impeller housing that is configured to be securely integrated into an insert molded hub of a flexible tip assembly.
Figure 21A:
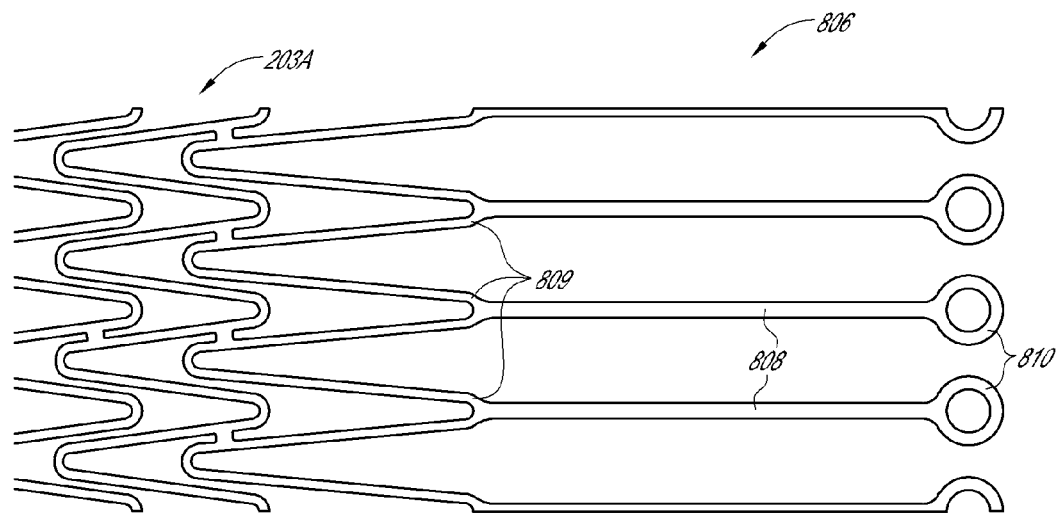
Figure 21B:
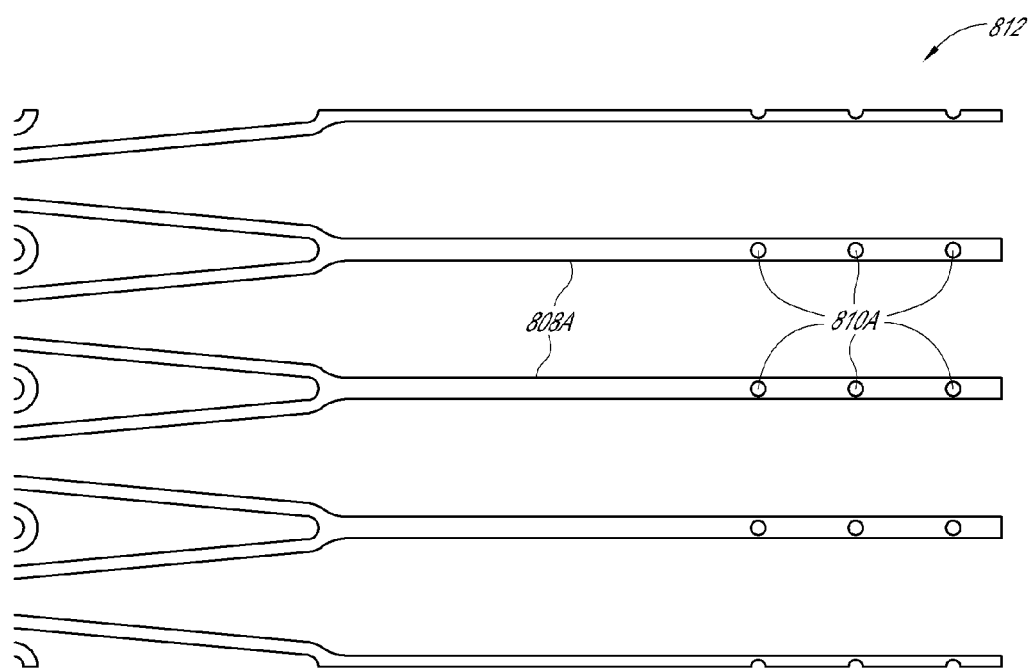

FIG. 21-21B illustrate other embodiments for enhancing the securing of a connection between a distal portion of an impeller housing and a hub.

In FIG. 21, a distal portion of a member 796 forming a distal portion of a variation of the impeller housing 202 includes a feature for integrating the member 796 with a hub body or other component of a flexible tip assembly. In one embodiment, the feature for integrating the member 796 comprises a through-hole 800 through which a moldable material may flow or bridge. In other words, the through-hole 800 permits a first portion of molded material to be formed on an inside portion of the member 796, a second portion of molded material to be formed on an outside portion of the member 796 and a third portion to extend through the through-hole 800 to integrally form with the first and second portions to create a unitary body through and surrounding the member 796. The arrangement of FIG. 21 is advantageous for use in an insert-molding process. In one variation of the embodiment of FIG. 21, the through-hole 800 is replaced with a recess that extends only partly through the thickness of the member 796. The recess is configured such that a volume of material that forms a hub into which the member 796 can be incorporated can be received therein. A step or ledge is formed between the recess and the surface of the member 796. Interactions between this step or ledge and material of the hub spanning across the step or ledge limits or prevents relative movement therebetween.

FIG. 21A shows details of a distal portion of one embodiment of an impeller housing 202A having a mesh structure 203A. Details of variations of the pattern of the mesh structure are set forth in U.S. application Ser. No. 12/829,359, filed Jul. 1, 2010 and in U.S. Pat. No. 7,841,976, issued Nov. 30, 2010. These documents are hereby incorporated by reference herein in their entirety for all purposes. FIG. 21A shows that a distal portion 806 of the mesh 203A includes a plurality of elongate filaments 808 extending from distal apices 809 of the mesh 203A. The elongate filaments 808 terminate in a securement feature 810. In the embodiment of FIG. 21A, the securement feature 810 is the distal most structure of the mesh 203A. The securement feature 810 comprises a circular structure branching laterally from a longitudinal axis of each of the filaments 808. The circular structure can be an annulus as illustrated in FIG. 21A or can be a disc that is configured to enhance securement of the filament 808 to a hub, similar to the hub 788 or to other distal structure. For example, a disc could be provided with a recess or cavity on the inner side or outer side of the mesh structure 203A. In another variation a disc could be provided with one or more protrusions on one or more of the inside and outside of the mesh 203A.

FIG. 21B is a variation of the structure of FIG. 21A with modified filaments 808A that are configured to provide for securement of the distal portion 806 over a distal length 812 rather than at the distal end of the filament as in FIG. 21A. FIG. 21B shows that in one embodiment, each of the filaments 808A can be provided with a plurality of securement features 810A disposed along the distal length 812. In one embodiment, more than one securement feature 810A is provided. As discussed above, the securement features 810A can be through-holes recesses, or protrusions. As shown, three securement features configured as through-holes can be provided along the distal length 812 of each of the filaments 808A. By providing a plurality of securement features 810A, the coupling can be spread over multiple points, providing redundancy in the securement to assure that the mesh will not be inadvertently detached from a hub with which it is connected. Also, by securing these components over a length, any twisting of the filaments 808A relative to a hub due to a torque applied to either structure will be reduced or eliminated.

B. Impeller Housing Configurations

The impeller housing 202 provides critical functions for the heart pump 10.

A key functional capability of the housing 202 in certain embodiments is to be able to significantly change in diameter, e.g., to be collapsed and expanded, repeatedly. Also, in certain embodiment the housing 202 is configured to deform in use in response to the approach of the impeller blades 212 as a way to manage separation between the blades and an inner wall of the housing 202.

1. Housing Configurations Using Shape Memory Materials

Figure 4A:
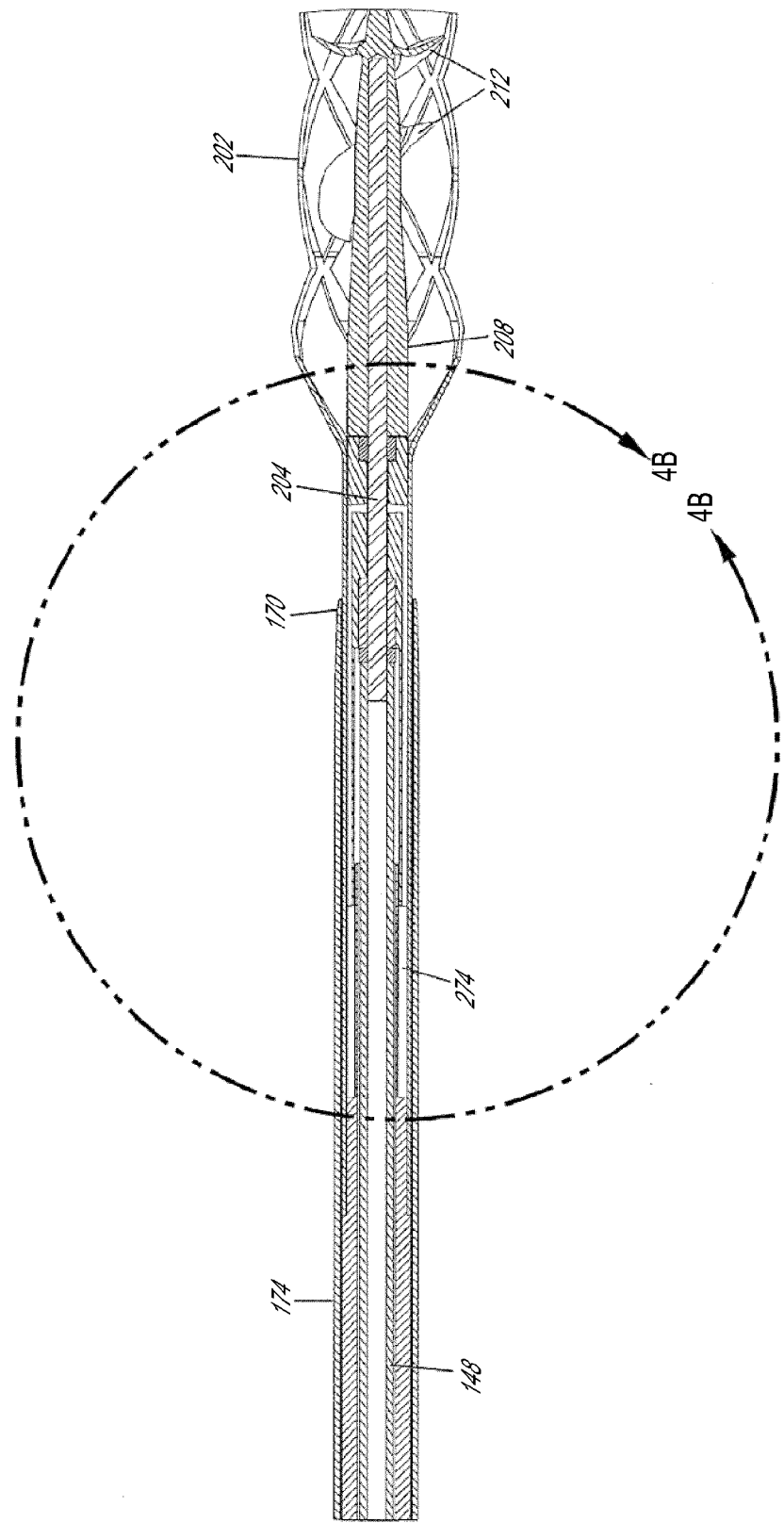
FIG. 4A is a cross-sectional view of a distal portion of the catheter assembly, taken through the section plane 4A-4A shown in FIG. 2.
Figure 4B:
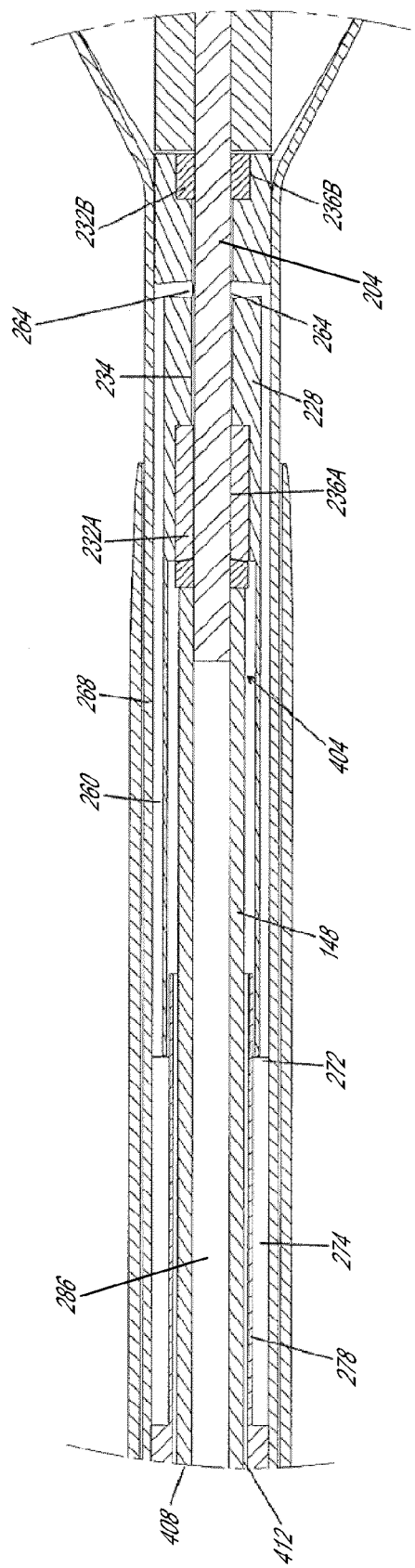
FIG. 4B is a detail view of the distal portion of the catheter assembly, taken at 4B-4B shown in FIG. 4A.
Figure 5:
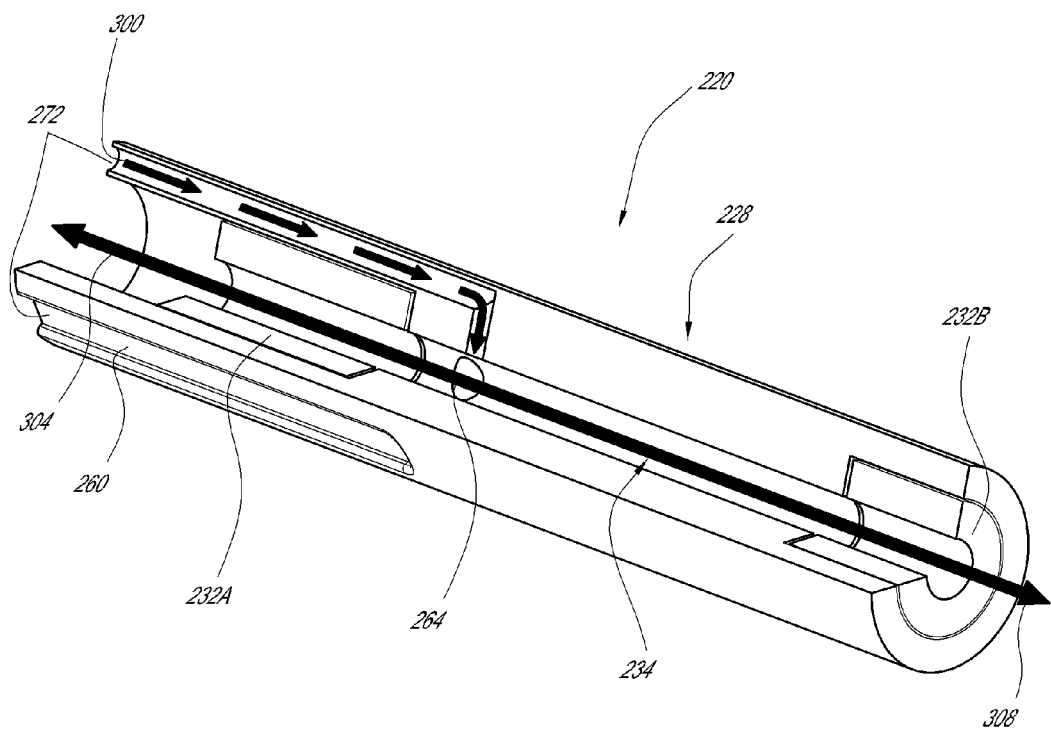
FIG. 5 is a cross-sectional perspective view of a bearing assembly of the heart pump of FIG. 1A.
Figure 6:
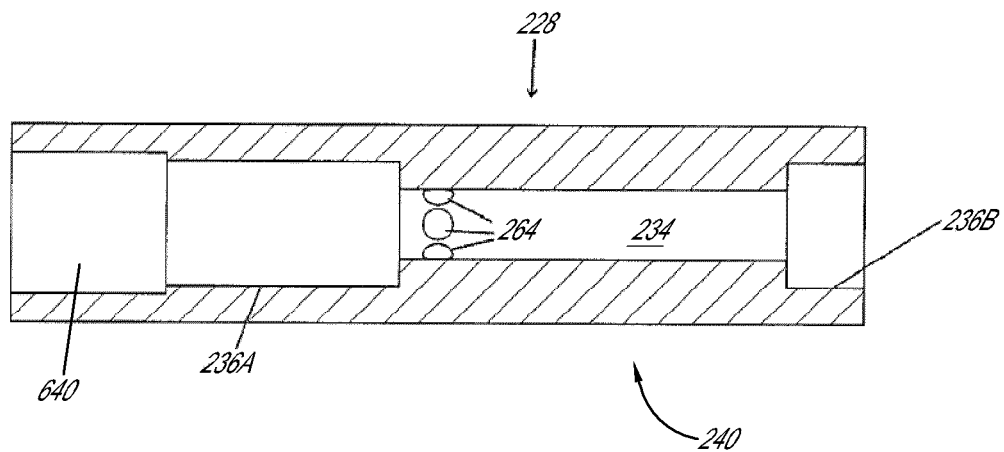
FIG. 6 is a cross-sectional view of a bearing housing of the bearing assembly of FIG. 5.
Figure 7C:
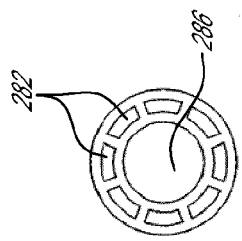
FIGS. 7A-7C show variations of the catheter body of FIG. 7.
Figure 7B:
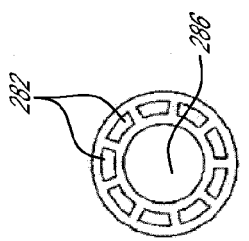
Figure 7A:
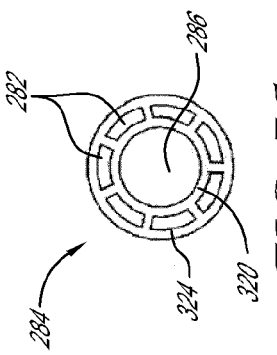
Figure 8:
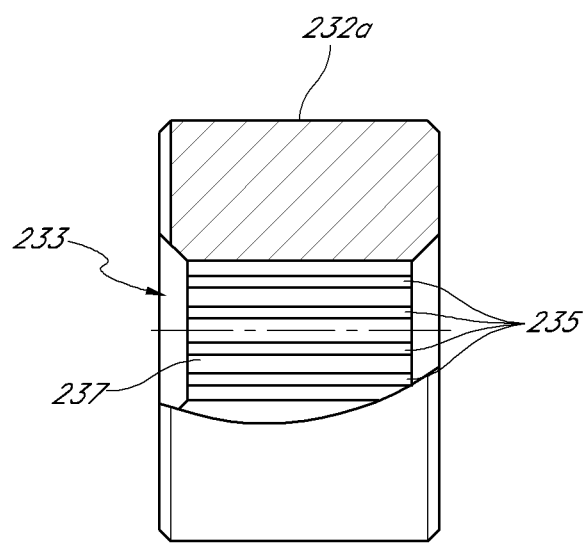
FIG. 8 illustrates a surface configuration of one embodiment of a bearing adapted to enhance or control flow of an infusant in the bearing assembly of FIG. 5.
Figures 1, 9B:
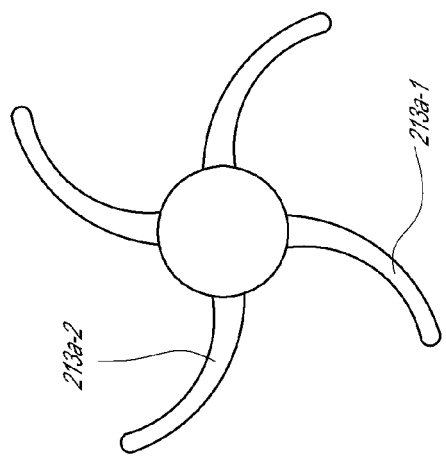
Figures 2, 9B:
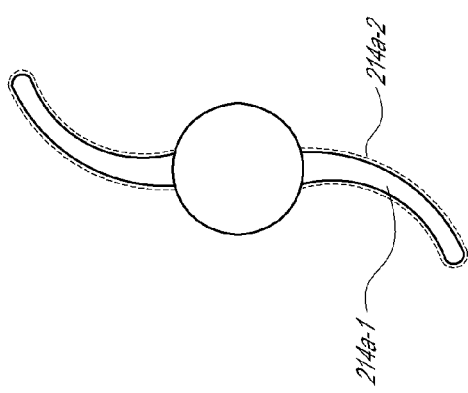
Figure 10:
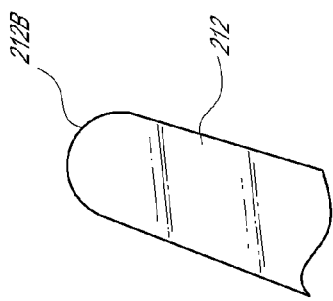
Figure 10A:
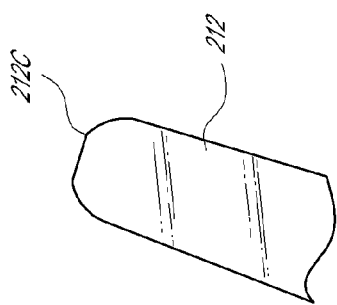

FIGS. 2 and 4A illustrate expanded arrangements of the housing 202. In a collapsed state, the housing 202 and the impeller blades 212 are collapsed into a profile no larger than the inner diameter of the sheath assembly 162. In the course of using the pump 100, the housing 202 may be cycled between the collapsed and expanded configurations multiple times.

The intended deformability of the housing is facilitated by one or both of structure and material choices. In some embodiments, at least a portion of the housing 202 can be formed from a shape memory material. Shape memory materials include materials that will expand to a predetermined state after being compressed or otherwise stressed. For example, a suitable material will permit the housing 202 to expand from a collapsed state within the transverse profile of the sheath to the expanded state of FIGS. 4A-4B. Shape memory materials can also include materials capable of reversibly deforming and/or changing shape in response to a temperature change. Examples of suitable shape memory alloys include, but are not limited to, nickel-titanium (nitinol), copper-zinc, copper-zinc-aluminum, copper-aluminum-nickel, and gold-cadmium. In some embodiments, at least a portion of the housing 202 can be formed from nitinol. In one embodiment, essentially the entire housing 202 can be formed from nitinol. In other embodiments, other shape memory materials, such as shape memory polymers and/or ceramics, can be used. In yet other embodiments, at least a portion of the housing 202 may not be formed from a shape memory material. For example, in some embodiments, at least a portion of the housing 202 can be formed from stainless steel. The housing 202 can comprise commercially available materials that provide suitable collapsibility or expandability.

Advantageously, shape memory materials can undergo significant deflections and deformation, yet maintain rigidity. Expansion can be due to the elasticity of the material or due to exposure to temperatures above a specific value. Accordingly, incorporating a shape memory material into the housing 202 can contribute to the ability of the housing 202 to significantly change in diameter (e.g., collapse and/or expand radially). Thus, in some embodiments, the housing 202 can be radially collapsible and configured for percutaneous insertion, while also being expandable to an operable diameter to allow the impeller assembly 116 to expand to an operable configuration.

2. Stiffened and Relaxed Impeller Housing Configurations

Depending on the performance desired, variations of the impeller housing 202 can have enhanced stiffness or relaxed stiffness. As discussed above, one or more blades 212 of the impeller 200 are disposed and rotate within the housing 202. There is a nominal gap between the blades 212 and the housing 200 in the rest state. The operation of the pump 100 is highly dynamic, however, because many of the components of the pump are flexible and the pump is positioned in dynamic anatomical structures. Accordingly, the gap between the blades 212 and the housing 202 (also called tip-gap) can be dynamic in some embodiments. The tip gap can be controlled by enhancing the stiffness of one or more structures defining the gap, e.g., minimizing deflection of the housing 202 relative to the impeller blade(s) 212 during operation. Also, FIGS. 26-29 illustrate embodiments for reducing flow disturbing effects at inlet and outlet locations, some of which involve enhancing stiffness of the housing. Enhancing flexibility is a strategy for enabling the housing 202 to react to pressure to move away from the blade(s) 212, as illustrated by the embodiments of FIGS. 22 and 23.

Controlling tip-gap can be advantageously employed in some embodiments to compensate for movement of the catheter pump system. For instance, external forces can be applied to the impeller housing during manipulation or operation of the heart pump. These external forces may cause the impeller housing to deflect inwardly toward the blades and can cause contact between the housing and the blades. Maintaining sufficiently large tip-gap can therefore prevent undesirable contact between the impeller housing and the blades of the impeller. Example of embodiments that can help to maintain sufficient tip-gap by reinforcing or stiffening a proximal portion and/or an expandable portion of the impeller housing are discussed further in connection with FIGS. 24 and 25. Example of embodiments that help to isolate a zone of the impeller housing disposed about the blades from distal forces applied to the impeller housing distal of the blades are discussed in connection with FIG. 35 and following.

In some embodiments, the pressure created by the operation of the impeller blades can cause the coating material covering the impeller housing to deflect. Large deflections of the coating material may be undesirable if the coating contacts the blades during operation, while in other embodiments, at least some deflection of the coating may be desirable (e.g., to prevent an overly rigid coating or to enable the coating to move away from a blade that is deflect toward the coating). The compliance of the coating can therefore be modulated by selecting a coating material with the desired material properties, by modulating the thickness of the coating, and determining the appropriate cell size in which the coating is formed, as discussed herein.

a. Impeller Housing Having Stiffened Configurations for Reducing Housing Wall Deflection In one embodiment, the housing 202 is stiffened to limit movement of a wall of the housing 202. Factors such as pressures or pressure gradients along the length of or transversely across the housing 202 and loads applied to the impeller, impeller blades 212, or tip of the impeller assembly 116 can cause the clearance between the blades 212 and an inner surface of the housing 202 to vary. Other factors include varying pressure in a heart chamber or in a blood vessel adjacent the heart due to the heart being in systole and diastole, which can cause the housing 202 to dynamically change shape if the ventricular walls collapse during systole, which can affect the clearance between the blades and the inner wall of the housing 202. In addition, manipulation or operation of the device can induce external forces on the housing, which can also vary the clearance between the blades 212 and the inner surface of the housing.

There are different ways to modulate stiffness of the housing and each of these characteristic can be applied to any section of the housing. In other words, the housing is capable of having different stiffnesses at different regions attributed to a mix and match of different characteristics. In one embodiment, the housing 202 is configured to not flex in response to operational conditions so that a clearance distribution along the length of the cannula is kept above a minimum. For example, the stiffness of the housing 202 can be increased to limit movement of the housing relative to the impeller blades in response to external pressures or factors. To increase the stiffness in any portion of the housing, the density of the mesh can be increased. For example, more rings per unit length can be provided to make the housing 202 less responsive to operational conditions. In another embodiment, the geometry of the circumferential rings can be changed, such as by thickening the cross-section of the individual rings to be stiffer, thus making the housing 202 stiffer. In another embodiment, a thicker or less compliant coating can be provided over a portion of the length of the housing to enhance the stiffness in the coated region. Another embodiment would provide an enhanced connectedness between adjacent rings, such as by increasing the number of connectors between adjacent rings to increase the stiffness of the housing 202. In another embodiment, stiffer axial connectors can be provided between adjacent rings to reduce changes in clearance at the stiffened region.

FIGS. 26-29 illustrate further embodiments that advantageously control the stiffness of the housing 202 to enhance performance. The hydrodynamic performance of the heart pump 10 may be impaired by the flexibility of the housing 202 at an inlet 110 into the housing 202. As discussed above, the housing 202 can include a mesh-like structure 203 that is covered or coated with a coating 204 to provide a cannula structure. The cannula structure provides a blood flow channel through the housing 202. In some operational conditions, flapping or other deformation of the coating 204 at inlet 110 may result in an undesirable or too large pressure drop for a given blood flow rate, and may also result in blood damage via hemolysis and/or thrombus formation. Accordingly, it is desirable to provide housing 202 with a stiffened region at the inlet 110 while maintaining the overall flexibility of the cannula both to accommodate the patient's vascular geometry and to facilitate the compressibility of the cannula for percutaneous insertion.

The expandable portion of the housing 202 may be provided with various inlet and outlet features.

Figure 26:
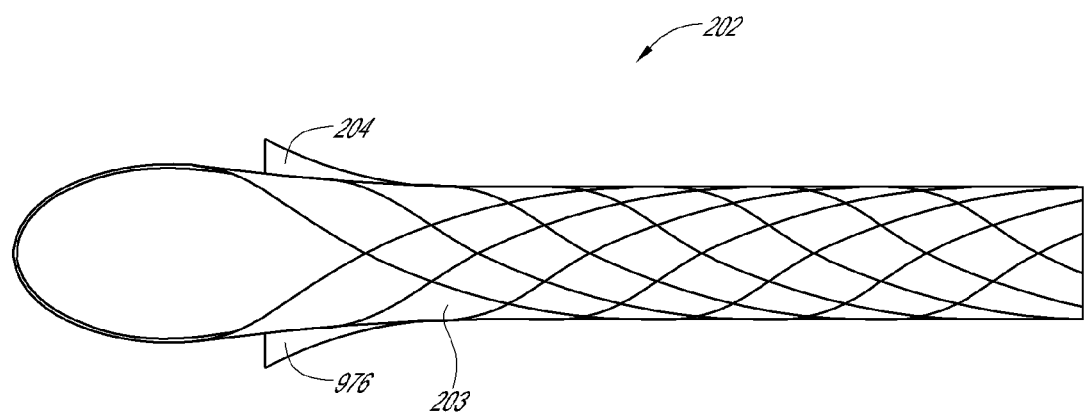
FIG. 26 is a side elevational view of the distal end of an expandable cannula.

FIG. 26 shows the distal end of an expandable housing 202 formed using any suitable manufacturing technique to provide a thicker coating 204 and a lip 976, e.g., a distally oriented protrusion, at the free end of the housing 202. In FIG. 26, the thickness of the lip 976 has been greatly exaggerated to make the lip 976 more visible. Although thicker, in some embodiments, the enhanced thickness is not so great as to substantially increase the crossing profile of the catheter assembly 100. The increased thickness of coating 204 and the lip 976 improve the structural stiffness of the cannula inlet.

Figure 27:
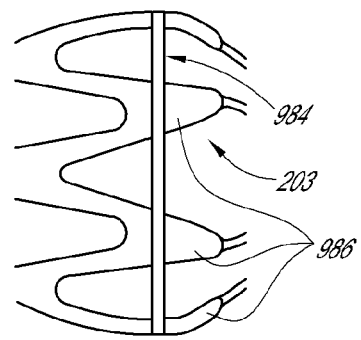
FIGS. 27 and 28 are schematic side elevational view of the proximal end of an embodiment of an expandable cannula showing a diffuser arrangement.
Figure 28:
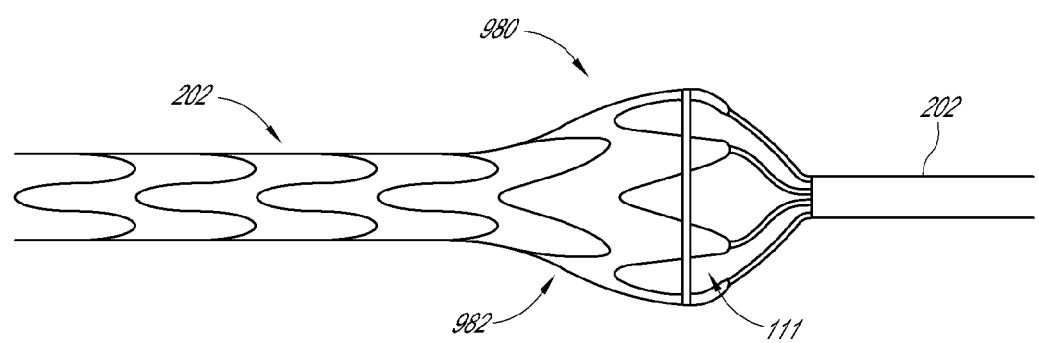

The benefits of cannula shaping may also be applied to an outlet 111 at the proximal end of the housing 202. FIGS. 27 and 28 show a proximal end portion of a cannula 202 that can be shaped using any suitable process. The outlet 111 has a diffuser arrangement 980 at the proximal end of the housing 202. The housing 202 of FIGS. 27 and 28 may have an outwardly flared portion 982 of the outlet 111 and optionally a crisp lip 984, e.g., a ring, at the proximal end of the coating 204. In addition to lip 984, the outlet 111 may include a plurality of leaflets 986 defined by the end wire structure of mesh 203 and filled with the material of coating 204. In some embodiments, each cell or portion of the mesh can be completely filled with the coating material such that no cell is only partially filled with the coating material. Thus, in some embodiments, the coating material can be completely surrounded by struts in the housing.

Figure 29:
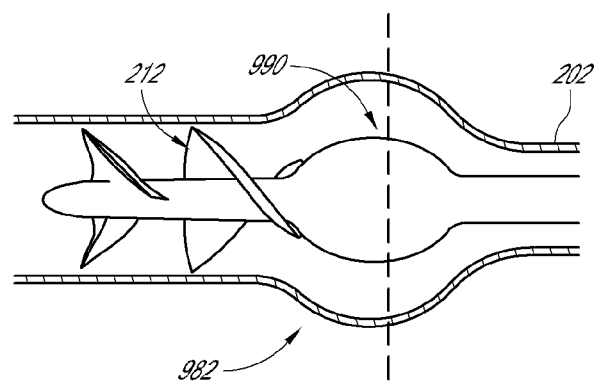
FIG. 29 is a schematic side elevational view of the proximal end of an embodiment of an expandable cannula showing its relationship to an impeller hub diffuser.

The complex geometry of the housing 202 around the outlet 111 can be configured to cooperate with the impeller assembly disposed in the housing 202. For example, as shown in FIG. 29, in some embodiments a diffuser 990 can be disposed downstream of the blades 212 of the impeller. The diffuser 990 can have a tapered outer surface that is configured to create a divergent flow in the housing 202. The outwardly flared portion 982 can advantageously accommodate the flow regime induced by the impeller blades 212 and the diffuser 990. For example, generally axial flow (from left to right in the figure) can be altered to have a radial component by the diffuser 990. Because the housing 202 has the outwardly flared portion 982 at the location of the diffuser 990, the radial flow is accommodated without creating excessive back-pressure in the housing 202. The dashed line in FIG. 29 shows that in one embodiment, the outwardly flared portion 982 has a largest radially extent at substantially the same axial position in the heart pump illustrated therein as the largest radial extent of the diffuser 990. Thus the outwardly flared portion 982 enables higher flows for comparable pump configurations compared to an impeller assembly having a diffuser and being mounted in a straight housing. The outwardly flared portion 982 also could minimize hemolysis by reducing radial concentration of red blood cells at the axial position of the diffuser 990.

The leaflets 986 are advantageous in that they spread out axially the position of the pressure drop that occurs at the outlet 111 from the inside of the housing 202 to the outside thereof. If the pressure drop across the inside-to-outside boundary were concentrated at a single axial location, a generally conical flow pattern might result. Although such a pattern may be acceptable, it would be unlike typical arterial flow which is more random due to the varying pressure in the arterial system. In contrast, by providing the leaflets 986 the outflow is much more random and more consistent with native vascular, e.g., arterial flow.

b. Impeller Housing Having Enhanced Flexibility for Dynamic Tip-Gap Control

In another embodiment, the stiffness of the housing 202 can be reduced to permit the housing to flex in response to conditions such as instantaneous pressure rise at the wall. Such a pressure rise may result from the blades 212 being deflected toward the inner wall of the housing 202. By reducing the stiffness of the housing 202, the wall is able to expand or be deflected in an advantageous manner. A reduction of the stiffness of the housing 202 can be achieved by reducing the density of the mesh in the region where stiffness is desired to be reduced. In another embodiment, the stiffness of the housing 202 can be reduced by providing fewer circumferential rings or other members per unit length in the region to be made less stiff. In one embodiment illustrated by FIGS. 22 and 23, the housing 202 can be made less stiff by reducing the stiffness of individual components of the mesh, such as making the rings thinner in a region where enhanced flexibility is desired. For example, FIG. 22B shows a detail view of a tip of blade 212 of an impeller adjacent an inner wall W of the housing 202. A gap G between the wall W and the blade 212 corresponds to the clearance between the blade 212 and the wall W.

In FIG. 22B, the gap G is illustrated as being very small. A too-small gap can result in hemolysis as discussed herein. FIG. 23 illustrates how a pressure adaptive housing 202A can be configured to maintain an acceptable gap. In particular, the housing 202A is made more flexible at least in the region of the blades 212. As a result, the wall W of the housing 202A will be deflected by local pressures due to the operation of the impeller of which the blades 212 are a part. More particularly, the housing 202A can be configured with a flexible impeller zone 207 (e.g., void or cell area defined by struts with coating material) that will be radially deformed in certain operational conditions. For example, if the impeller is deflected from a nominal central position toward the wall of the housing 202A, an area of the housing 202A at the same axial position, e.g., flexible impeller zone 207, will be radially deflected outward. This is shown in FIG. 23B in which a portion of the housing 202A corresponding generally to the flexible impeller zone 207, e.g., when in use, protrudes from an otherwise continuous cylindrical surface of the wall W to form an internal channel within the housing 202A corresponding to the shape of the blade 212. The protruding portion creates a gap G1 that is greater than the gap G in FIG. 22B. The enlarged gap G1 corresponds to more clearance between the blade 212 and the wall W so that red blood cells or other blood components will not be damaged flowing through the impeller zone. Those skilled in the art may appreciate that the protruding portion of the housing 202A may not always protrude from the otherwise continuous cylindrical surface of the wall W. For example, the protruding portion may be configured to protrude only when the heart pump is in use, e.g., when the impeller is deflected under operating conditions.

A variety of techniques can be used to cause the housing 202A to provide an enlarged gap or to protrude radially at the impeller zone. In one embodiment, the housing 202 is coated along its length, but the coating is made thinner in a region where enhanced flexibility would be advantageous. In another arrangement, it may be advantageous to increase the flexibility of the housing by reducing the number of axial connectors or entirely eliminating connectors between adjacent rings in the region to be made more flexible.

Additional advantages of enabling the housing 202 to be adaptive to the pressures to which it is exposed in use may result. For example, in some embodiments, pressure responsive shaping of the housing 202 immediately adjacent to in the impeller inlet plane to be straight or slightly converging or slightly diverging may be useful to optimize radial velocity profile to the impeller. These arrangements may be the result of exposing a housing 202 that is configured to be responsive to differences in pressure across cannula due to blood pressure and instantaneous pump through-flow velocity and other factors discussed above. This arrangement may be preferable to requiring significant bell-mouth inlet convergence shaping well upstream of impeller.

Adaptive cannula shaping can provide a more robust configuration. For example, clearances between the impeller blade tips and the cannula inner surface are very difficult to control with realistic manufacturing tolerances and due to deflections in the impeller shaft that can occur due to the impeller shaft not being a perfectly rigid element. If this clearance is too wide, there is a loss of performance. If it is too small, undesirably high fluidic stresses can occur and result in unacceptably high hemolysis, or even result in potentially damaging contact between the impeller blade tip and the cannula inner surface.

Although shaping of the cannula structure for significant bell-mouth inlet convergence generally can be helpful, other important factors include impeller radial runout and shaft deflection. By having a cannula coating that deflects in response to the localized pressure force produced at and near the impeller blade tip, a desirable tip-to-cannula gap can be maintained.

In some embodiment, a portion of the housing 202 downstream of the impeller blades 212 is made pressure responsive such that the shape of the housing is induced by the ambient pressure. For example, the housing 202 can be configured to present a shape that would provide flow benefits downstream of the blades 212. The housing 202 can be configured to be diverging downstream of the impeller exit plane in a manner that optimizes diffusion downstream of the impeller. The housing 202 can be configured downstream of the impeller exit plane in a manner that optimizes deswirl in the downstream flow region. Such a shaping can be induced by pressure in the housing 202 during operation or by other conditions, such as blood pressure and instantaneous pump throughflow velocity.

As discussed above, advantages can be achieved by making the housing 202 pressure adaptive or by configuring the cannula 202 to respond in a predicted manner to the ambient conditions. This can result in a gentler handling of red blood cells and other blood components that can be damaged by conditions such as a too narrow gap between the blades 212 and the housing 202.

C. Impeller Housing Support Enhancement

Figure 24:
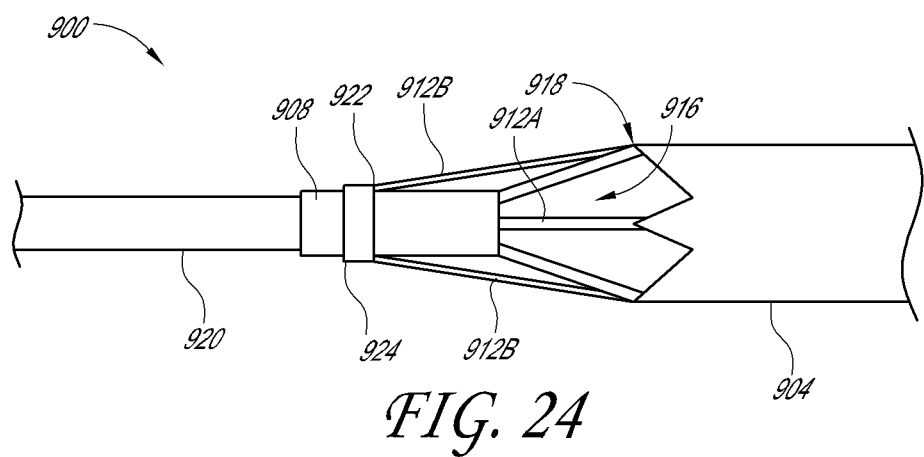
FIGS. 24-25 illustrate embodiments of impeller housings that are configured to provide enhanced support to minimize deflections of the housing.
Figure 25:
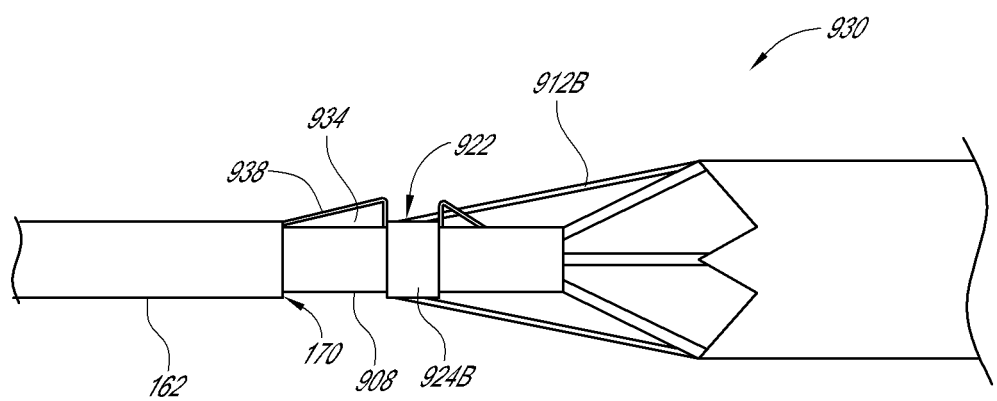

Various techniques are discussed above for enhancing the stiffness of the housing 202. Another technique for controlling clearance within the flow channel of the housing 202 is to increase the stiffness of the area within and adjacent to where the impeller is mounted. FIGS. 24-25 illustrate techniques for increasing the stiffness between the expandable portion of the housing 202 and the non-expandable section of the catheter assembly 112 proximally thereof. By stiffening a proximal portion of the impeller housing 202, transverse deviations of the proximal portion of the housing 202 or components housed therein can be reduced. A stiffening structure can be provided to maintain the impeller shaft 204 in a centered position within the impeller housing 202. These arrangements are particularly useful where the impeller shaft 204 is cantilevered from the proximal portion of the impeller housing 202. These features can be combined with an assembly that provides distal support to the impeller shaft 204, as described in U.S. application Ser. No. 12/829,359.

FIG. 24 illustrates an impeller housing 900 that is similar to the impeller housing 202 except as described differently below. The impeller housing 900 includes an expandable distal portion 904 and a proximal portion 908 that has a generally fixed profile. In one embodiment the proximal portion 908 houses a proximal portion of impeller similar to the impeller 200. An impeller can be supported in a cantilevered manner from the proximal portion 908 of the housing 902.

A plurality of members 912 extends between the proximal portion 908 and the expandable distal portion 904. The plurality of members 912 can include a first group of struts 912A to provide a secure connection between the distal and proximal portions 904, 908. A plurality of gaps 916 defined between adjacent struts 912A can be configured to permit blood flowing from an upstream location through the housing 900 to exit the housing at a downstream location. For example the gaps 916 can be disposed within a portion of the vasculature, e.g., the pulmonary artery or the aorta while an intake in of the pump of which the housing 900 is a part can be disposed in a fluid source, such as a chamber of the heart. When the pump including the impeller housing 900 is in operation, blood drawn from the left ventricle can flow through the housing 900 and be expelled through the gaps 916 into the aorta.

In one embodiment the proximal end of the proximal portion 908 of the impeller housing 900 is coupled to a catheter body 920 similar to the catheter body 120 discussed above.

In certain embodiments it is desired to stiffen a proximal section of the impeller housing 900. This can be achieved by providing one or more stiffening members coupled with the proximal portion 908 and a distal portion 904. For example, in the embodiment of FIG. 24 a second group of struts 912B is provided between distal and proximal portions 904, 908. The struts 912B are located on opposite sides of the impeller housing 900. Each of the struts 912B includes a distal end 918 coupled with the distal portion 904 and a proximal end 922 coupled with the proximal portion 908. In one embodiment, the distal end 918 is coupled with the distal portion 904 at approximately the same longitudinal position as the longitudinal position where the struts 912A connect to the distal portion 904.

In one embodiment, the proximal end 922 of the struts 912B are coupled with the proximal portion 908 at a longitudinal position that is proximal of the longitudinal position where the struts 912A are coupled with the proximal portion 908. In one embodiment, each of the struts 912B is coupled with the proximal portion 908 at the same longitudinal position. In one arrangement, a circumferential member 924, which can be a ring, extends between and couples the proximal ends 922 of the struts 912B.

FIG. 24 illustrates embodiments that advantageously stiffen the impeller housing 900, particularly in the region of the proximal portion 908 and in at least a portion of the distal portion 904 in which impeller operates. In part, the enhanced stiffness is due to a triangular structure formed between adjacent struts 912A, 912B and a length of the proximal portion 908 extending between the proximal ends of the struts 912A, 912B. This triangular structure provides a rigid configuration like a truss that resists deflection of this proximal zone from a central longitudinal axis of the impeller housing 900.

Depending on the materials and arrangement of impeller housing 900, the forced to collapse the expandable distal portion 904 can be increased by the presence of the struts 912B.

FIG. 25 illustrates another embodiment of an impeller housing 930 in which the stiffening benefit of struts 912B is provided while maintaining or reducing the collapsing force needed to collapse the expandable distal portion 904. The impeller housing 930 is similar to the impeller housing 900 except as described differently below. In the impeller housing 930, at least the struts 912B are coupled with the structure that is locked in an axial position in a first configuration and that is capable of sliding proximally to a second axial position in a second configuration.

In one embodiment the proximal ends 922 of the struts 912B are coupled with a slidable circumferential structure 924B. The slidable circumferential structure 924B can comprise a short sleeve disposed about proximal portion 908. In one embodiment a locking device 934 is provided to hold the circumferential structure 924B in a first axial position about the proximal portion 908. The locking device 934 may have a first configuration in which at least one of a shoulder is provided to limit the axial travel of the circumferential structure 924B. In one embodiment, a distal-facing shoulder is provided. In another embodiment, proximal and distal-facing shoulders capture the circumferential structure therebetween. In one embodiment, the locking device 934 includes a ramped proximal portion 938. The locking device 934 can be actuated to a second configuration in which the circumferential structure 924B is permitted to slide proximally on the proximal portion 908. In one embodiment, advancement of the distal end 170 of the sheath assembly 162 into engagement with the ramped proximal portion 938 causes the forward facing shoulder of the locking device 934 to be retracted such that the forward facing shoulder does not prevent proximal movement of the circumferential structure 924B. Further advance of the distal end 170 of the sheath assembly 162 causes the distal end to engage the struts 912B. Continued advancement of the distal end 170 of the sheath 162 causes the struts 912b to be collapsed against the proximal portion 908 and also causes the circumferential structure 924B to slide along the proximal portion 908. Depending on the configuration of the impeller housing 930, the circumferential structure 924B can slide proximally or distally during the collapsing of the distal portion 904.

In another embodiment, the locking device 934 can be actuated by a mechanism disposed on the proximal end of modified version of the pump 100. For example, a tension member such as a wire can be disposed within the catheter assembly 112. For example, a pull wire can be disposed within a peripheral lumen formed in a catheter body similar to the catheter body 120. For example, one of the lumens 282 illustrated in FIG. 7-7C can be configured to house a pull wire. Actuation of the pull wire from the proximal end of the modified pump can cause the locking device 934 to disengage from the circumferential structure 924B, e.g., to be actuated to a retracted position, permitting movement of the circumferential structure 924B.

The locking device 934 can be configured with a proximal locking component and a distal locking component in one embodiment. Where proximal and distal locking components are provided, axial sliding of the circumferential structure 924B is prevented in both the proximal and distal directions when the locking device 934 is actuated to a locked configuration.

In one embodiment, the locking device 934 includes a retractable latch.

The enhancement of the stiffness of the proximal portion and a proximal zone of the distal, expandable portion of an impeller housing in embodiments illustrated by FIGS. 24-25 is advantageous in that it provides one approach to controlling undesirable interactions between impeller blades 212 and inner surfaces of the impeller housing. Contact between impeller blades 212 and inner surface of the impeller housing can lead to damage to certain blood components such as red blood cells. At the relatively high blood pump pressures and flows anticipated in the pump 100, minimizing hemolysis is a significant advantage.

III. Catheter Assembly Having Integral Dilating Structure

FIGS. 30-33 illustrate a catheter assembly 1000 with a sheath assembly 1028 and a tip assembly 1004 having an integral dilating structure 1008. The catheter assembly 1000 can be used with a heart pump, as discussed above, and can provide several advantages. For example, by integrating the dilating structure 1008 into the tip assembly, the tip assembly can be used to dilate anatomical structures such as the aortic valve. Also, the configuration of the dilating structure 1008 can be selected to space an intake structure from the anatomy to prevent the anatomy from being sucked into the intake. These embodiments advantageously can be made with fewer parts and benefit from not including a distal flexible member as in some of the other embodiments herein.

Figure 30:
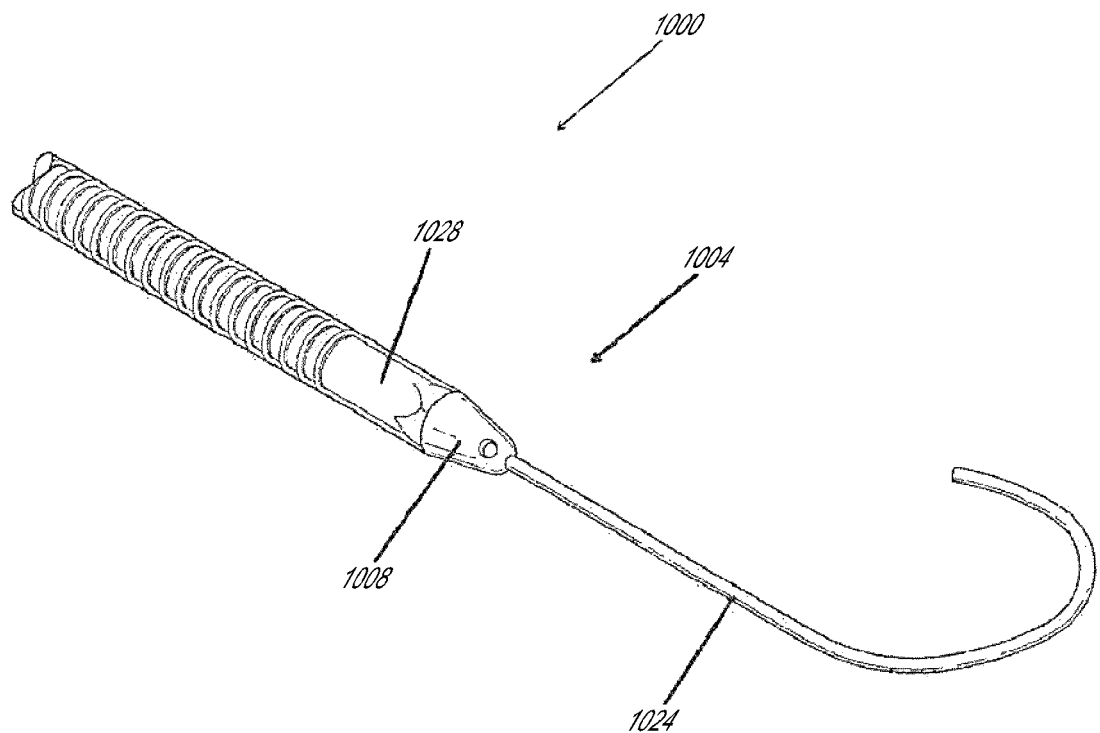
FIGS. 30 illustrate another embodiment of catheter assembly in which a dilating structure is integrated into an impeller housing.
Figure 34:
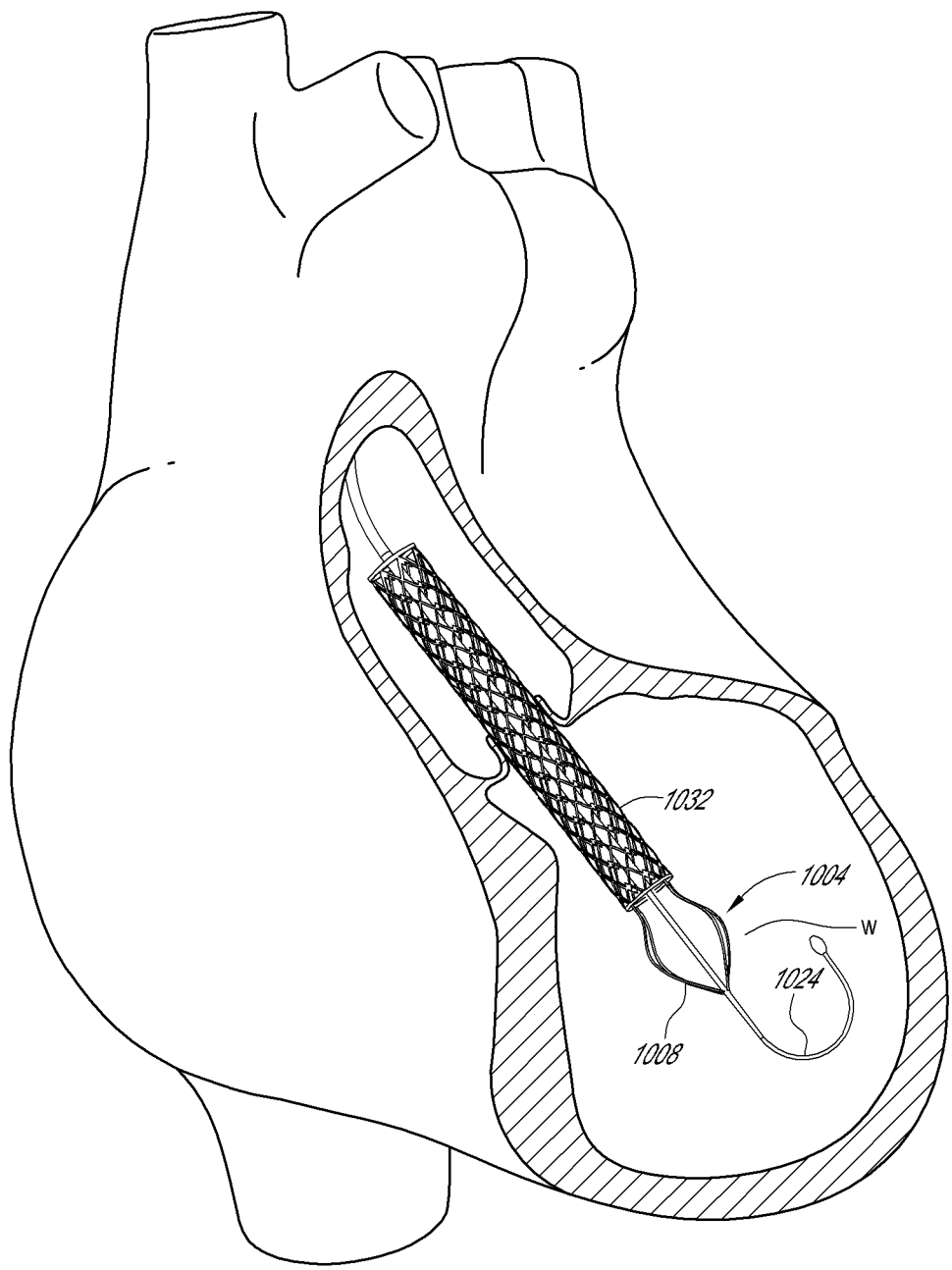
FIG. 34 show the catheter assembly of FIG. 30 in position within the anatomy.

FIG. 31 shows that the catheter assembly 1000 is capable of percutaneous insertion and includes an impeller 1012 having one or more foldable blades 1016 and an expandable housing 1020 surrounding the impeller. The housing 1020 can be configured as a cannula in some embodiments. The housing 1020 has a collapsed configuration for delivery to a desired location within the body and an expanded configuration in which the impeller can rotate to pump blood. The collapsed configuration is illustrated in FIG. 30 and the expanded configuration is illustrated in FIGS. 31-33. FIG. 34 shows the catheter assembly 1000 deployed in the anatomy and in the expanded condition.

The catheter assembly 1000 includes the sheath assembly 1028 that is similar to those hereinbefore described and can be advanced over a guidewire 1024. The guidewire 1024 can be used to access the anatomy, e.g., the left ventricle as illustrated in FIG. 34.

The catheter assembly 1000 can track over the guidewire 1024 to a selected position, e.g., with a proximal portion of the impeller housing 1020 residing in the ascending aorta, the distal portion of the impeller housing 1020 (including the dilating structure 1008) residing within the left ventricle, and the impeller housing 1020 generally crossing the aortic valve. Optionally, the dilating structure 1008, positioned within the left ventricle, can then be urged into contact with the aortic valve, e.g., at the ventricular side of the aortic valve, to separate the aortic valve leaflets from each other. This can advantageously enable the catheter assembly 1000 to be advanced through the aortic valve into the heart in a minimally traumatic manner, protecting the aortic valve. In other embodiments, for example as illustrated in FIG. 34, the dilating structure 1008 may be positioned sufficiently distal to the aortic valve such that it does not contact the aortic valve upon expansion/dilation. Thereafter, the distal portion 1032 of the housing 1020 is disposed in the left ventricle and a proximal portion of the housing 1020 is located in the ascending aorta, as illustrated in FIG. 34.

When positioned in the anatomy, the catheter assembly 1000 extends proximally to a peripheral access site, such as a femoral access site. After delivery, the guidewire 1024 can be retracted by applying a proximally directed force while holding the proximal end of the catheter assembly in place.

FIG. 34 illustrates a method in which the guidewire 1024 is left in place after the sheath 1028, shown in FIG. 32 has been retracted. In this method, the housing 1020 is expanded before the guidewire 1024 is removed. In another method the guidewire 1024 is first removed, then the sheath assembly 1028 is retracted permitting the housing 1020 and the impeller blades 1016 to be expanded. Those skilled in the art may appreciate that regardless of the order in which the guidewire 1024 and the sheath 1028 are retracted, the guidewire 1024 should be completely retracted prior to and/or during operation of the device (e.g., the guidewire 1024 should be removed before the device is operated.)

FIGS. 31 and 33 show that the dilator 1008 includes a port 1040 configured to receive the guidewire 1024. The guidewire 1024 can also be advanced through the impeller 1012 in various embodiments. Further features that facilitate advancement of a guidewire through an impeller are described in U.S. patent application Ser. No. 12/829,359, filed Jul. 1, 2010. The dilator 1008 can be configured as a plurality of arms 1044 extending outward and proximally from the port 1040. The arms 1044 form a substantially continuous surface extending proximally from the port 1040 in the collapsed state (see FIG. 30) and a substantially blunt structure in the expanded state (see FIG. 32-33). More particularly each arm 1044 can extend from a central hub 1048 disposed around the port 1040 to a proximal end 1052 disposed away from the hub 1048. The proximal end 1052 may be joined to a distal end 1054 of an elongate structural member 1058, a proximal end 1062 of the member extending from a mesh of expandable members forming the housing 1020.

As in other embodiments, the housing 1020 can optionally include a covering or coating and in the embodiment of FIGS. 30-34, a distal portion 1070 of the coating extends a portion of the length of the elongate members 1058. FIG. 32 illustrates that coating the distal end presents a transverse size (e.g., cross-sectional area, diameter, or height in the view of FIG. 32) that is significant larger than the transverse size of the central portion of the housing 1020. This enables a gentle intake of blood into the lumen in the housing 1020. In other words, there is a much more gradual pressure change in the blood that flows from outside the structural members 1058, through the members 1058 and proximally across the distal portion 1070 into the lumen in the housing 1020. This provides a more atraumatic conveyance of blood into the catheter assembly 1000.

Each arm 1044 may be configured to couple with a distal portion of the sheath assembly 1028. In one embodiment, a proximal portion of each arm 1044 has a reduced thickness such that the distal end of the sheath assembly 1028 can be urged up into abutment with a proximal ridge 1072 of the thicker, distal portion of the arms 1044. This sliding and abutting provides a minimum step up in diameter from the diameter of the arms 1044 to the diameter of the sheath assembly 1028 so that transition from the arms 1044 to the sheath assembly will slide through the anatomy with ease.

FIG. 33 illustrates a relief area 1066 provided between adjacent arms 1044 to enable the arms 1044 to more closely conform to a gradually proximally expanding structure that would be suitable for dilating tissue.

One advantage of the embodiments illustrated by FIGS. 30-34 is that the dilator 1008, as an integrated part of the expandable housing structure, enables the catheter assembly 1000 to be advanced through the vasculature without an independent delivery sheath being disposed between the sheath assembly 1028 and the patient, which is typical in percutaneous procedures. The elimination of the independent delivery sheath preserves a greater percentage of the crossing profile for the catheter assembly 1000. This can be advantageous in permitting an increase in the size of the impeller 1012, which can enhance flow output of a heart pump incorporating the catheter assembly 1000.

Another advantage provided by the catheter assembly 1000 is that in the expanded state, wide openings 1074 are provided between pairs of adjacent elongate atraumatic structural members 1058. The openings 1074 provide efficient intake of blood in use. Additionally, the blunt configuration of this inlet portion overall greatly reduces the likelihood that the anatomy adjacent the intake will be sucked into the intake to interfere with operation of the pump. In other words, expansion of the cannula simultaneously expands the tip of the dilator 1008, which serves to space the inlet of the cannula assembly 1000 from the inner heart wall W and other structures within the heart during a pumping operation.

IV. Impeller Assembly Having Load Isolation Configuration

FIGS. 35-38 illustrate embodiments that advantageously isolate the portion of a housing (e.g., the housing 202, 1020 or other housings described herein) in which an impeller operates from deflections that could be induced by the moving anatomy in which the heart pump 10 operates. For example, in some embodiments, a housing (e.g., any housing described herein) can have a wall structure that is configured to minimize and/or reduce deflection in a proximal region of the housing. As discussed herein and in U.S. Provisional Application No. 61/430,129, filed Jan. 5, 2011, the heart pump 10 operates more effectively when a controlled gap is provided between the spinning impeller 200 and the inner wall of the housing 202, which forms a cannula. This also applies to the housing 1020 and impeller 1012 of the catheter assembly 1000.

FIG. 34 shows that the tip assembly 1004 of the catheter assembly 1000 is disposed in the left ventricle and may be exposed in use to the movement of the beating heart, such as the wall W. This motion may adversely affect the alignment between the impeller 1012 and the inner wall of the housing 1020.

Figure 35:
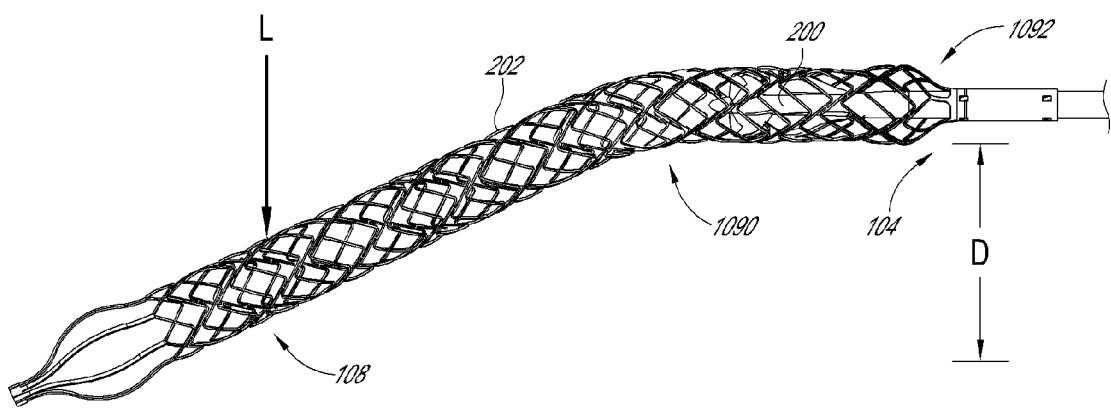
FIG. 35 illustrates deflection of an impeller housing when a load is applied to a distal portion thereof.

FIG. 35 shows that movement at the distal portion of the housing 202 (or housing 1020) due to interaction with the wall W could result in bending at the proximal portion of the housing in the area where the impeller 200 (or impeller 1012) operates. A bending load L applied at the distal end 108 of the housing 202 or a transverse displacement D of the distal end 108 from a straight projection of the orientation of the proximal end 104 can create a transition zone 1090 adjacent to an impeller zone 1092 where the impeller 200 operates. Having uniform stiffness along the length of the housing 202 distal the impeller 200 can potentially result in a substantially straight length of the housing 202 between the transition 1090 and the distal end 108. This can cause the transition zone 1090 to be localized adjacent to the impeller 200, which is disadvantageous when the cannula collapses where stress concentrates at the localized region. This can adversely affect the gap between the impeller and the housing 202.

Figure 36A:
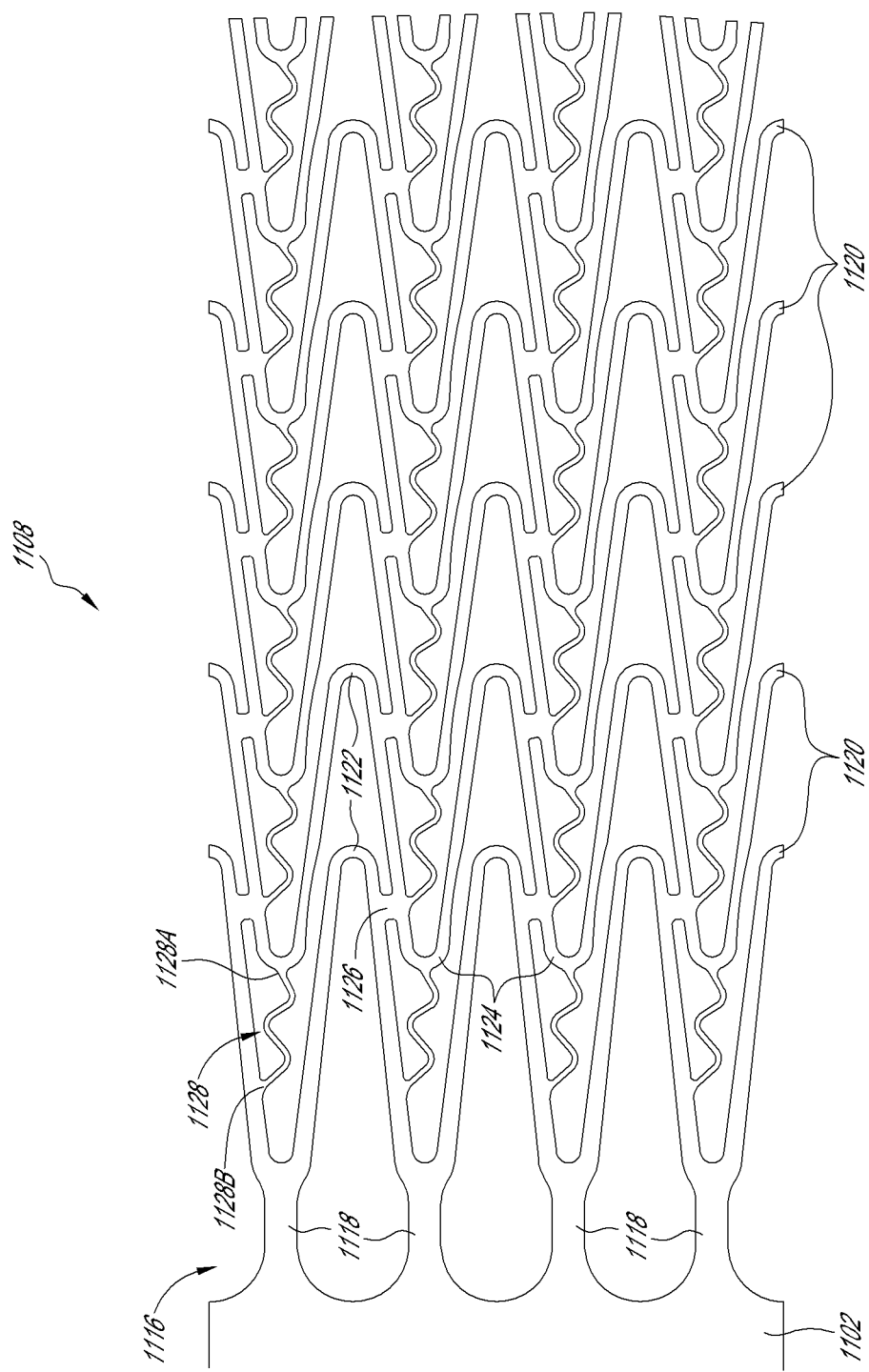
Figure 36B:
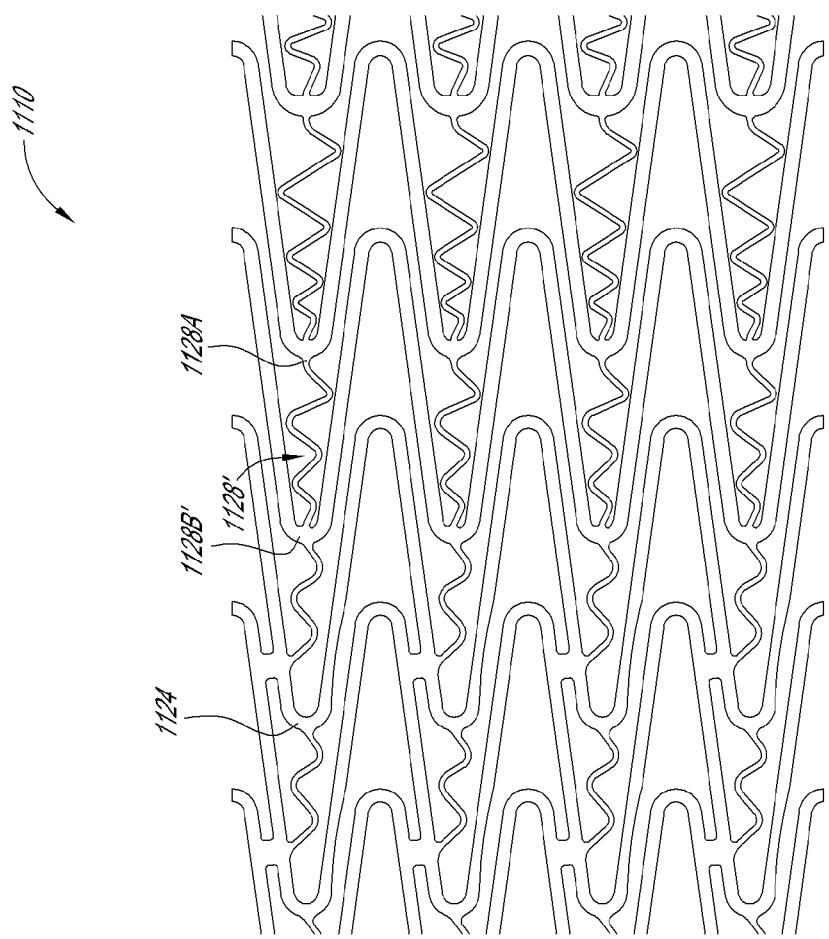
Figure 36D:
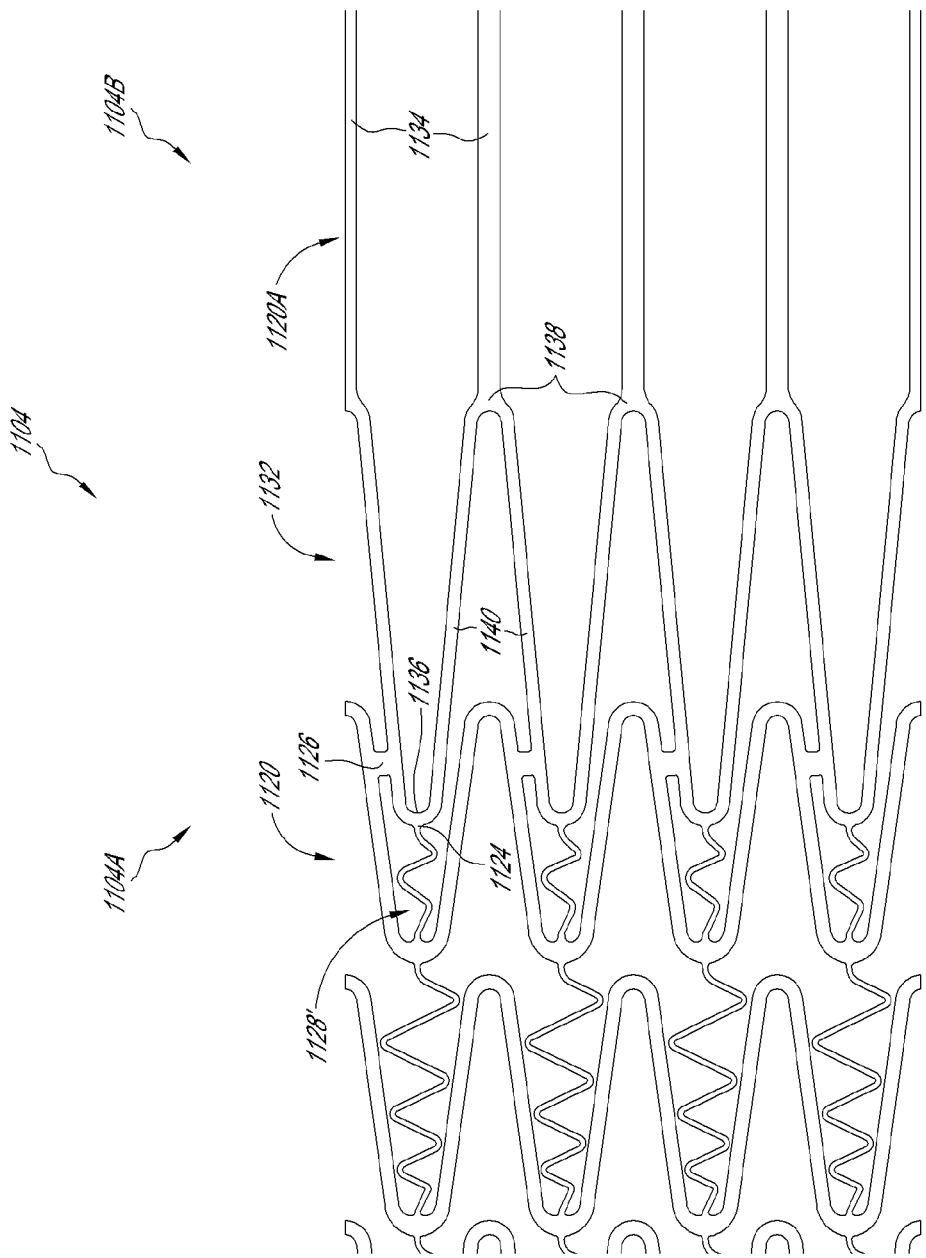

FIG. 36-36D illustrate in a flat form a wall pattern 1100 that can be used to form a structure similar to the cage or mesh structure 203. The pattern 1100 includes a proximal portion 1102 a distal portion 1104 and an elongate pattern 1106 extending therebetween.

The proximal portion 1102 can take any form, but may be rigid enough to be securely coupled with the bearing housing 220. The proximal portion 1102 can form a generally fixed perimeter hollow cylinder configured to be fitted over the bearing housing 220. The distal portion 1104 can be configured to have a low profile for delivery and to expand to permit efficient intake of blood, such as by forming openings similar to the openings 1074 discussed above when expanded. The low profile can be the same as or similar to or smaller than that of the proximal portion 1102. In one embodiment, the distal portion 1104 is coupled with an atraumatic tip, such as illustrated and described in connection with FIGS. 13-21B. In another embodiment, the distal portion 1104 forms a portion of a dilating structure such as the integrated dilating structure 1008.

The elongated pattern 1106 can take any suitable form, but may include a plurality of expandable zones with different rigidities to enable isolation of the impeller zone 1092 from the load L illustrated in FIG. 35. In one embodiment, the elongate pattern 1106 includes a first expandable zone 1108 disposed adjacent to the proximal zone 1102. The first expandable zone 1108 is configured to closely control the gap between an impeller and the inner wall of a housing into which the wall pattern 1100 is incorporated. The first expandable zone 1108 can be configured with the greatest rigidity of all the expandable zones in the elongated pattern 1106. The first expandable zone 1108 corresponds to the location of (e.g., is disposed over) an impeller such as the impeller 202 and can extend along approximately the proximal one third of the elongated pattern 1106. In some embodiments, the expandable zone(s) distal of the first expandable zone 1108 provide sufficient ability to isolate the impeller from the load L or displacement D (see FIG. 35) that the length of the stiffest portion of the housing can be shortened to less than one-third the length of the housing.

In one embodiment, the elongated pattern 1106 comprises a plurality of zones of different rigidities distal of the first expandable zone 1108. For example, at least one zone can be the same, more, or less rigid compared to the first expandable zone 1108 depending on the flex pattern desired along the housing. In one embodiment, a second expandable zone 1110 and the third expandable zone 1112 are both less rigid and disposed distally of the first extendable zone 1108. The second expandable zone 1110 can be disposed between the first expandable zone 1108 and the third expandable zone 1112. The second zone 1110 may have a rigidity that is less than that of the first expandable zone 1108. In one embodiment, the third expandable zone 1112 has a rigidity that is less than the second expandable zone 1110. In some embodiments, the second zone 1110 has a greater ability to deflect in response to the load L or displacement D than does the first expandable zone 1108. In some embodiments, the third zone 1112 has the greatest ability to deflect in response to the load L or displacement D of the first, second, and third zones 1108, 1110, 1112. It may even be desirable to configure the second and third expandable zones 1110, 1112 to deform with the deformation. The pattern 1100 can be configured to deform most in the third expandable zone 1112 and progressively less proximally thereof toward the first expandable zone 1108.

The distal portion 1104 can be considered a fourth expandable zone dispose distally of the third expandable zone 1112. In one embodiment the distal portion 1104 has a rigidity that is greater than that of the third expandable zone 1112. For example, at least a proximal section 1104A of the distal portion 1104 can be configured to provide a rigidity that is similar to that of the proximal portion 1102. In some embodiments, the distal section 1104B of the distal portion 1104 can be provided with a plurality of elongate gaps therebetween to provide generally unimpeded intake of blood as discussed above. The distal section 1104B of the distal portion 1104 can also have enhanced flexibility to provide atraumatic interactions with the anatomy.

FIG. 36A illustrates more detail of one embodiment of the first expandable zone 1108. The first expandable zone 1108 comprises a proximal end 1116 comprising a plurality of longitudinally oriented members 1118 coupled with the proximal portion 1102. The first expandable zone 1108 also includes a plurality of circumferentially oriented rings 1120 arranged along the longitudinal axis of the pattern. The rings 1120 may have a sinusoidal configuration. The number of rings 1120 can be varied, and may depend on the configuration of the impeller to be disposed within the housing into which the pattern 1100 is incorporated. In one embodiment the first expandable zone 1108 includes eight circumferential rings 1120, while in other embodiments the first expandable rings 1120 includes six or seven circumferential rings 1120. A skilled artisan would understand that the first expandable zone 1108 can include any suitable number of rings 1120.

Figure 38:
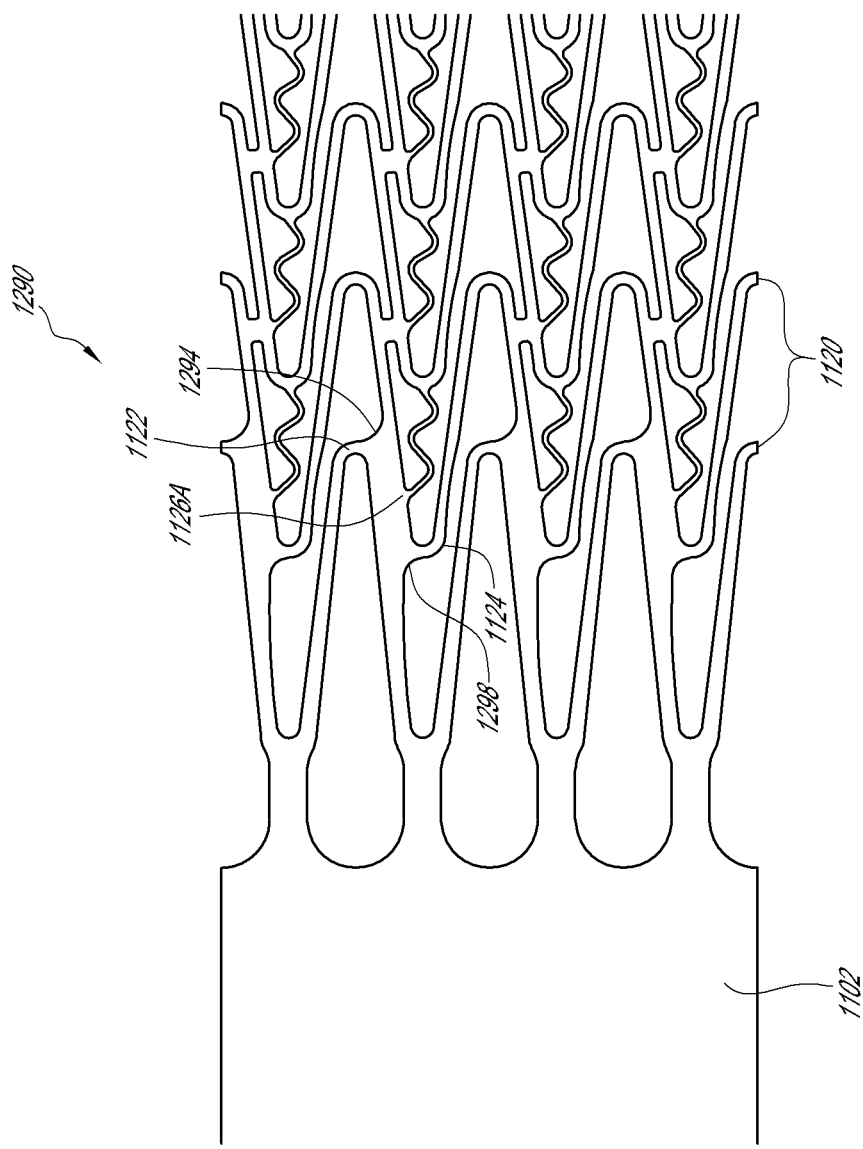
FIGS. 38-40 illustrates further embodiments of wall patterns than can be incorporated into an impeller housing.

The circumferential rings 1120 of the first expandable zone 1108 may comprise a plurality of crests and troughs 1122, 1124 that are distally and proximally oriented. FIG. 36A illustrates that the crests 1122 of a first ring in the first expandable zone 1108 are overlap with (e.g., are nested within) the troughs 1124 of a second circumferential ring 1120, where the second circumferential ring is located distal of the first circumferential ring. This arrangement enables a connector 1126 to extend substantially circumferentially from a first location on the first ring to a second location on the second ring. The first and second locations can be located just off (e.g., proximal of) a corresponding crest 1122 and just off (e.g., distal of) a corresponding trough 1124. The connector 1126 is relatively short in one embodiment, e.g., having a length that is about equal to the width of the portion of the rings 1120 that extends between the crests and troughs 1122, 1124. FIG. 38 illustrates an embodiment in which at least some circumferential connectors are widened to enhance stiffness of the structure. The width of the connectors 1026 are about equal to or in some cases greater than the length thereof. In one embodiment, a connector 1126 provides a circumferential connection between a strut forming a crest and a strut forming a trough of different adjacent rings 1120. Accordingly, the connector 1126 can be referred to herein as a radial/adjacent connector. In the first expandable zone 1108, the connectors 1126 are located at the same axial position such that a cross-section perpendicular to the length of the pattern 1100 would intersect all of the connectors 1126.

The nested arrangement of the crests and troughs 1122, 1124 of the adjacent circumferential rings 1120 (i.e., the proximity between adjacent crests and troughs) provides enhanced rigidity in the first expandable zone 1108. In one embodiment, the nested arrangement of the crests and troughs 1122, 1124 of the adjacent circumferential rings 1120 is approximately 50% overlapped in width. In some arrangements, nesting of crests and troughs 1122, 1124 is not provided, which would result in a more flexible structure all else remaining equal. In some arrangements, nesting of the crests and troughs 1122, 1124 can be as much as 80% overlapped in width, or limited by the material and manufacturing capabilities, which would result in a less flexible structure all else remaining equal. By providing connectors 1126 between each adjacent crest and troughs 1122, 1124 further enhancement of the rigidity of the first expandable zone 1108 is provided.

In one embodiment, a connector 1128 that is generally axially oriented is provided between adjacent circumferential rings 1120. The connector 1128 extends from a first end 1128A (e.g., a crest) coupled with proximal side of each trough 1124 and a second end 1128B coupled with a side portion (e.g. an arm extending between a crest and trough) of a circumferential ring 1120 disposed proximally of the first end 1128A. Accordingly, the connector 1128 can be referred to herein as an axial-to-side connector. The connector 1128 can take any suitable form, and in some embodiments are included mainly to facilitate collapsing of the housing into which the pattern 1100 is incorporated. The connector 1128 can be sinusoidal in form, for example having, in one example, a plurality of apices, such as at least three apices between the first and second ends 1128A, 1128B. In other embodiments, the connectors 1128 can be straight to provide greater rigidity to facilitate retraction of the housing into a sheath, as discussed above. In one arrangements, at least the proximal pair of rings 1120 are connected by variations of the connectors 1128 that are stiffened (e.g., made straight, thicker or wider) to reduce bending adjacent the proximal portion 1102.

The second expandable zone 1110 can be made more flexible by any suitable means. For example, FIG. 36B illustrates that the second extendable zone 1110 can be configured with enhanced flexibility by eliminating the connector 1126 between at least some of the rings 1120. FIG. 36B illustrates that in one embodiment at least a plurality of (e.g., at least four) adjacent rings 1120 are not connected to each other circumferentially, however in some embodiments at least five or six adjacent rings 1120 are not connected to each other circumferentially. Also, the second expandable zone 1110 can be made more flexible by including a connector 1128', which extends generally axially, instead of connector 1128. In one embodiment, the connector 1128' can be elongated, as compared to connector 1128, to provide enhanced flexibility. One technique for making the connector 1128' longer than connector 1128 is to connect the second end 1128B' with the trough 1124 of the next-proximal circumferential ring 1120 instead of at a location on the next proximal ring between adjacent troughs and crests. By disposing the first and second ends 1128A, 1128B' farther apart, the connector 1128' can be made longer than an otherwise similar connector 1128 to permit more apices along its length.

Another technique for enhancing the flexibility of the second expandable zone 1110 is to lengthen the connector 1128 and/or the connector 1128' by increasing the amplitude of the waves along the length of the connector compared to the amplitude in the first expandable section 1108. By increasing the amplitude, the connectors are made longer and are able to stretch and move upon application of a similar or lower force, thus being more flexible. Additionally, rather than having nesting between peaks and troughs of adjacent rings, further flexibility can be obtained by creating a gap between adjacent rings and progressively increasing the amount of gap.

In one embodiment, the flexibility of the expandable zone 1110 is progressively greater in the distal direction. This can be accomplished by lengthening the connectors 1128 and/or the connectors 1128' from one circumferential ring to the next along the length of the second expandable zone 1110. For example, a proximal aspect of the second expandable zone 1110 can include connectors 1128' with a first number of apices (e.g., five apices) and a distal aspect of the second extendable zone 1110 can include connectors 1128' with a second number of apices greater than the first number (e.g., seven apices). Or, a proximal aspect of the second expandable zone 1110 can include connectors 1128' with apices having a first average amplitude and a distal aspect of the second extendable zone 1110 can include connectors 1128' with apices having a second average amplitude greater than the first average amplitude.

Another technique for enhancing the flexibility of an expandable zone is to progressively decrease the amount of nesting of peaks and troughs of adjacent rings. For example, the crests and troughs of a first adjacent pair of circumferential rings 1120 can overlap to a greater extent than those of a second adjacent pair of circumferential rings 1120 where the first pair is proximal of the second pair.

Figure 40:
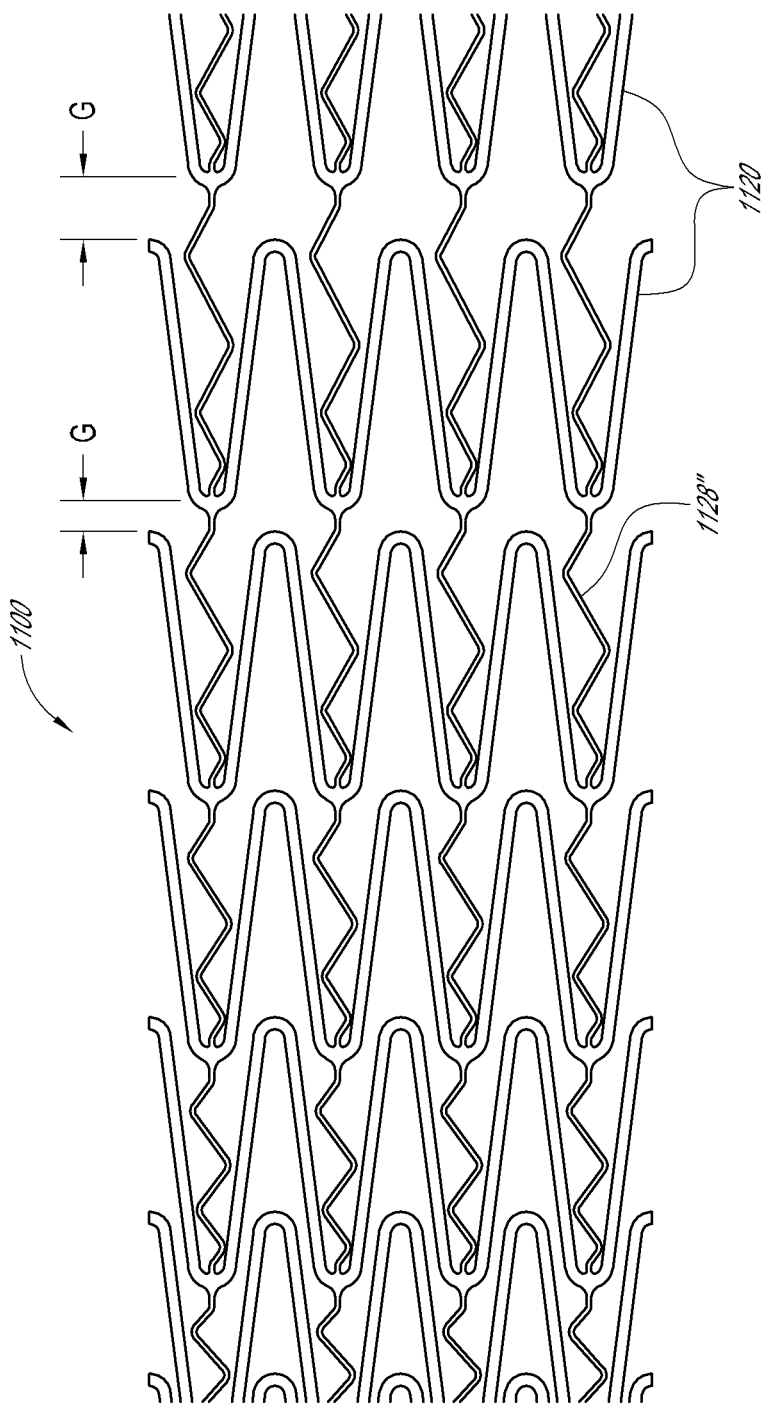

As show in FIG. 36C, a third expandable zone 1112 can be configured for greater flexibility than the second expandable zone 1110 by decreasing the amount of overlap between adjacent crests and troughs of adjacent circumferential rings 1120. For example, a first pair of adjacent rings 1120A and a second pair of adjacent rings 1120B are provided with overlap of length OL1 and OL2 respectively. The first pair of rings 1120A is distal to the second pair of rings 1120B. In one embodiment, the second pair of rings are disposed in the second expandable zone 1110 and the first pair are disposed in the third expandable zone 1112. In another embodiment, the third expandable zone 1112 has an amount of overlap between adjacent rings that varies along the length of the third expandable zone 1112. The overlap amount can vary between each pair of adjacent rings or in a less discrete manner. FIG. 40 shows a variation in which overlap is eliminated and spacing is provided that can increase distally.

Flexibility of the pattern 1106 in the third expandable zone 1112 can also be varied in other ways, such as by lengthening the connectors 1128'. Because of their sinusoidal shape, the length of the connectors 1128' can be increased (while incidentally reducing the wavelength of the connectors 1128') without increasing the distance between the adjacent rings (e.g., adjacent rings 1120A). As illustrated in FIG. 36C, in the distal portion of the third expandable zone 1112, such as near the first pair of adjacent rings 1120A, the longitudinal distance between the first and second ends of the connectors 1128' is approximately equal to the longitudinal distance between the peaks and troughs of each circumferential ring 1120. Because of the sinusoidal shape of the secondary connector 1128', the length of the secondary connector 1128' is much longer than this longitudinal distance. These factors, e.g., the length of the connector 1128', relative to the distance between adjacent rings, can provide greatly enhanced flexibility toward the distal and the third expandable zone 1112.

FIG. 36D illustrates in greater detail one embodiment of the distal portion 1104. The proximal section 1104A for the distal portion 1104 includes a circumferential ring 1120 and a plurality of connectors extending distally thereof. For example a connector 1128' having a sinusoidal form can extend distally of a trough 1122 of the ring 1120. The connector 1128' can include a plurality of apices, for example three apices. In one embodiment, a connector 1128' expends distally from each trough 1122 of the circumferential ring 1120. A connector 1126 can extend generally circumferentially from a side surface of an arm extending between each trough 1122 and each crest 1124 of the ring 1120. The connector 1126 enhances the stiffness of pattern 1100 in the region of opening for blood intake so that the openings will remain open when a housing incorporating the pattern 1100 is expanded.

In one embodiment the distal section 1104B of the distal portion 1104 includes a circumferential ring 1132 and a plurality of axial members 1134. The circumferential ring 1132 may be configured to provide a larger expanded shape than the shape provided by the circumferential rings 1120. For example, the circumferential ring 1132 can include a plurality of proximal troughs 1136, a plurality of distal crest 1138, and a plurality of elongate members 1140 extending between the crests and troughs. The elongate members 1140 are substantially longer than the corresponding elongate members of the circumferential rings 1120. As a result, when expanded, circumferential ring 1132 provides enlarged perimeter compared to the circumferential rings 1120. The axial members 1134 can take any suitable shape, but may be configured to be integrated into an atraumatic distal structure, as discussed above. Openings are formed between adjacent axial members 1134, the elongate members 1140 and the troughs 1136.

The techniques discussed above advantageously reduce the stiffness of the wall pattern 1100 at a distal location compared to a location at which an impeller will operate in a manner that spreads out deformation of the housing over a length. This isolates the impeller zone from the effect of the load L or displacement D illustrated in FIG. 35. In various embodiments, the length of the housing that is deformed is elongated to prevent focused bending that could result in a kinking of the housing, which could result in damage or significant flow blockage.

Other techniques can be employed for modifying the location of or elongating the transition zone 1090 can be employed. For example, in one technique, the axial spacing between the circumferential rings can be varied at discrete locations or continuously along the length of the housing. The first expandable zone 1108 can have a first axial density of circumferential rings 1120, the second expandable zone 1110 can have a second axial density of circumferential rings 1120, and the third expandable zone 1112 can have a third axial density of circumferential rings 1120, where at least the third density is less than the first density. Example embodiments provide a first axial density of about 8 circumferential structures per inch and a third axial density of about 4 circumferential structures per inch. In other embodiments, about one-half the axial density of circumferential structure can be provided in a more flexible zone compared to a less flexible zone. Further embodiments of enhanced flexibility due to changes in spacing of circumferential rings or structures are described below in connection with FIGS. 39 and 40.

Varying at least one aspect of sinusoidal rings, e.g., the number of crests and troughs, the frequency of crests and/or troughs, and/or amplitude of the rings can also provide stiffness variation along the length of the pattern 1100.

One variation on the embodiment of FIG. 36 provides for varying the pattern of the circumferential rings 1120 in different zones. For example, the first expandable zone 1108 can have circumferential rings 1120 with a first number of distal peaks and proximal peaks and a portion of the pattern 1100 distal of the first expandable zone 1108 can have circumferential rings 1120 with a second number of distal and proximal peaks, and the first number of distal and proximal peaks can be less than the second number of distal and proximal peaks.

In another variation, a transition zone is provided that is configured to have a continuously varying stiffness from the distal end of the first expandable zone 1108 to the proximal section 1104A of the distal portion 1104. The continuous variation of the transition zone produces an arcuate shape upon application of the load L or displacement D in FIG. 35. This advantageously eliminates or minimizes the risk of buckling or kinking of the housing into which this modified pattern is incorporated. Alternatively, a transition zone can be configured to minimize focused bending or kinking but to assure that if focused bending or kinking occurs, it will occur closer to the distal portion 1104 than to the first expandable zone 1108.

Figure 37A:
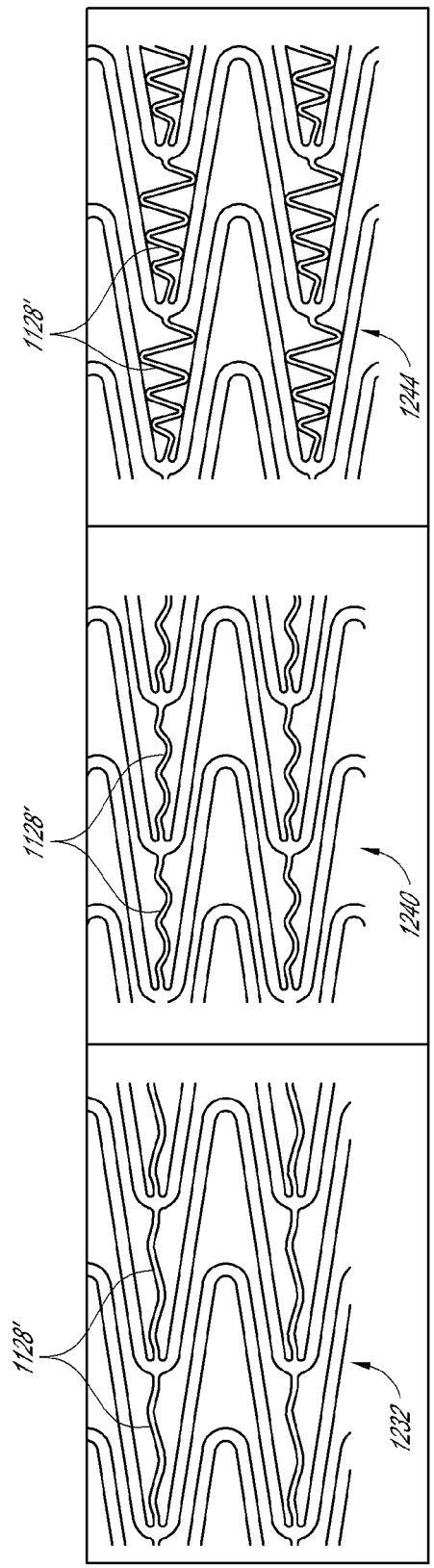
FIG. 37A-B illustrates additional techniques for isolating an impeller region of an impeller housing from a load.
Figure 37B:
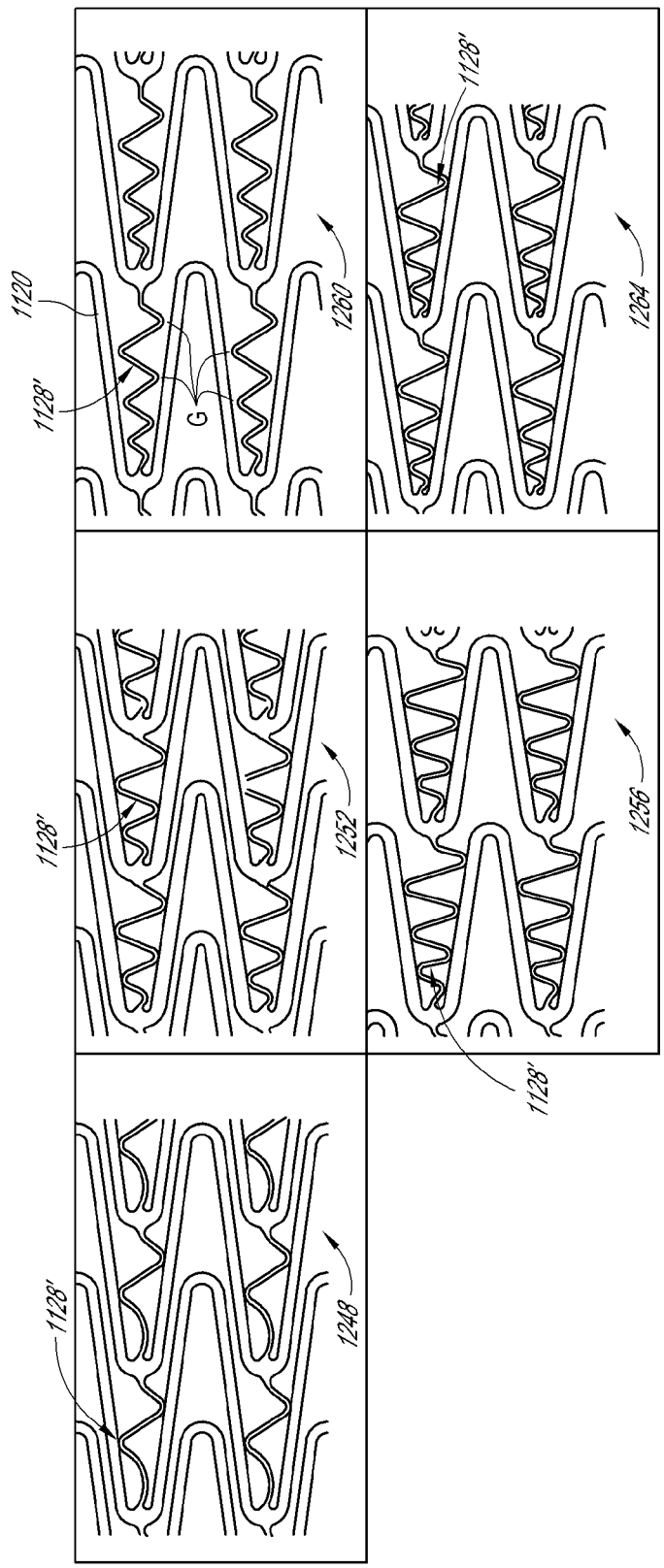

FIGS. 37A-37B illustrate a number of connector variations that could be incorporated into the pattern 1100 to modify the stiffness between or within one of the expandable zones. In one variation, a wall pattern 1232 corresponding to the first expandable zone 1108 has a connector 1128' that has a linear configuration, for example, having only 3 apices on the connector and with a smallest amplitude compared to patterns 1240 and 1244, with a first plurality of (e.g., three) bends or apices that provides a first longitudinal stiffness. A wall pattern 1240 corresponding to a portion of the pattern 1100 that is more flexible than the first expandable zone 1108 has a connector 1128' that has a linear configuration with a second plurality of (e.g., five) apices and each with a larger amplitude than the pattern 1232, that provides a second longitudinal stiffness. The second plurality of apices includes more bends than the first plurality. A wall pattern 1244 corresponding to a portion of the pattern 1100 that is more flexible than the first expandable zone 1108 has a connector 1128' that is much longer (i.e., having a larger amplitude or connecting material between apices) than the connectors in the patterns 1232, 1240 and as a result comprises a third longitudinal stiffness that is less than the first or second longitudinal stiffnesses. The connector 1128' of the wall pattern 1244 is much longer by spanning the entire width of a trough a plurality of times between tends connected to axially aligned troughs of adjacent rings 1120.

FIG. 37B shows further variants in which other variable are modified. For example, a wall pattern 1248 is provided in which the radius of curvature of an apex toward the proximal end of a connector 1128' is increased compared to the curvature of other apices. In other words, one segment of the connector is curved rather than straight. This arrangement can be used in a portion of a wall structure where greater stiffness is needed, such as near the members 1118 connect the proximal most circumferential ring to the proximal portion 1120.

A wall pattern 1252 can include a connector 1128 with a greater number of apices, e.g., five apices compared to three in pattern 1248, with comparable amounts of overlap.

A wall pattern 1256 can provide both a larger number of apices and a lesser amount of nesting or overlap between adjacent rings 1120. The pattern 1256 includes seven apices. The apices have progressively larger amplitude to maximize the length of the connector 1128' for a given trough to trough spacing.

A wall pattern 1260 provides another means for varying the stiffness of the structure. In the pattern 1260, a similar number of apices is provided compared to the pattern 1256, however, the average amplitude is less. In this embodiment, gaps G are provided in the unexpanded state between the connector 1128' and the arms of the ring 1120. Thus, the length of the connector 1128' is less than it could be given the arrangement of the rings 1120. By reducing the average amplitude, the overall stiffness can be enhanced other variable being held constant.

Wall pattern 1264 provides another variation similar to pattern 1260 except that the average amplitude is maximized by eliminating the gap G and a greater amount of nesting or overlap is provided. The resulting structure may have comparable stiffness to that of wall pattern 1264 but provide more material coverage which reduces the surface area that needs to be coated. Also, this arrangement may reduce the percentage contribution of the coating to the mechanical performance of a housing into which it is incorporated.

Although the foregoing discussion of FIGS. 35-37B has focused on varying the pattern 1100 to control the stiffness of a housing into which it is integrated, a difference in stiffness can also be provided by changing properties of a coating disposed over the pattern 1100. The coating is provided to enclose a space in a housing formed with the pattern 1100 such that blood can flow therethrough. In some embodiments, the coating can be made with varying thickness to change the stiffness of the housing at a location where less stiffness is preferred. For example, the first expandable zone 1108 can be coated with a first thickness and the second expandable zone 1110 can be coated with a second thickness that is less than the first thickness. In other variations, the third expandable zone 1112 can be coated with a third thickness that is less than the first and second thicknesses. In other embodiments, a continuous and not varying mesh structure is provided and at least the second thickness of the coated material is less than the first thickness of the coated material.

Other techniques can be applied for coating the mesh 203 or pattern 1100 with a continuous thickness of coating but with a varying stiffness. For example, different materials could be used to coat the first expandable zone 1108 and at least one of the second and third expandable zones 1110, 1112. Also, the porosity of the coating can be varied along the length of the housing to change the flexibility. The porosity of the first expandable zone 1108 can be less than that of a portion of the housing distal the first expandable zone 1108. In one embodiment, the porosity of the first expandable zone 1108 is less than that of the second and third expandable zones 1110, 1112.

FIG. 38 shows another embodiment of a wall pattern 1290 that provides enhanced stiffness. Is it desirable to enhance the stiffness of the first expandable zone 1108 particularly adjacent to the proximal portion 1102. This is in part because the connection between the expandable zone 1108 and the non-expanding proximal portion can be an area of focused bending. One technique for reducing the bending at this area is to provide connectors 1126A that are wider the connectors 1126.

As discussed above, the connectors 1126 have a width that is similar to the length thereof. In this context, the length is considered the distance that the connector spans between adjacent arms of axially overlapping neighboring rings 1120 and the width is a distance perpendicular to the length. In contrast, the connectors 1126A are much wider and/or longer than the connectors 1126, and are similar to the connectors 1126 while acting as a merged section along the length or a portion of the length between the adjacent arms of the nested circumferential rings. The connectors 1126A have a width that is several times the length thereof. In one embodiment the width of the connector 1126A is at least about two times the length of the connector 1126A. In another embodiment, the width of the connector 1126A is at least about four times the length of the connector 1126A. In one embodiment, the connector 1126A is configured to extend from a crest 1122 of a first circumferential ring 1120 to a trough 1124 of a second circumferential ring 1120 that is immediately distal the first circumferential ring. In one embodiment, the connector 1126A has a first radius portion 1294 that extends from a crest 1122 of the first circumferential ring to a location on an arm of the second circumferential ring that is distal of the crest 1122. The connector 1126A also can have a second radius portion 1298 that extends from a trough 1124 of the second circumferential ring to a location on an arm of the first circumferential ring that is proximal of the trough 1124 of the first circumferential ring.

Figure 39:
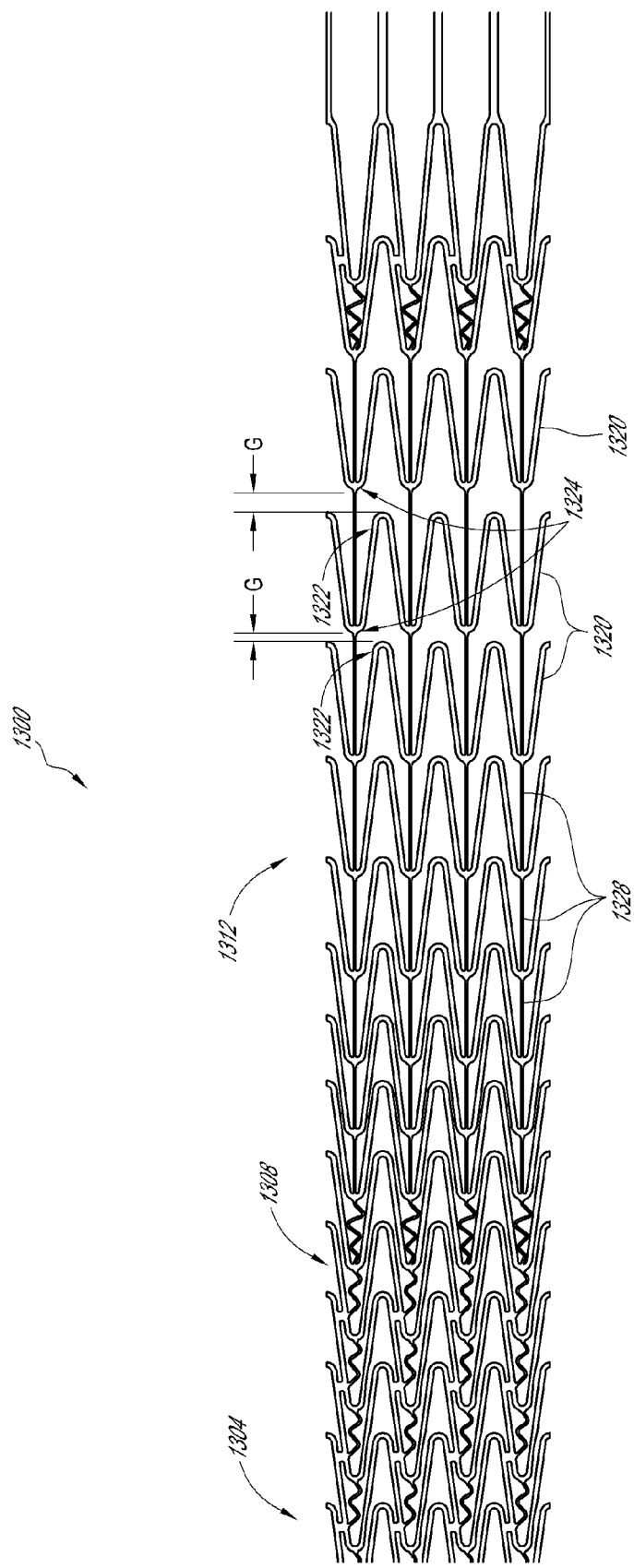

In the embodiments of FIGS. 39 and 40, changing overlap between neighboring crests and troughs is a primary technique for modifying the stiffness of a portion of a wall pattern 1300. The pattern 1300 can be incorporated into the housing 202. The pattern 1300 includes a relatively stiff proximal zone 1304, a transition zone 1308, and a distal zone 1312. Other aspects of the pattern can be similar to those described above.

The distal zone 1312 is configured to be progressively more flexible toward the distal end of the pattern 1300. In this embodiment, the spacing or overlap between neighboring rings 1320 is greatest adjacent to the transition zone 1308 and decreases toward the distal end of the distal zone 1312. In the FIG. 39 embodiment, a portion of the distal zone 1312 has no overlap between crests 1322 of a ring 1320 and troughs 1324 of a neighboring ring 1320. Also, a gap G defined between nearest peaks 1322 and troughs 1324 increases toward the distal end of the distal zone 1312.

In the embodiment of FIG. 39, the axial connectors 1328 in the distal zone 1312 are straight and are longitudinally aligned with the longitudinal axis of the pattern 1300. The connectors 1328 will be stiffer than other axial connectors described herein that include sinusoidal patterns. The decreasing overlap and/or increasing gap in the distal zone 1312 compensates for the relatively stiff straight connectors 1328 to provide acceptable load dampening performance.

FIG. 40 shows a variation of the wall pattern 1100 in which the region illustrated in FIG. 36C is modified to transition from at least some overlap between neighboring crests and troughs to no overlap and then to progressively larger spacing between neighboring crests and troughs. In addition, as illustrated in FIG. 40, the connector 1128" can include a plurality of sharp, generally linear and/or angled apices/peaks (e.g., zigzag-shaped), as opposed to the sinusoidal, wave-like connector 1128' described herein. This embodiment is similar to that of FIG. 39 but has greater flexibility, particularly in bending.

V. Impeller Housing Configurations Providing Flow Enhancement

Figure 41:
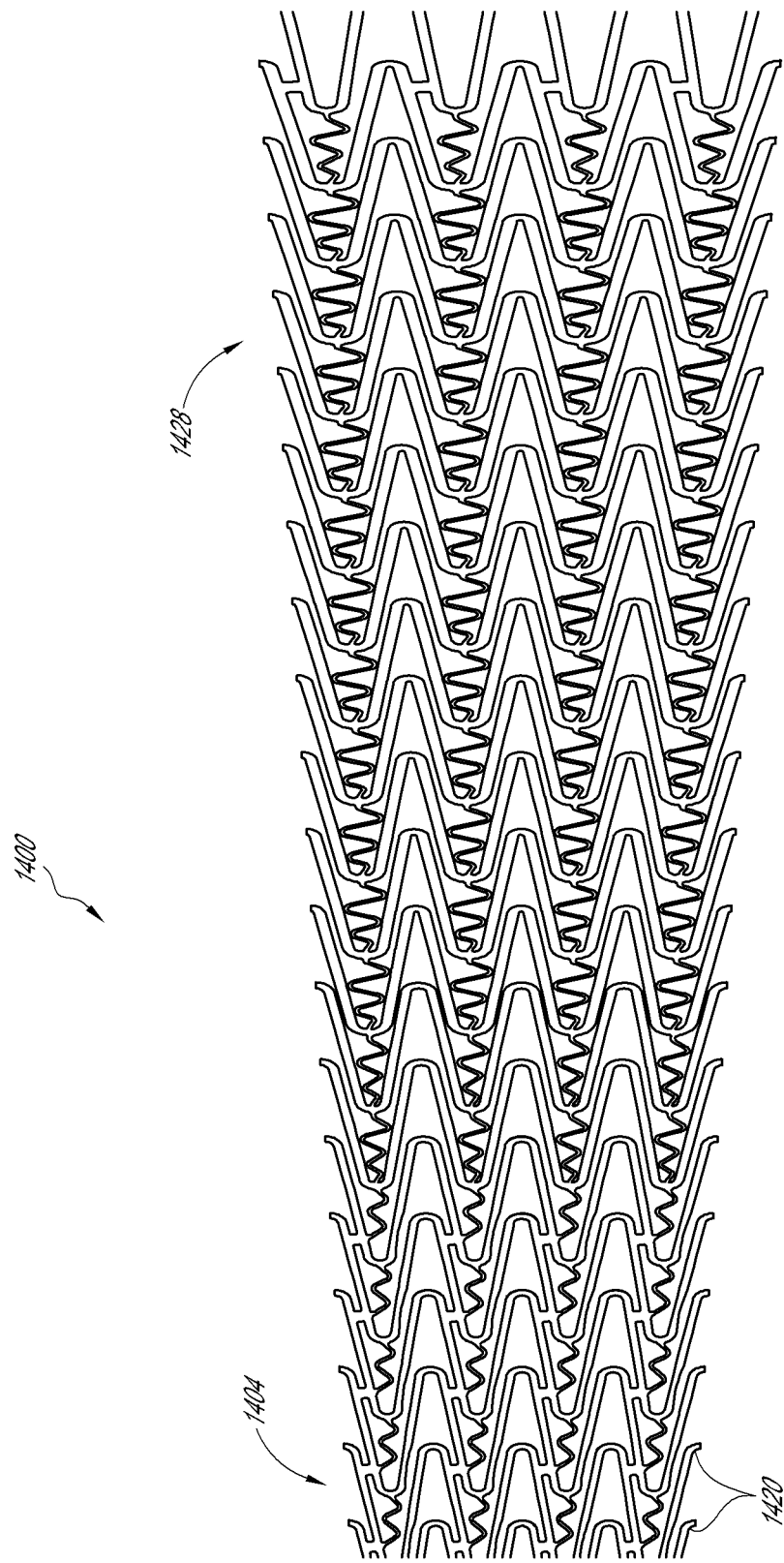
FIG. 41 illustrates another embodiment of a wall pattern than can be incorporated into an impeller housing to enhance the efficiency of an impeller disposed therein.

FIG. 41 illustrates another wall pattern 1400 that advantageously enhances the flow of the blood through the housing (e.g., the housing 202, 1020 or other housings described herein) in which an impeller operates.

The wall pattern 1400 includes a proximal portion 1404 that has a relatively stiff arrangement. The proximal portion 1404 corresponds to the location where an impeller operates when the wall pattern is disposed in an impeller housing. At least two proximal rings 1420 are connected by a plurality of circumferential connectors, similar to those discussed above. A distal portion 1428 of the wall pattern 1400 disposed distal of the proximal portion 1404 is configured to enhance flow by providing a distally expanding configuration. For example, the inner diameter or cross-sectional size of the housing in which the distal portion 1428 of the wall pattern 1400 is disposed can be larger than the inner diameter or cross-sectional size of the housing corresponding to the proximal portion 1404. In one embodiment, the size is progressively larger, e.g., with each ring being configured to be larger than the next proximal ring.

The wall pattern 1400 provides a distally expanding configuration by making the crest to trough distance greater in the distal portion 1428 than in the proximal portion 1404. The crest to trough can be larger toward the distal end of the distal portion 1428 than adjacent to the proximal end of the distal portion 1428. The crest to trough distance of each ring can be lengthened by increasing the length of each ring that spans between a crest and adjacent trough. Another technique for increasing the expanded size of the housing is to enlarge the crests and/or the troughs. These can be enlarged by increasing an inner radius of the crest and/or trough.

The wall pattern 1400 and associated housing is advantageous in that a heart pump operates more effectively when the inner wall of the housing directs the blood flow to the impeller. In one technique significant pump efficiency increase can be obtained by configuring the wall pattern 1400 to expand in the distal portion 1428 to a diameter that is approximately 50% or more larger than in the proximal portion 1404. By both maximizing the diameter at the distal portion 1428, cavitation can be reduced and flow efficiency is increased. In addition to enlarging the inner size (e.g., diameter) of location of a housing corresponding the distal portion 1428, the length of the distal portion 1428 or a portion of the housing distal the impeller can be increased. In some embodiments, a housing incorporating the wall pattern 1400 can be both elongated and configured to have a distally expanding configuration to increase pump efficiency.

In addition to use as an LVAD, the device of the present invention may also be used as a right ventricular assist device in a manner similar to that described above. Other applications of the device according to the present invention include providing additional blood flow to other organs, assisting the heart during operations and the like.

Applications of the improved fluid pump design described herein are not limited to ventricular assist devices. The improved cannula and impeller designs are useful for any application where a stored configuration having a reduced diameter is useful for locating the pump at a desired location. For example, a fluid pump operating underground may be introduced into a pipe, channel or cavity through an opening of lesser diameter, and operate at a diameter greater than that of the opening used. Applications of an impeller deploying within an expandable cannula include a collapsible fire hose with an integral booster pump, a collapsible propeller, a biomedical pump for a biological fluid, and the like.

VI. Methods

As discussed above, in various embodiments the heart pump 10 is inserted in a less invasive manner, e.g., using techniques that can be employed in a catheter lab. Various general techniques pertinent to the heart pump 10 are described in U.S. patent application Ser. No. 12/829,359, filed on Jul. 1, 2010, and entitled *Blood Pump With Expandable Cannula*, which is incorporated by reference herein in its entirety and for all purposes.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A catheter assembly for a heart pump, comprising:
an elongate tubular member;
a hub coupled with a proximal end of the elongate tubular member;
a plurality of structural members forming a distal portion of an impeller housing;
a locking device disposed between the structural members and the hub configured to prevent the elongate tubular member from being separated from the structural members when the catheter assembly is in use.

2. The catheter assembly of claim 1, wherein the locking device comprises a barb at the distal end of the structural members and a narrow aperture channel formed at a proximal aspect of the hub, the narrow aperture channel permitting insertion of the barb and resisting retraction of the barb.

3. The catheter assembly of claim 1, wherein the hub comprises a recess formed at a proximal end thereof and further comprising a core member configured to be inserted into the recess, the catheter assembly being configured to prevent the structural members from being retracted from the core member.

4. The catheter assembly of claim 3, wherein the structural member and the core member comprises a T-shaped configuration such that a proximal narrow portion of the recess abuts and opposes retraction of a wider portion of the structural member disposed distal thereof.

5. The catheter assembly of claim 3, wherein the hub is coupled to the elongate tubular member through the core member.

6. The catheter assembly of claim 3, wherein the core member comprises a distal portion configured to securely couple with the elongate tubular member.

7. The catheter assembly of claim 6, wherein the distal portion of the core member extends distally of the hub.

8. The catheter assembly of claim 3, wherein a barrier structure is provided within the recess of the hub to separate at least a portion of the recess from a lumen within the catheter assembly.

9. The catheter assembly of claim 1, wherein the hub has an increasing outer profile along its length.

10. The catheter assembly of claim 1, wherein the hub has an elongated tapered section having a distal end disposed distally of the distal portion of the core member to provide a dilating structure.

11. The catheter assembly of claim 1, wherein the hub comprises a distal portion configured to securely couple with the elongate tubular member.

12. The catheter assembly of claim 1, wherein the locking device comprises a through-hole in the structural members configured to permit a first portion of material disposed on an inside surface of the structural member to branch through to a second portion of material disposed on an outside surface of the structural member.

13. The catheter assembly of claim 12, wherein the locking device comprises a plurality of through-holes disposed along a distal length of at least one of the structural members.

14. The catheter assembly of claim 12, wherein the locking device comprises a circular structure disposed at the distal end of the at least one of the structural members.

15. A catheter assembly for a heart pump, comprising:
an elongate tubular member;
an expandable housing disposed at the distal end of the elongate tubular member, the expandable housing configured to house an impeller and to convey blood from an intake toward the impeller in use;
an expandable tip coupled with the distal end of the expandable housing, the expandable tip having a collapsed configuration in which a tapered profile is provided for facilitating advancement through an anatomical structure and having an expanded configuration for spacing the intake from the anatomy adjacent to where the pump is operates.

16. The catheter assembly of claim 15, further comprising a plurality of elongate arcuate structural members disposed between the expandable housing and the expandable tip, the arcuate structural members providing wide openings for blood intake into the housing.

17. The catheter assembly of claim 15, further comprising a sheath adapted to be advanced relative to the elongate tubular member to be positioned over the expandable housing and the expandable tip to maintain the tip in the collapsed configuration.

18. The catheter assembly of claim 17, wherein the tip comprises a plurality of arms having proximal portions configured with reduced thickness to engage with a sheath.

19. The catheter assembly of claim 17, wherein the tip comprises a plurality of arms coupled as their distal ends with a hub disposed around a guidewire port, the arms having proximal ends coupled with the expandable housing.

20. The catheter assembly of claim 15, wherein the expandable tip is bulbuous when in the expanded configuration.

21. A catheter assembly for a heart pump, comprising:
an impeller shaft and an impeller blade extending from the impeller shaft;
a housing in which the impeller shaft is journaled for rotation, the housing having an elongate wall structure disposed circumferentially about the impeller blade and extending distally and proximally thereof, a distal region of the wall structure being configured to isolate a proximal region of the wall structure from deflection due to application of loads by the heart during operation of the impeller assembly within the patient.

22. The catheter assembly of claim 21, wherein the wall structure comprises a first region disposed over the impeller and a second region distal the first region, the second region having less stiffness than the first region such that loads applied within or distal of the second region produces deformation of the housing that is primarily distal of the first region.

23. The catheter assembly of claim 22, wherein the wall structure comprises a mesh structure and a coating disposed over the mesh, the mesh structure being arranged with a first stiffness in the first region and a second stiffness in the second region, the second stiffness being less than the first stiffness.

24. The catheter assembly of claim 23, wherein the mesh structure in the second region has progressively less stiffness toward the distal end of the housing.

25. The catheter assembly of claim 23, wherein the mesh structure further comprises a third region having a third stiffness that is less than the second stiffness.

26. A percutaneous heart pump, comprising:
a catheter assembly having a proximal end, a distal end, and an elongate body disposed therebetween, the elongate body configured such that the distal end can be disposed inside heart chamber of a human patient while a proximal end is disposed outside the patient,
the distal end comprising an expandable housing being configured to be insertable into a peripheral vessel in a low profile configuration and to be expanded to a larger profile within the patient;
an impeller shaft and an impeller blade extending from the impeller shaft, the impeller shaft is journaled for rotation in the distal portion of the catheter assembly;
wherein the expandable housing comprising:
an elongate wall structure disposed circumferentially about the impeller blade and extending distally and proximally thereof, the wall being configured to maintain a gap between the blade an inner surface of the wall structure within a selected range over a range of transverse loading corresponding to forces generated during systole and diastole of the heart.

27. The percutaneous heart pump of claim 26, wherein the elongate wall structure comprises a metallic mesh disposed in a fluid-tight structure, the elongate wall structure having a stiffness profile that is greatest at a longitudinal position corresponding to that of the impeller blades and being decreased distally thereof.

28. The percutaneous heart pump of claim 27, wherein the metallic mesh structure is more dense in a region corresponding to the impeller blade and is less dense distally thereof.

29. The percutaneous heart pump of claim 28, wherein the metallic mesh structure comprises circumferential rings having a greater concentration in the region corresponding to the impeller blade and is less dense distally thereof.

30. The percutaneous heart pump of claim 28, wherein the metallic mesh structure comprises circumferential rings connected by axial connectors, the axial connectors being stiffer in the region corresponding to the impeller blade and being less stiff distally thereof.

31. The percutaneous heart pump of claim 27, wherein the fluid-tight structure comprises a polymeric coating, the polymeric coating being thicker in a region corresponding to the impeller blade and is less dense distally thereof.

32. A catheter assembly for a heart pump, comprising:
an impeller shaft and an impeller blade extending from the impeller shaft;
an impeller housing in which the impeller shaft is journaled for rotation, the housing comprising:
an inlet;
an outlet; and
an elongate wall structure disposed circumferentially about the impeller blade and extending distally and proximally thereof between the inlet and outlet, the wall structure adjacent to at least one of the inlet and the outlet being configured to maintain a bulbous shape when deployed.

33. The catheter assembly of claim 32, wherein the elongate wall structure comprises a mesh structure and a coating disposed over the mesh structure, the coating having a stiffened region adjacent the inlet to maintain a first transverse size, the transverse size of the wall structure decreasing proximally and distally of the stiffened region.

34. The catheter assembly of claim 33, wherein the stiffened region comprises an annular band of the wall structure that is thicker than the thickness of the wall structure proximal of the stiffened region.

35. The catheter assembly of claim 32, wherein the elongate wall structure comprises a mesh structure and a coating disposed over the mesh structure, the coating having a stiffened region adjacent the outlet to maintain a first transverse size and the wall structure being configured distal of the outlet to have a transverse size that is less than the first transverse size.

36. The catheter assembly of claim 32, wherein the impeller comprises a diffuser and the wall structure comprises a reinforced annular portion, a flared section extending distally of the annular portion and being disposed over a distal portion of the diffuser and a plurality of leaflets disposed proximally of the annular portion.

37. A catheter assembly for a heart pump, comprising:
an impeller shaft and an impeller blade extending from the impeller shaft;
a housing in which the impeller shaft is journaled for rotation, the housing having an elongate wall structure disposed circumferentially about the impeller blade and extending distally and proximally thereof, the wall structure being sufficiently deformable to be displaced by ambient conditions during operation of the impeller assembly within a patient.

38. The catheter assembly of claim 37, wherein the housing is sufficiently flexible to be deflected by fluid flow generated by the impeller blade upon movement of the impeller blade toward the wall.

39. The catheter assembly of claim 38, wherein the wall comprises a plurality of struts and a covering disposed over the struts, the struts and covering being disposed circumferentially about the impeller blade.

40. The catheter assembly of claim 39, wherein the plurality of struts comprises a first strut density at an axial position corresponding to the impeller blade and a second strut density greater than the first strut density at a location proximal or distal of the location of the first density.

41. The catheter assembly of claim 39, wherein the plurality of struts comprises a first average strut thickness at an axial position corresponding to the impeller blade and a second average strut thickness greater than the first average strut thickness at a location proximal or distal of the location of the first density.

42. The catheter assembly of claim 39, wherein the covering comprises a first average thickness at an axial position corresponding to the impeller blade and a second average thickness greater than the first average thickness at a location proximal or distal of the location of the first density.

43. The catheter assembly of claim 39, wherein the plurality of struts comprises a plurality of circumferentially extending sinusoidal member.

44. The catheter assembly of claim 39, wherein the sinusoidal members are elastically deformable at least along a length extending substantially from a proximal end of the impeller blade to a distal end of the impeller blade.

45. The catheter of claim 37, wherein the housing is sufficiently flexible to be deflected to a converging or diverging configuration at an axial position upstream of an impeller inlet plane.

46. The catheter of claim 37, wherein the housing is sufficiently flexible to be deflected to a diverging configuration to produce a diffusing or deswirling effect at an axial position downstream of an impeller outlet plane.

47. An impeller assembly for a heart pump, comprising:
an impeller shaft and an impeller blade extending from the impeller shaft; and
a housing in which the impeller shaft is journaled for rotation, the housing comprising an impeller blade zone, an inlet zone, and an outlet zone, the impeller blade zone being elongate and having a substantially constant transverse size at least from proximal of the impeller blade to distal of the impeller blade;
wherein the impeller zone is disposed between the inlet zone and the outlet zone; and
wherein at least one of the inlet zone and the outlet zone is configured to reduce fluttering of the housing when the heart pump is operating.

48. The impeller assembly of claim 47, wherein the inlet zone comprises enhanced stiffness compared to the stiffness of the impeller zone.

49. The impeller assembly of claim 47, wherein the outlet zone comprises enhanced stiffness compared to the stiffness of the impeller zone.

50. A catheter assembly for a heart pump, comprising:
an impeller shaft and an impeller blade extending from the impeller shaft;
a housing in which the impeller shaft is journaled for rotation, the housing having an elongate wall structure a portion of which is disposed circumferentially about the impeller blade and the impeller shaft, the wall structure being configured to provide a first stiffness over the impeller blade and a second stiffness greater than the first stiffness at a location proximal of the impeller blade to reduce bending of the housing proximal of the blade.

51. The catheter assembly of claim 50, wherein the wall structure comprises a first plurality of circumferential sinusoidal rings being joined by a first plurality of generally circumferentially oriented connectors to provide the first stiffness and in the and a second plurality of circumferential sinusoidal rings being joined by a second plurality of generally circumferentially oriented connectors to provide the second stiffness.

* * * * *

UNITED STATES PATENT AND TRADEMARK OFFICE
CERTIFICATE OF CORRECTION

PATENT NO.        : 8,485,961 B2                                       Page 1 of 1
APPLICATION NO.   : 13/343617
DATED             : July 16, 2013
INVENTOR(S)       : Campbell et al.

It is certified that error appears in the above-identified patent and that said Letters Patent is hereby corrected as shown below:

On the Title page, Item 57, Under "ABSTRACT", please replace "bulbuous" with -- bulbous --.

In the Specification:

In column 12, line 32, please replace "there of," with -- thereof --.

In column 23, line 42, please replace "FIG." with -- FIGS. --.

In the Claims:

In Claim 20, column 37, line 4, please replace "bulbuous" with -- bulbous --.

In Claim 45, column 39, line 21, please replace "catheter" with -- catheter assembly --.

In Claim 46, column 39, line 25, please replace "catheter" with -- catheter assembly --.

Signed and Sealed this
Twenty-ninth Day of April, 2014

Michelle K. Lee
*Deputy Director of the United States Patent and Trademark Office*